US007279324B2

(12) United States Patent
Barak et al.

(10) Patent No.: US 7,279,324 B2
(45) Date of Patent: Oct. 9, 2007

(54) NUCLEIC ACID ENCODING G-PROTEIN COUPLED RECEPTOR WITH MODIFIED DRY MOTIF

(75) Inventors: Larry S. Barak, Durham, NC (US); Robert H. Oakley, Durham, NC (US); Marc G. Caron, Durham, NC (US); Stephane A. Laporte, Outremont (CA); Alyson Wilbanks, Chapel Hill, NC (US)

(73) Assignee: Duke University, Durham, NC (US)

( * ) Notice: Subject to any disclaimer, the term of this patent is extended or adjusted under 35 U.S.C. 154(b) by 835 days.

(21) Appl. No.: 10/054,616

(22) Filed: Jan. 22, 2002

(65) Prior Publication Data

US 2003/0049643 A1 Mar. 13, 2003

Related U.S. Application Data

(60) Provisional application No. 60/263,406, filed on Jan. 23, 2001.

(51) Int. Cl.
*C12N 15/63* (2006.01)
*C12N 15/12* (2006.01)

(52) U.S. Cl. .................. 435/320.1; 435/325; 536/23.5

(58) Field of Classification Search ..................... None
See application file for complete search history.

(56) References Cited

U.S. PATENT DOCUMENTS

| 4,342,566 | A | 8/1982 | Theofilopoulos et al. |
| 4,493,795 | A | 1/1985 | Nestor, Jr. et al. |
| 4,816,397 | A | 3/1989 | Boss et al. |
| 4,816,567 | A | 3/1989 | Cabilly et al. |
| 5,034,506 | A | 7/1991 | Summerton et al. |
| 5,264,221 | A | 11/1993 | Tagawa et al. |
| 5,539,082 | A | 7/1996 | Nielsen et al. |
| 5,569,824 | A | 10/1996 | Donehower et al. |
| 5,569,827 | A | 10/1996 | Kessous-Elbaz et al. |
| 5,602,240 | A | 2/1997 | De Mesmaeker et al. |
| 5,625,048 | A | 4/1997 | Tsien et al. |
| 5,665,710 | A | 9/1997 | Rahman et al. |
| 5,714,331 | A | 2/1998 | Buchardt et al. |
| 5,719,262 | A | 2/1998 | Buchardt et al. |
| 5,767,337 | A | 6/1998 | Roses et al. |
| 5,777,079 | A | 7/1998 | Tsien et al. |
| 5,891,646 | A | 4/1999 | Barak et al. |
| 6,066,476 | A | 5/2000 | Tsien et al. |
| 6,107,324 | A | 8/2000 | Behan et al. |
| 6,110,693 | A | 8/2000 | Barak et al. |
| 6,140,509 | A | 10/2000 | Behan et al. |
| 6,150,393 | A | 11/2000 | Behan et al. |

FOREIGN PATENT DOCUMENTS

| WO | WO93/24510 A1 | 12/1993 |
| WO | WO94/26764 A1 | 11/1994 |
| WO | WO96/40062 A1 | 12/1996 |
| WO | WO 00/12704 A2 | 3/2000 |

OTHER PUBLICATIONS

Alewijnse, Astrid E., et al., *The Effect of Mutations in the DRY Motif on the Constitutive Activity and Structural Instability of the Histamine $H_2$ Receptor*, Molecular Pharmacology, 2000, pp. 890-898, 57, American Society for Pharmacology & Experimental Therapeutics, 0026-895X/00/050890, Baltimore, MD.

Angers, S., et al., *Detection of $\beta_2$-Adrenergic receptor dimerization in living cells using bioluminescence resonance energy transfer (BRET)*, Proceedings of the National Academy of Sciences, vol. 97, No. 7, Mar. 28, 2000, pp. 3684-3689, Proc.Natl. Acad. Sci, USA.

Attramadal, H., et al., *β-Arrestin2, a Novel Member of the Arrestin/β-Arrestin Gene Family*, Journal of Biological Chemistry, vol. 257, No. 25, Sep. 5, 1992, pp. 17882-17890, The American Society for Biochemistry and Molecular Biology, Inc., USA.

Barak, L.S., et al., *A β-Arrestin/Green Fluorescent Protein Biosensor for Detecting G Protein-coupled Receptor Activation*, Journal of Biological Chemistry, vol. 272, No. 44, Oct. 31, 1997, pp. 27497-27500, The American Society for Biochemistry and Molecular Biology, Inc., USA.

Barak, L.S., et al., *Constitutive arrestin-mediated desensitization of a human vasopressin receptor mutant associated with nephrogenic diabetes insipidus*, Proceedings of the National Academy of Sciences, vol. 98, No. 1, Jan. 2, 2001, pp. 93-98, Proc.Natl. Acad. Sci, USA.

Barak, L.S., et al., *Internal Trafficking and Surface Mobility of a Functionally Intact $\beta_2$-Adrenergic Receptor-Green Fluorescent Protein Conjugate*, Molecular Pharmacology, 51, 1997, pp. 177-184.

Barak, L.S., et al., *Real-time Visualization of the Cellular Redistribution of G Protein-coupled Receptor Kinase 2 and β-arrestin 2 during Homologous Desensitization of the Substance P Receptor*, Journal of Biological Chemistry, vol. 274, No. 11, Mar. 12, 1999, pp. 7565-7569, The American Society for Biochemistry and Molecular Biology, Inc., USA.

*Current Protocols in Molecular Biology*, vol. 1, Section II, Supplement 24, 6.3.1-6.3.6, 1993, John Wiley & Sons, NY.

Drews, J., *Drug Discovery: A Historical Perspective*, Science, vol. 287, Mar. 17, 2000, pp. 1960-1964, American Association for the Advancement of Science, Washington, D.C.

(Continued)

*Primary Examiner*—Michael Pak
(74) *Attorney, Agent, or Firm*—Dorsey & Whitney; David J. Brezner; Michael F. Kolman

(57) ABSTRACT

The present invention relates to modified G-protein coupled receptors (GPCRs). The modified GPCRs of the present invention include GPCRs that have been modified to have altered DRY motifs such that the modified GPCRs are constitutively desensitized. As such, the modified GPCRs of the present invention preferably localize to endocytic vesicles or endosomes in an agonist-independent manner. The invention also relates to methods of screening compounds and sample solutions for GPCR activity using the modified GPCRs.

9 Claims, 27 Drawing Sheets

OTHER PUBLICATIONS

Ferguson, S.S.G., et al., *G-protein-coupled receptor regulation: role of G-protein-coupled receptor kinases and arrestins*, Can. J. Physiol. Pharmacol., vol. 74, 1996, pp. 1095-1110, NRC, Canada.

Ferguson, S.S.G., et al., *Role of Phosphorylation in Agonist-promoted $\beta_2$-Adrenergic Receptor Sequestration*, Journal of Biological Chemistry, vol. 270, No. 42, Oct. 20, 1995, pp. 24782-24789, The American Society for Biochemistry and Molecular Biology, Inc., USA.

Harada, A., et al., *Altered microtubule organization in small-calibre axons of mice lacking tau protein*, Nature, vol. 369, No. 6480, Jun. 9, 1994, Macmillian Magazines, Ltd., London.

Kim, K.-M., et al., *Differential Regulation of the Dopamine $D_2$ and $D_3$ Receptors by G Protein-coupled Receptor Kinases and $\beta$-arrestins*, Journal of Biological Chemistry, vol. 276 No. 40, Oct. 5, 2001, pp. 37409-97414, The American Society for Biochemistry and Molecular Biology, Inc., USA.

Laporte, S.A., et al. *The $\beta_2$-Adrenergic Receptor/ssarrestin complex recruits the Clathrin adaptor AP-2 during endocytosis*, Proceedings of the National Academy of Sciences, vol. 96, No. 7, Mar. 30, 1999, pp. 3712-3717, Proc.Natl. Acad. Sci, USA.

Laporte, S. A., et al., *The Interaction of $\beta$-Arrestin with the AP-2 Adaptor Is Required for the Clustering of $\beta_2$-Adrenergic Receptor into Clathin-coated Pits*, Journal of Biological Chemistry, vol. 275, No. 30, Jul. 28, 2000, pp. 23120-23126, The American Society for Biochemistry and Molecular Biology, Inc., USA.

Lohse, M., et al., *$\beta$-Arrestin: A Protein That Regulates $\beta$-Adrenergic Receptor Function*, Science, vol. 248, pp. 1547-1550, Jun. 22, 1990.

Ménard, L., et al., *Synergistic Regulation of $\beta_2$-Adrenergic Receptor Sequestration: Intracellular Complement of $\beta_2$-Adrenergic Receptor Kinase and ss-Arrestin Determine Kinetics of Internalization*, Molecular Pharmacology, vol. 51, No. 5, May 1997, pp. 800-808, The American Society for Pharmacology and Experimental Therapeutics.

Mhaouty-Kodja, S., et al., *Constitutively Active Alpha-1b Adrenergic Receptor Mutants Display Different Phosphorylation and Internalization Features*, Molecular Pharmacology, vol. 55, No. 2, Feb. 1999, pp. 339-347, The American Society for Pharmacology and Experimental Therapeutics.

Oakley, R.H., et al., *Association of $\beta$-Arrestin with G Protein-coupled Receptors During Clathrin-mediated Endocytosis Dictates the Profile of Receptor Resensitization*, Journal of Biological Chemistry, vol. 274, No. 45, Nov. 5, 1999, pp. 32248-32257, The American Society for Biochemistry and Molecular Biology, Inc., USA.

Oakley, R.H., et al., *Differential Affinities of Visual Arrestin, $\beta$-Arrestin1, and $\beta$-Arrestin2 for G Protein-coupled Receptors Delineate Two Major Classes of Receptors*, Journal of Biological Chemistry, vol. 275, No. 22, Jun. 2, 2000, pp. 17201-17210, The American Society for Biochemistry and Molecular Biology, Inc., USA.

Oakley, R.H., et al., *Molecular Determinatnts Underlying the Formation of Stable Intracellular G Protein-coupled Receptor—$\beta$-Arrestin Complexes after Receptor Endocytosis*, Journal of Biological Chemistry, vol. 276, No. 22, Jun. 1, 2001, pp. 19452-19460, The American Society for Biochemistry and Molecular Biology, Inc., USA.

Probst, W.C., et al., *Sequence Alignment of the G-Protein Coupled Receptor of Superfamily*, DNA and Cell Biology, vol. 11, No. 1, Jan. & Feb. 1992, pp. 1-20, Mary Ann Liebert, Inc. Publishers.

Sadeghi, H.M., et al., *Maturation of Receptor Proteins in Eukaryotic Expression Systems*, Journal of Receptor & Signal Transduction Research, vol. 17, No. 1-3, 1997, pp. 433-445, Marcel Dekker, Inc., USA.

Sadeghi, H., et al., *O-Glycosylation of the V2 vasopressin receptor*, Glycobiology, vol. 9, No. 7, pp. 731-737, 1999, Oxford University Press, Printed by the Sharidan Press, USA.

Schöneberg, T., et al., *Functional rescue of mutant V2 vasopressin receptors causing nephrogenic diabetes insipidus by a co-expressed receptor polypeptide*, Embo Journal, vol. 15, No. 6, pp. 1283-1291, 1996, Oxford University Press.

Schöneberg, T., et al., *V2 Vasopressin Receptor Dysfunction in Nephrogenic Diabetes Insipidus Caused by Different Molecular Mechanisms*, Human Mutation, vol. 12, No. 3, pp. 196-205, 1998, Willey-Lisa, Inc.

Shi, W., et al., *Rhodopsin Arginine-135 Mutants Are Phosphorylated by Rhodopsin Kinase and Bind Arrestin in the Absence of 11-cis-Retinal*, Biochemistry, vol. 37, pp. 4869-4874, 1998, American Chemical Society, Washington, D.C.

Zhang, J., et al., *Cellular Trafficking of G Protein-coupled Receptor/$\beta$-Arrestin Endocytic Complexes*, Journal of Biological Chemistry, vol. 274, No. 16, Apr. 16, 1999, pp. 10999-11006, The American Society for Biochemistry and Molecular Biology, Inc., USA.

Zhang, J., et al., *A Central Role for ss-Arrestins and Clathin-coated Vesicle-mediated Endocytosis in $\beta_2$-Adrenergic Receptor Resensitization*, Journal of Biological Chemistry, vol. 272, No. 43, Oct. 24, 1997, pp. 27005-27014, The American Society for Biochemistry and Molecular Biology, Inc., USA.

Birnbaumer, Mariel, et al., "Molecular Cloning of the Receptor for Human Antidiuretic Hormone", Nature, vol. 357, No. 6376, pp. 333-335 (1992).

Rosenthal, Walter, et al., "Nephrogenic Diabetes Insipidus: A V2 Vasopressin Receptor Unable to Stimulate Adenylyl Cyclase", Journal of Biological Chemistry, vol. 268, No. 18, pp. 13030-13033 (1993).

Siegl, Peter K. S., et al., "In Vivo Pharmacology of L-158,809, a New Highly Potent and Selective Nonpeptide Angiotensin II Receptor Antagonist", Journal of Pharmacology and Experimental Therapeutics, vol. 262, No. 1, pp. 139-144 (Jul. 1, 1992).

FIG. 1A

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I | | | | | |
| Rhodopsin like | | | | | |
| | •Amine | | | | |
| | •Acetylcholine (muscarinic & nicotinic) | 5 | Brain, Nerves, Heart | Neurotransmitter | Acuity, Alzheimer's |
| | •Adrenoceptors | | | | |
| | •Alpha Adrenoceptors | 6 | Brain, Kidney, Lung | Gluconeogenesis | Diabetes, Cardiovascular |
| | •Beta Adrenoceptors | 3 | Kidney, Heart | Muscle Contraction | Cardiovascular, Respiratory |
| | •Dopamine | 5 | Brain, Kidney, GI | Neurotransmitter | Cardiovascular, Parkinson's |
| | •Histamine | 2 | Vascular, Heart, Brain | Vascular Permeability | Anti-inflammatory, Ulcers |
| | •Serotonin (5-HT) | 16 | Most Tissues | Neurotransmitter | Depression, Insomnia, Analgesic |
| | •Peptide | | | | |
| | •Angiotensin | 2 | Vascular, Liver, Kidney | Vasoconstriction | Cardiovascular, Endocrine |
| | •Bradykinin | 1 | Liver, Blood | Vasodilation, | Anti-inflammatory, Asthma |
| | •C5a anaphylatoxin | 1 | Blood | Immune System | Anti-inflammatory |
| | •Fmet-leu-phe | 3 | Blood | Chemoattractant | Anti-inflammatory |
| | •Interleukin-8 | 1 | Blood | Chemoattractant | Anti-inflammatory |
| | •Chemokine | 6 | Blood | Chemoattractant | Anti-inflammatory |
| | •Orexin | 2 | Brain | Fat Metabolism | Obesity |
| | •Nociceptin | 1 | Brain | Bronchodilator, Pain | Airway Diseases, Anesthetic |
| | •CCK (Gastrin) | 2 | Gastrointestinal | Motility, Fat Absorption | Gastrointestinal, Obesity, Parkinson's |
| | •Endothelin | 2 | Heart, Bronchus, Brain | Muscle Contraction | Cardiovascular, Respiratory |
| | •Melanocortin | 5 | Kidney, Brain | Metabolic Regulation | Anti-inflammatory, Analgesics |
| | •Neuropeptide Y | 5 | Nerves, Intestine, Blood | Neurotransmitter | Behavior, Memory, Cardiovascular |
| | •Neurotensin | 1 | Brain, | CNS | Cardiovascular, Analgesic |
| | •Opioid | 3 | Brain, | CNS | Depression, Analgesic |
| | •Somatostatin | 5 | Brain, Gastrointestinal | Neurotransmitter | Oncology, Alzheimer's |

FIG. 1B

| | | | |
|---|---|---|---|
| •Tachykinin (Substance P, NKA₁) | 3 | Brain Nerves | Neurohormone | Depression, Analgesic |
| •Thrombin | 3 | Platelets, Blood Vessels | Coagulation | Anti-coagulant, Anti-inflammatory |
| •Vasopressin-like | 4 | Arteries, Heart, Bladder | Water Balance | Anti-diuretic, Diabetic Complications |
| •Galanin | 1 | Brain, Pancreas | Neurotransmitter | Analgesics, Alzheimer's |
| •Hormone protein | | | | |
| •Follicle stimulating hormone | 1 | Ovary, Testis | Endocrine | Infertility |
| •Lutropin-choriogonadotropic | 1 | Ovary, Testis | Endocrine | Infertility |
| •Thyrotropin | 1 | Thyroid | Endocrine | Thyroidism, Metabolism |
| •(Rhod)opsin | | | | |
| •Opsin | 5 | Eye | Photoreception | Ophthalmic Diseases |
| •Olfactory | 4 (~1000) | Nose | Smell | Olfactory Diseases |
| •Prostanoid | | | | |
| •Prostaglandin | 5 | Arterial, Gastrointestinal Vessels, Heart, Lung | Vasodilation, Pain | Cardiovascular, Analgesic |
| •Lysophosphatidic Acid | 2 | Most Cells | Inflammation | Cancer, Anti-Inflammatory |
| •Sphingosine-1-phosphate | 2 | White Blood Cells, Bronchus | Cell proliferation | Cancer |
| •Leukotriene | 1 | | | |
| •Prostacyclin | 1 | Arterial, Gastrointestinal | Inflammation | Asthma, Rheumatoid Arthritis |
| •Thromboxane | 1 | Arterial, Bronchus | Platelet Regulation | Cardiovascular |
| | | | Vasoconstriction | Cardiovascular, Respiratory |
| •Nucleotide-like | | | | |
| •Adenosine | 4 | Vascular, Bronchus | Multiple Effects | Cardiovascular, Respiratory |
| •Purinoceptors | 4 | Vascular, Platelets | Relaxes Muscle | Cardiovascular, Respiratory |
| •Cannabis | 2 | Brain | Sensory Perception | Analgesics, Memory |
| •Platelet activating factor | 1 | Most Peripheral Tissues | Inflammation | Anti-inflammatory, Anti-asthmatic |
| •Gonadotropin-releasing hormone like | | | | |
| •Gonadotropin-releasing hormone | 1 | Reproductive Organs, Pituitary | Reproduction | Prostate Cancer, Endometriosis |
| •Thyrotropin-releasing hormone | 1 | Pituitary, Brain | Thyroid Regulation | Metabolic Regulation |
| •Growth hormone-inhibiting factor | 1 | Gastrointestinal | Neuroendocrine | Oncology, Alzheimer's |
| •Melatonin | 1 | Brain, Eye, Pituitary | Neuroendocrine | Regulation of Circadian Cycle |

FIG. 1C

- Class II
- Secretin like
  - Secretin — 1 — Gastrointestinal, Heart — Digestion — Obesity, Gastrointestinal
  - Calcitonin — 1 — Bone, Brain — Calcium Resorption — Osteoporosis
  - Corticotropin releasing factor/urocortin — 1 — Adrenal, Vascular, Brain — Neuroendocrine — Stress, Mood, Obesity
  - Gastric inhibitory peptide (GIP) — 1 — Adrenals, Fat Cells — Sugar/Fat Metabolism — Diabetes, Obesity
  - Glucagon — 1 — Liver, Fat Cells, Heart — Gluconeogenesis — Cardiovascular
  - Glucagon-like Peptide 1 (GLP-1) — 1 — Pancreas, Stomach, Lung — Gluconeogenesis — Cardiovascular, Diabetes, Obesity
  - Growth hormone-releasing hormone — 1 — Brain — Neuroendocrine — Growth Regulation
  - Parathyroid hormone — 1 — Bone, Kidney — Calcium Regulation — Osteoporosis
  - PACAP — 1 — Brain, Pancreas, Adrenals — Metabolism — Metabolic Regulation
  - Vasoactive intestinal polypeptide (VIP) — 1 — Gastrointestinal — Motility — Gastrointestinal
- Class III
  - Metabotropic Glutamate — 7 — Brain — Sensory Perception — Hearing, Vision
  - GABA$_B$ — 1 — Brain — Neurotransmitter — Mood Disorders
  - Extracellular Calcium Sensing — 1 — Parathyroid, Kidney, GI Tract — Calcium Regulation — Cataracts, GI Tumors

FIG. 2

(a)
Wild-type DRY motif
D = may also be, preferably, E, L, P, Q, T, I, C, G, N, V, H, or A.
Y = may also be, preferably, W, F, S, I, Q, H, G, C, L, D, or A.
R = may also be, preferably, H, or C, or another amino acid, wherein GPCR is not constitutively desensitized (b)
Modified DRY motif
$2^{nd}$ amino acid = any amino acid other than R or K, preferably A, D, E, N, and H.

FIG. 3A

The mutated amino acid at the second position of the DRY motif is underlined.

VASOPRESSIN V2 RECEPTOR - (Human)
accession P30518

R137H

```
  1 MLMASTTSAV PGHPSLPSLP SNSSQERPLD TRDPLLARAE LALLSIVFVA VALSNGLVLA
 61 ALARRGRRGH WAPIHVFIGH LCLADLAVAL FQVLPQLAWK ATDRFRGPDA LCRAVKYLQM
121 VGMYASSYMI LAMTLDHHRA ICRPMLAYRH GSGAHWNRPV LVAWAFSLLL SLPQLFIFAQ
181 RNVEGGSGVT DCWACFAEPW GRRTYVTWIA LMVFVAPTLG IAACQVLIFR EIHASLVPGP
241 SERPGGRRRG RRTGSPGEGA HVSAAVAKTV RMTLVIVVVY VLCWAPFFLV QLWAAWDPEA
301 PLEGAPFVLL MLLASLNSCT NPWIYASFSS SVSSELRSLL CCARGRTPPS LGPQDESCTT
361 ASSSLAKDTS S
```
(SEQ ID NO:1)

FIG. 3B

ALPHA-1B ADRENERGIC RECEPTOR (ALPHA 1B-ADRENOCEPTOR).
(Golden hamster)
ACCESSION P18841
R143E

```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDEYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:2)

R143A

```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDAYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:3)

R143H
```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDHYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:4)

R143N
```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDNYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:5)

FIG. 3C angiotensin II receptor, type 1 (AT1A) [Rattus norvegicus].
ACCESSION NP_112247

R126H

```
  1 MALNSSAEDG IKRIQDDCPK AGRHSYIFVM IPTLYSIIFV VGIFGNSLVV IVIYFYMKLK
 61 TVASVFLLNL ALADLCFLLT CPLWAVYTAM EYRWPFGNHL CKIASASVTF NLYASVFLLT
121 CLSIDHYLAI VHPMKSRLRR TMLVAKVTCI IIWLMAGLAS LPAVIHRNVY FIENTNITVC
181 AFHYESRNST LPIGLGLTKN ILGFLFPFLI ILTSYTLIWK ALKKAYEIQK NKPRNDDIFR
241 IIMAIVLFFF FSWVPHQIFT FLDVLIQLGV IHDCKISDIV DTAMPITICI AYFNNCLNPL
301 FYGFLGKKFK KYFLQLLKYI PPKAKSHSSL STKMSTLSYR PSDNMSSSAK KPASCFEVE
```
(SEQ ID NO:6)

Rhodamine Anti-HA Labeling

βarrestin-GFP Distribution

βarrestin-GFP in the presence of dynamin(k44A)

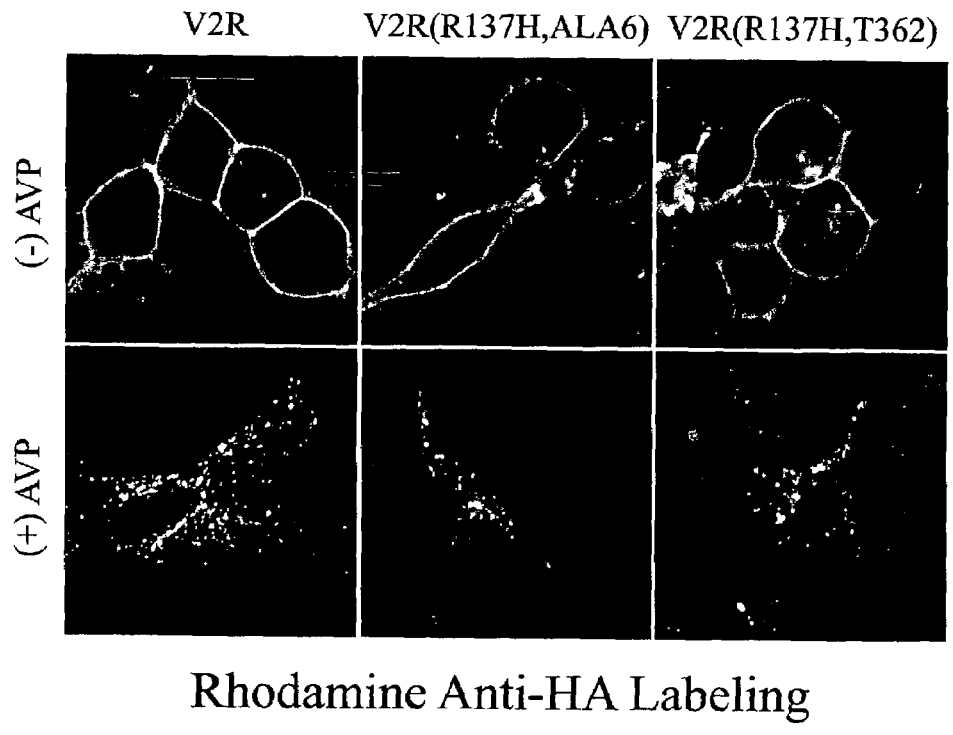
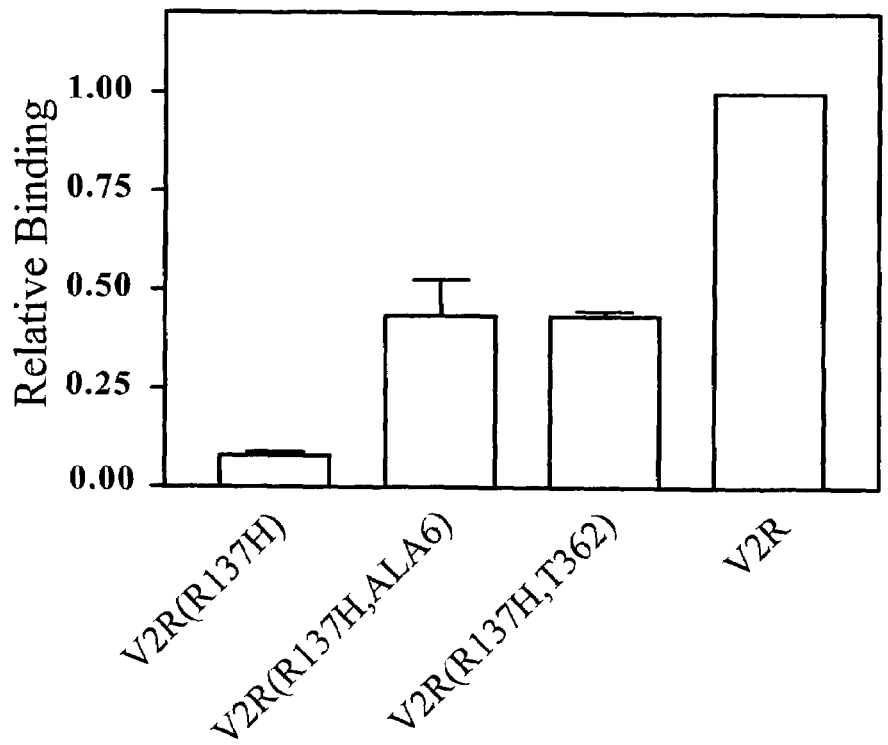

βarrestin-GFP Distribution

αHA-FITC

Receptor-GFP distribution

βarrestin-GFP distribution

Receptor-GFP distribution

Receptor-GFP Distribution

βarrestin-GFP Distribution

βarrestin-GFP distribution

Fig. 17A

Homo sapiens arginine vasopressin receptor 2
ACCESSION NM_000054

R137H atgct
6 catggcgtcc accacttccg ctgtgcctgg gcatccctct ctgcccagcc tgcccagcaa
66 cagcagccag gagaggccac tggacacccg ggacccgctg ctagcccggg cggagctggc
126 gctgctctcc atagtctttg tggctgtggc cctgagcaat ggcctggtgc tggcggccct
186 agctcggcgg ggccggcggg gccactgggc acccatacac gtcttcattg ccacttgtg
246 cctggccgac ctggccgtgg ctctgttcca agtgctgccc cagctggcct ggaaggccac
306 cgaccgcttc cgtgggccag atgccctgtg tcgggccgtg aagtatctgc agatggtggg
366 catgtatgcc tcctcctaca tgatcctggc catgacgctg gaccaccacc gtgccatctg
426 ccgtcccatg ctggcgtacc gccatggaag tgggctcac tggaaccggc cggtgctagt
486 ggcttgggcc ttctcgctcc ttctcagcct gcccagctc ttcatcttcg cccagcgcaa
546 cgtggaaggt ggcagcgggg tcactgactg ctgggcctgc tttgcggagc cctggggccg
606 tcgcacctat gtcacctgga ttgccctgat ggtgttcgtg gcacctaccc tgggtatcgc
666 cgcctgccag gtgctcatct tccgggagat tcatgccagt ctggtgccag ggccatcaga
726 gaggcctggg gggcgccgca ggggacgccg gacaggcagc cccggtgagg gagcccacgt
786 gtcagcagct gtggccaaga ctgtgaggat gacgctagtg attgtggtcg tctatgtgct
846 gtgctgggca cccttcttcc tggtgcagct gtgggccgcg tgggacccgg aggcacctct
906 ggaagggggcg ccctttgtgc tactcatgtt gctggccagc ctcaacagct gcaccaaccc
966 ctggatctat gcatctttca gcagcagcgt gtcctcagag ctgcgaagct tgctctgctg
1026 tgcccgggga cgcacccac ccagcctggg tccccaagat gagtcctgca ccaccgccag
1086 ctcctccctg gccaaggaca cttcatcgtg a
(SEQ ID NO:7)

FIG. 17B

Syrian golden hamster alpha-1B adrenergic receptor mRNA
ACCESSION J04084

R143H
        1 atgaat cccgatctgg acaccggcca caacacatca gcacctgccc
       47 aatggggaga gttgaaagat gccaacttca ctggccccaa ccagacctcg agcaactcca
      107 cactgcccca gctggacgtt accagggcca tctctgtggg cctggtgctg ggcgccttca
      167 tcctctttgc cattgtgggc aacatcctgg tcatcctgtc agtggcctgc aatcggcacc
      227 tgcggacgcc caccaactac ttcattgtca acctggccat tgctgacctg ctgttgagtt
      287 tcacagtcct gcccttctcc gctaccctag aagtgcttgg ctactgggtt ctggggcgca
      347 tcttctgtga catctgggca gcggtggacg tcctgtgctg tacggcctcc atcctgagcc
      407 tatgtgccat ctccattgat cactacattg gggtgcgcta ctctctgcag tacccactc
      467 tggtcacccg caggaaggcc atcttggcac tcctcagtgt gtgggttttg tccacggtca
      527 tctccatcgg gcctctcctt ggatggaaag aaccagcgcc caacgacgac aaggaatgcg
      587 gagtcaccga gaaccctc tatgccctct tttcctccct gggctccttc tacatcccac
      647 tcgcggtcat tctggtcatg tactgccggg tctacatcgt ggccaagagg accaccaaga
      707 acctggaggc tggagtcatg aaggagatgt ccaactccaa ggagctgacc ctgaggatcc
      767 actccaagaa ctttcatgag gacaccctca gcagtaccaa ggccaagggc cacaaccca
      827 ggagttccat agctgtcaaa cttttaagt tctccaggga aagaaagca gccaaaacct
      887 tgggcattgt ggtcggaatg ttcatcttgt gttggctccc cttcttcatc gctctcccac
      947 ttggctccct gttctccact ctcaagcccc cggacgccgt gttcaaggtg gtattctggc
     1007 tgggctactt caacagctgc ctcaacccca tcatctaccc gtgctccagc aaggagttca
     1067 agcgcgcctt catgcgtatc cttgggtgcc agtgccgtag tggccgtcgc cgccgccgcc
     1127 gccgtcgtct gggcgcgtgc gcttacacct atcggccgtg gacgcgcggc ggctcgctgg
     1187 agcgatcgca gtcgcggaag gactccctgg acgacagcgg cagctgcatg agtggcagcc
     1247 agaggaccct gccctcggcg tcgcccagcc cgggctacct gggtcgcgga gcgcagccac 1307 cactggagct gtgcgcctac cccgaatgga aatccggggc tctgctcagt ctgccagagc
1367 ctccgggtcg ccgcggtcgc ctcgactctg ggcccctctt cactttcaag ctcttgggag
1427 agccggagag cccgggcacc gagggcgatg ccagcaatgg gggctgcgac gcaacgaccg
1487 acctggccaa tgggcagccc ggtttcaaga gcaacatgcc tctggcaccc gggcactttt
1547 ag
(SEQ ID NO:8)

FIG. 17C

R143A
    1 atgaat cccgatctgg acaccggcca caacacatca gcacctgccc
   47 aatggggaga gttgaaagat gccaàcttca ctggccccaa ccagacctcg agcaactcca
  107 cactgcccca gctggacgtt accagggcca tctctgtggg cctggtgctg ggcgccttca
  167 tcctctttgc cattgtgggc aacatcctgg tcatcctgtc agtggcctgc aatcggcacc
  227 tgcggacgcc caccaactac ttcattgtca acctggccat tgctgacctg ctgttgagtt
  287 tcacagtcct gcccttctcc gctaccctag aagtgcttgg ctactgggtt ctggggcgca
  347 tcttctgtga catctgggca gcggtggacg tcctgtgctg tacggcctcc atcctgagcc
  407 tatgtgccat ctccattgat gcctacattg gggtgcgcta ctctctgcag taccccactc
  467 tggtcacccg caggaaggcc atcttggcac tcctcagtgt gtgggttttg tccacggtca
  527 tctccatcgg gcctctcctt ggatggaaag aaccagcgcc caacgacgac aaggaatgcg
  587 gagtcaccga agaacccttc tatgccctct ttcctccct gggctccttc tacatcccac
  647 tcgcggtcat tctggtcatg tactgccggg tctacatcgt ggccaagagg accaccaaga
  707 acctggaggc tggagtcatg aaggagatgt ccaactccaa ggagctgacc ctgaggatcc
  767 actccaagaa ctttcatgag gacaccctca gcagtaccaa ggccaagggc cacaacccca
  827 ggagttccat agctgtcaaa ctttttaagt ctccaggga aaagaaagca gccaaaacct
  887 tgggcattgt ggtcggaatg ttcatcttgt gttggctccc cttcttcatc gctctcccac
  947 ttggctcct gttctccact ctcaagcccc cggacgccgt gttcaaggtg gtattctggc
 1007 tgggctactt caacagctgc ctcaacccca tcatctaccc

```
gtgctccagc aaggagttca
    1067 agcgcgcctt catgcgtatc cttgggtgcc agtgccgtag
tggccgtcgc cgccgccgcc
    1127 gccgtcgtct gggcgcgtgc gcttacacct atcggccgtg
gacgcgcggc ggctcgctgg
    1187 agcgatcgca gtcgcggaag gactccctgg acgacagcgg
cagctgcatg agtggcagcc
    1247 agaggaccct gccctcggcg tcgcccagcc cgggctacct
gggtcgcgga gcgcagccac
    1307 cactggagct gtgcgcctac cccgaatgga aatccggggc
tctgctcagt ctgccagagc
    1367 ctccgggtcg ccgcggtcgc ctcgactctg ggcccctctt
cactttcaag ctcttgggag
    1427 agccggagag cccgggcacc gagggcgatg ccagcaatgg
gggctgcgac gcaacgaccg
    1487 acctggccaa tgggcagccc ggtttcaaga gcaacatgcc
tctggcaccc gggcactttt
    1547 ag
(SEQ ID NO:9)
```

FIG. 17D

```
R143E
       1 atgaat cccgatctgg acaccggcca caacacatca
gcacctgccc
      47 aatggggaga gttgaaagat gccaacttca ctggccccaa
ccagacctcg agcaactcca
     107 cactgcccca gctggacgtt accagggcca tctctgtggg
cctggtgctg ggcgccttca
     167 tcctctttgc cattgtgggc aacatcctgg tcatcctgtc
agtggcctgc aatcggcacc
     227 tgcggacgcc caccaactac ttcattgtca acctggccat
tgctgacctg ctgttgagtt
     287 tcacagtcct gcccttctcc gctaccctag aagtgcttgg
ctactgggtt ctggggcgca
     347 tcttctgtga catctgggca gcggtggacg tcctgtgctg
tacggcctcc atcctgagcc
     407 tatgtgccat ctccattgat gagtacattg gggtgcgcta
ctctctgcag taccccactc
     467 tggtcacccg caggaaggcc atcttggcac tcctcagtgt
gtgggttttg tccacggtca
     527 tctccatcgg gcctctcctt ggatggaaag aaccagcgcc
caacgacgac aaggaatgcg
     587 gagtcaccga agaacccttc tatgccctct tttcctccct
gggctccttc tacatcccac
     647 tcgcggtcat tctggtcatg tactgccggg tctacatcgt
ggccaagagg accaccaaga
     707 acctggaggc tggagtcatg aaggagatgt ccaactccaa
```
ggagctgacc ctgaggatcc
    767 actccaagaa ctttcatgag gacaccctca gcagtaccaa ggccaagggc cacaacccca
    827 ggagttccat agctgtcaaa ctttttaagt tctccaggga aaagaaagca gccaaaacct
    887 tgggcattgt ggtcggaatg ttcatcttgt gttggctccc cttcttcatc gctctcccac
    947 ttggctccct gttctccact ctcaagcccc cggacgccgt gttcaaggtg gtattctggc
   1007 tgggctactt caacagctgc ctcaacccca tcatctaccc gtgctccagc aaggagttca
   1067 agcgcgcctt catgcgtatc cttgggtgcc agtgccgtag tggccgtcgc cgccgccgcc
   1127 gccgtcgtct gggcgcgtgc gcttacacct atcggccgtg gacgcgcggc ggctcgctgg
   1187 agcgatcgca gtcgcggaag gactccctgg acgacagcgg cagctgcatg agtggcagcc
   1247 agaggaccct gccctcggcg tcgcccagcc cgggctacct gggtcgcgga gcgcagccac
   1307 cactggagct gtgcgcctac cccgaatgga aatccggggc tctgctcagt ctgccagagc
   1367 ctccgggtcg ccgcggtcgc ctcgactctg ggcccctctt cactttcaag ctcttgggag
   1427 agccggagag cccgggcacc gagggcgatg ccagcaatgg gggctgcgac gcaacgaccg
   1487 acctggccaa tgggcagccc ggtttcaaga gcaacatgcc tctggcaccc gggcactttt
   1547 ag
(SEQ ID NO:10)

FIG. 17E

R143N
    1 atgaat cccgatctgg acaccggcca caacacatca gcacctgccc
   47 aatggggaga gttgaaagat gccaacttca ctggccccaa ccagacctcg agcaactcca
  107 cactgcccca gctggacgtt accagggcca tctctgtggg cctggtgctg ggcgccttca
  167 tcctctttgc cattgtgggc aacatcctgg tcatcctgtc agtggcctgc aatcggcacc
  227 tgcggacgcc caccaactac ttcattgtca acctggccat tgctgacctg ctgttgagtt
  287 tcacagtcct gccctttctcc gctaccctag aagtgcttgg ctactgggtt ctgggcgca
  347 tcttctgtga catctgggca gcggtggacg tcctgtgctg tacggcctcc atcctgagcc
  407 tatgtgccat ctccattgat aactacattg gggtgcgcta ctctctgcag taccccactc

FIG. 17E (continued)

```
    467 tggtcacccg caggaaggcc atcttggcac tcctcagtgt
gtgggttttg tccacggtca
    527 tctccatcgg gcctctcctt ggatggaaag aaccagcgcc
caacgacgac aaggaatgcg
    587 gagtcaccga agaacccttc tatgccctct tttcctccct
gggctccttc tacatcccac
    647 tcgcggtcat tctggtcatg tactgccggg tctacatcgt
ggccaagagg accaccaaga
    707 acctggaggc tggagtcatg aaggagatgt ccaactccaa
ggagctgacc ctgaggatcc
    767 actccaagaa ctttcatgag gacaccctca gcagtaccaa
ggccaagggc cacaacccca
    827 ggagttccat agctgtcaaa cttttaagt tctccaggga
aaagaaagca gccaaaacct
    887 tgggcattgt ggtcggaatg ttcatcttgt gttggctccc
cttcttcatc gctctcccac
    947 ttggctccct gttctccact ctcaagcccc cggacgccgt
gttcaaggtg gtattctggc
    1007 tgggctactt caacagctgc ctcaacccca tcatctaccc
gtgctccagc aaggagttca
    1067 agcgcgcctt catgcgtatc cttgggtgcc agtgccgtag
tggccgtcgc cgccgccgcc
    1127 gccgtcgtct gggcgcgtgc gcttacacct atcggccgtg
gacgcgcggc ggctcgctgg
    1187 agcgatcgca gtcgcggaag gactccctgg acgacagcgg
cagctgcatg agtggcagcc
    1247 agaggaccct gccctcggcg tcgcccagcc cgggctacct
gggtcgcgga gcgcagccac
    1307 cactggagct gtgcgcctac cccgaatgga aatccggggc
tctgctcagt ctgccagagc
    1367 ctccgggtcg ccgcggtcgc ctcgactctg ggcccctctt
cactttcaag ctcttgggag
    1427 agccggagag cccgggcacc gagggcgatg ccagcaatgg
gggctgcgac gcaacgaccg
    1487 acctggccaa tggcagccc ggtttcaaga gcaacatgcc
tctggcaccc gggcactttt
    1547 ag
(SEQ ID NO:11)
```

FIG. 17F

Rattus norvegicus Angiotensin II receptor, type 1 (AT1AR)
ACCESSION NM_030985

R126H
1 a tggcccttaa ctcttctgct gaagatggta tcaaaagaat
    42 ccaagatgac tgccccaagg ctggcaggca cagttacata tttgtcatga tccctaccct
    102 ctacagcatc atctttgtgg tgggaatatt tggaaacagc ttggtggtga ttgtcattta
    162 cttttacatg aagctgaaga ctgtggccag cgtctttctt ctcaatctcg ccttggctga
    222 cttatgcttt ttgctgactt gtcccctgtg ggcagtctat accgctatgg agtaccgctg
    282 gcccttcggc aatcacctat gtaagatcgc ttcggccagc gtgacgttca acctctacgc
    342 cagtgtgttc cttctcacgt gtctcagcat cgacc<u>a</u>ctac ctggccatcg tccacccaat
    402 gaagtctcgc cttcgccgca cgatgctggt ggccaaagtc acctgcatca tcatctggct
    462 gatggctggc ttggccagtt tgccagctgt catccaccga aatgtatact tcatcgagaa
    522 caccaatatc acagtgtgcg cgtttcatta tgagtctcgg aattcgacgc tccccatagg
    582 gctgggcctt accaagaata ttctgggctt cttgttccct ttccttatca ttctcaccag
    642 ctataccctt atttggaaag ctctaaagaa ggcttatgaa attcaaaaga acaaaccaag
    702 aaacgatgac atctttagga taattatggc gattgtgctt ttcttcttct tttcctgggt
    762 cccccaccaa atattcactt cctggatgt gctgattcag ctgggcgtca tccatgactg
    822 taaaatttct gacatcgtgg acactgccat gcccatcacc atctgcatag cgtattttaa
    882 caactgcctg aaccctctgt tctacggctt tctggggaag aaatttaaaa agtatttcct
    942 ccagctcctg aaatatattc ccccaaaggc caagtcccac tcaagcctgt ctacgaaaat
    1002 gagcacgctt tcttaccggc cttcggataa catgagctca tcggccaaaa agcctgcgtc
    1062 ttgttttgag gtggagtga
(SEQ ID NO:12)

SEQUENCE LISTING

```
<160> NUMBER OF SEQ ID NOS: 12

<210> SEQ ID NO 1
<211> LENGTH: 371
<212> TYPE: PRT
<213> ORGANISM: Homo sapiens

<400> SEQUENCE: 1

Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
            20                  25                  30

Asp Pro Leu Leu Ala Arg Ala Glu Leu Ala Leu Leu Ser Ile Val Phe
        35                  40                  45

Val Ala Val Ala Leu Ser Asn Gly Leu Val Leu Ala Ala Leu Ala Arg
    50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
        115                 120                 125

Met Ile Leu Ala Met Thr Leu Asp His His Arg Ala Ile Cys Arg Pro
    130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190
```

```
Trp Ala Cys Phe Ala Glu Pro Trp Gly Arg Arg Thr Tyr Val Thr Trp
        195                 200                 205

Ile Ala Leu Met Val Phe Val Ala Pro Thr Leu Gly Ile Ala Ala Cys
    210                 215                 220

Gln Val Leu Ile Phe Arg Glu Ile His Ala Ser Leu Val Pro Gly Pro
225                 230                 235                 240

Ser Glu Arg Pro Gly Arg Arg Gly Arg Arg Thr Gly Ser Pro
            245                 250                 255

Gly Glu Gly Ala His Val Ser Ala Ala Val Ala Lys Thr Val Arg Met
            260                 265                 270

Thr Leu Val Ile Val Val Val Tyr Val Leu Cys Trp Ala Pro Phe Phe
    275                 280                 285

Leu Val Gln Leu Trp Ala Ala Trp Asp Pro Glu Ala Pro Leu Glu Gly
    290                 295                 300

Ala Pro Phe Val Leu Leu Met Leu Leu Ala Ser Leu Asn Ser Cys Thr
305                 310                 315                 320

Asn Pro Trp Ile Tyr Ala Ser Phe Ser Ser Ser Val Ser Ser Glu Leu
                325                 330                 335

Arg Ser Leu Leu Cys Cys Ala Arg Gly Arg Thr Pro Pro Ser Leu Gly
            340                 345                 350

Pro Gln Asp Glu Ser Cys Thr Thr Ala Ser Ser Ser Leu Ala Lys Asp
            355                 360                 365

Thr Ser Ser
    370

<210> SEQ ID NO 2
<211> LENGTH: 515
<212> TYPE: PRT
<213> ORGANISM: Golden hamster

<400> SEQUENCE: 2

Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
            20                  25                  30

Ser Asn Ser Thr Leu Pro Gln Leu Asp Val Thr Arg Ala Ile Ser Val
        35                  40                  45

Gly Leu Val Leu Gly Ala Phe Ile Leu Phe Ala Ile Val Gly Asn Ile
    50                  55                  60

Leu Val Ile Leu Ser Val Ala Cys Asn Arg His Leu Arg Thr Pro Thr
65                  70                  75                  80

Asn Tyr Phe Ile Val Asn Leu Ala Ile Ala Asp Leu Leu Leu Ser Phe
                85                  90                  95

Thr Val Leu Pro Phe Ser Ala Thr Leu Glu Val Leu Gly Tyr Trp Val
                100                 105                 110

Leu Gly Arg Ile Phe Cys Asp Ile Trp Ala Ala Val Asp Val Leu Cys
            115                 120                 125

Cys Thr Ala Ser Ile Leu Ser Leu Cys Ala Ile Ser Ile Asp Glu Tyr
    130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
                180                 185                 190
```

```
Lys Glu Cys Gly Val Thr Glu Pro Phe Tyr Ala Leu Phe Ser Ser
            195                 200                 205

Leu Gly Ser Phe Tyr Ile Pro Leu Ala Val Ile Leu Val Met Tyr Cys
        210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
            245                 250                 255

Ser Lys Asn Phe His Glu Asp Thr Leu Ser Ser Thr Lys Ala Lys Gly
        260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
            290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
            325                 330                 335

Gly Tyr Phe Asn Ser Cys Leu Asn Pro Ile Ile Tyr Pro Cys Ser Ser
        340                 345                 350

Lys Glu Phe Lys Arg Ala Phe Met Arg Ile Leu Gly Cys Gln Cys Arg
            355                 360                 365

Ser Gly Arg Arg Arg Arg Arg Arg Arg Leu Gly Ala Cys Ala Tyr
        370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
            405                 410                 415

Arg Thr Leu Pro Ser Ala Ser Pro Ser Pro Gly Tyr Leu Gly Arg Gly
        420                 425                 430

Ala Gln Pro Pro Leu Glu Leu Cys Ala Tyr Pro Glu Trp Lys Ser Gly
        435                 440                 445

Ala Leu Leu Ser Leu Pro Glu Pro Pro Gly Arg Arg Gly Arg Leu Asp
450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
            485                 490                 495

Leu Ala Asn Gly Gln Pro Gly Phe Lys Ser Asn Met Pro Leu Ala Pro
        500                 505                 510

Gly His Phe
        515

<210> SEQ ID NO 3
<211> LENGTH: 515
<212> TYPE: PRT
<213> ORGANISM: Golden hamster

<400> SEQUENCE: 3

Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
            20                  25                  30

Ser Asn Ser Thr Leu Pro Gln Leu Asp Val Thr Arg Ala Ile Ser Val
```

-continued

```
             35                  40                  45
Gly Leu Val Leu Gly Ala Phe Ile Leu Phe Ala Ile Val Gly Asn Ile
 50                  55                  60
Leu Val Ile Leu Ser Val Ala Cys Asn Arg His Leu Arg Thr Pro Thr
 65                  70                  75                  80
Asn Tyr Phe Ile Val Asn Leu Ala Ile Ala Asp Leu Leu Leu Ser Phe
                 85                  90                  95
Thr Val Leu Pro Phe Ser Ala Thr Leu Glu Val Leu Gly Tyr Trp Val
                100                 105                 110
Leu Gly Arg Ile Phe Cys Asp Ile Trp Ala Ala Val Asp Val Leu Cys
                115                 120                 125
Cys Thr Ala Ser Ile Leu Ser Leu Cys Ala Ile Ser Ile Asp Ala Tyr
                130                 135                 140
Ile Gly Val Arg Tyr Ser Leu Gln Tyr Pro Thr Leu Val Thr Arg Arg
145                 150                 155                 160
Lys Ala Ile Leu Ala Leu Leu Ser Val Trp Val Leu Ser Thr Val Ile
                165                 170                 175
Ser Ile Gly Pro Leu Leu Gly Trp Lys Glu Pro Ala Pro Asn Asp Asp
                180                 185                 190
Lys Glu Cys Gly Val Thr Glu Glu Pro Phe Tyr Ala Leu Phe Ser Ser
                195                 200                 205
Leu Gly Ser Phe Tyr Ile Pro Leu Ala Val Ile Leu Val Met Tyr Cys
                210                 215                 220
Arg Val Tyr Ile Val Ala Lys Arg Thr Thr Lys Asn Leu Glu Ala Gly
225                 230                 235                 240
Val Met Lys Glu Met Ser Asn Ser Lys Glu Leu Thr Leu Arg Ile His
                245                 250                 255
Ser Lys Asn Phe His Glu Asp Thr Leu Ser Ser Thr Lys Ala Lys Gly
                260                 265                 270
His Asn Pro Arg Ser Ser Ile Ala Val Lys Leu Phe Lys Phe Ser Arg
                275                 280                 285
Glu Lys Lys Ala Ala Lys Thr Leu Gly Ile Val Val Gly Met Phe Ile
                290                 295                 300
Leu Cys Trp Leu Pro Phe Phe Ile Ala Leu Pro Leu Gly Ser Leu Phe
305                 310                 315                 320
Ser Thr Leu Lys Pro Pro Asp Ala Val Phe Lys Val Val Phe Trp Leu
                325                 330                 335
Gly Tyr Phe Asn Ser Cys Leu Asn Pro Ile Ile Tyr Pro Cys Ser Ser
                340                 345                 350
Lys Glu Phe Lys Arg Ala Phe Met Arg Ile Leu Gly Cys Gln Cys Arg
                355                 360                 365
Ser Gly Arg Arg Arg Arg Arg Arg Leu Gly Ala Cys Ala Tyr
                370                 375                 380
Thr Tyr Arg Pro Trp Thr Arg Gly Gly Ser Leu Glu Arg Ser Gln Ser
385                 390                 395                 400
Arg Lys Asp Ser Leu Asp Asp Ser Gly Ser Cys Met Ser Gly Ser Gln
                405                 410                 415
Arg Thr Leu Pro Ser Ala Ser Pro Ser Pro Gly Tyr Leu Gly Arg Gly
                420                 425                 430
Ala Gln Pro Pro Leu Glu Leu Cys Ala Tyr Pro Glu Trp Lys Ser Gly
                435                 440                 445
Ala Leu Leu Ser Leu Pro Glu Pro Pro Gly Arg Arg Gly Arg Leu Asp
450                 455                 460
```

```
Ser Gly Pro Leu Phe Thr Phe Lys Leu Leu Gly Glu Pro Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
                500                 505                 510

Gly His Phe
        515

<210> SEQ ID NO 4
<211> LENGTH: 515
<212> TYPE: PRT
<213> ORGANISM: Golden hamster

<400> SEQUENCE: 4

Met Asn Pro Asp Leu Asp Thr Gly His Asn Thr Ser Ala Pro Ala Gln
  1               5                  10                  15

Trp Gly Glu Leu Lys Asp Ala Asn Phe Thr Gly Pro Asn Gln Thr Ser
                 20                  25                  30

Ser Asn Ser Thr Leu Pro Gln Leu Asp Val Thr Arg Ala Ile Ser Val
             35                  40                  45

Gly Leu Val Leu Gly Ala Phe Ile Leu Phe Ala Ile Val Gly Asn Ile
 50                  55                  60

Leu Val Ile Leu Ser Val Ala Cys Asn Arg His Leu Arg Thr Pro Thr
 65                  70                  75                  80

Asn Tyr Phe Ile Val Asn Leu Ala Ile Ala Asp Leu Leu Leu Ser Phe
                 85                  90                  95

Thr Val Leu Pro Phe Ser Ala Thr Leu Glu Val Leu Gly Tyr Trp Val
            100                 105                 110

Leu Gly Arg Ile Phe Cys Asp Ile Trp Ala Ala Val Asp Val Leu Cys
        115                 120                 125

Cys Thr Ala Ser Ile Leu Ser Leu Cys Ala Ile Ser Ile Asp His Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
290                 295                 300

Leu Cys Trp Leu Pro Phe Phe Ile Ala Leu Pro Leu Gly Ser Leu Phe
```

```
                305                 310                 315                 320
Ser Thr Leu Lys Pro Pro Asp Ala Val Phe Lys Val Phe Trp Leu
                325                 330                 335

Gly Tyr Phe Asn Ser Cys Leu Asn Pro Ile Ile Tyr Pro Cys Ser Ser
                340                 345                 350

Lys Glu Phe Lys Arg Ala Phe Met Arg Ile Leu Gly Cys Gln Cys Arg
                355                 360                 365

Ser Gly Arg Arg Arg Arg Arg Arg Arg Leu Gly Ala Cys Ala Tyr
                370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
                405                 410                 415

Arg Thr Leu Pro Ser Ala Ser Pro Ser Pro Gly Tyr Leu Gly Arg Gly
                420                 425                 430

Ala Gln Pro Pro Leu Glu Leu Cys Ala Tyr Pro Glu Trp Lys Ser Gly
                435                 440                 445

Ala Leu Leu Ser Leu Pro Glu Pro Pro Gly Arg Arg Gly Arg Leu Asp
                450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
                500                 505                 510

Gly His Phe
        515

<210> SEQ ID NO 5
<211> LENGTH: 515
<212> TYPE: PRT
<213> ORGANISM: Golden hamster

<400> SEQUENCE: 5

Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
                20                  25                  30

Ser Asn Ser Thr Leu Pro Gln Leu Asp Val Thr Arg Ala Ile Ser Val
            35                  40                  45

Gly Leu Val Leu Gly Ala Phe Ile Leu Phe Ala Ile Val Gly Asn Ile
        50                  55                  60

Leu Val Ile Leu Ser Val Ala Cys Asn Arg His Leu Arg Thr Pro Thr
65              70                  75                  80

Asn Tyr Phe Ile Val Asn Leu Ala Ile Ala Asp Leu Leu Leu Ser Phe
                85                  90                  95

Thr Val Leu Pro Phe Ser Ala Thr Leu Glu Val Leu Gly Tyr Trp Val
                100                 105                 110

Leu Gly Arg Ile Phe Cys Asp Ile Trp Ala Ala Val Asp Val Leu Cys
                115                 120                 125

Cys Thr Ala Ser Ile Leu Ser Leu Cys Ala Ile Ser Ile Asp Asn Tyr
            130                 135                 140

Ile Gly Val Arg Tyr Ser Leu Gln Tyr Pro Thr Leu Val Thr Arg Arg
145                 150                 155                 160
```

```
Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Met Arg Ile Leu Gly Cys Gln Cys Arg
        355                 360                 365

Ser Gly Arg Arg Arg Arg Arg Arg Arg Leu Gly Ala Cys Ala Tyr
    370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
                405                 410                 415

Arg Thr Leu Pro Ser Ala Ser Pro Ser Pro Gly Tyr Leu Gly Arg Gly
            420                 425                 430

Ala Gln Pro Pro Leu Glu Leu Cys Ala Tyr Pro Glu Trp Lys Ser Gly
        435                 440                 445

Ala Leu Leu Ser Leu Pro Glu Pro Pro Gly Arg Arg Gly Arg Leu Asp
450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
            500                 505                 510

Gly His Phe
        515

<210> SEQ ID NO 6
<211> LENGTH: 359
<212> TYPE: PRT
<213> ORGANISM: Rattus norvegicus

<400> SEQUENCE: 6

Met Ala Leu Asn Ser Ser Ala Glu Asp Gly Ile Lys Arg Ile Gln Asp
1               5                   10                  15
```

```
Asp Cys Pro Lys Ala Gly Arg His Ser Tyr Ile Phe Val Met Ile Pro
            20                  25                  30

Thr Leu Tyr Ser Ile Ile Phe Val Gly Ile Phe Gly Asn Ser Leu
        35                  40                  45

Val Val Ile Val Ile Tyr Phe Tyr Met Lys Leu Lys Thr Val Ala Ser
 50                  55                  60

Val Phe Leu Leu Asn Leu Ala Leu Ala Asp Leu Cys Phe Leu Leu Thr
 65                  70                  75                  80

Cys Pro Leu Trp Ala Val Tyr Thr Ala Met Glu Tyr Arg Trp Pro Phe
                85                  90                  95

Gly Asn His Leu Cys Lys Ile Ala Ser Ala Ser Val Thr Phe Asn Leu
            100                 105                 110

Tyr Ala Ser Val Phe Leu Leu Thr Cys Leu Ser Ile Asp His Tyr Leu
            115                 120                 125

Ala Ile Val His Pro Met Lys Ser Arg Leu Arg Arg Thr Met Leu Val
130                 135                 140

Ala Lys Val Thr Cys Ile Ile Trp Leu Met Ala Gly Leu Ala Ser
145                 150                 155                 160

Leu Pro Ala Val Ile His Arg Asn Val Tyr Phe Ile Glu Asn Thr Asn
                165                 170                 175

Ile Thr Val Cys Ala Phe His Tyr Glu Ser Arg Asn Ser Thr Leu Pro
            180                 185                 190

Ile Gly Leu Gly Leu Thr Lys Asn Ile Leu Gly Phe Leu Phe Pro Phe
            195                 200                 205

Leu Ile Ile Leu Thr Ser Tyr Thr Leu Ile Trp Lys Ala Leu Lys Lys
    210                 215                 220

Ala Tyr Glu Ile Gln Lys Asn Lys Pro Arg Asn Asp Asp Ile Phe Arg
225                 230                 235                 240

Ile Ile Met Ala Ile Val Leu Phe Phe Phe Ser Trp Val Pro His
                245                 250                 255

Gln Ile Phe Thr Phe Leu Asp Val Leu Ile Gln Leu Gly Val Ile His
            260                 265                 270

Asp Cys Lys Ile Ser Asp Ile Val Asp Thr Ala Met Pro Ile Thr Ile
            275                 280                 285

Cys Ile Ala Tyr Phe Asn Asn Cys Leu Asn Pro Leu Phe Tyr Gly Phe
            290                 295                 300

Leu Gly Lys Lys Phe Lys Lys Tyr Phe Leu Gln Leu Leu Lys Tyr Ile
305                 310                 315                 320

Pro Pro Lys Ala Lys Ser His Ser Ser Leu Ser Thr Lys Met Ser Thr
                325                 330                 335

Leu Ser Tyr Arg Pro Ser Asp Asn Met Ser Ser Ser Ala Lys Lys Pro
            340                 345                 350

Ala Ser Cys Phe Glu Val Glu
            355

<210> SEQ ID NO 7
<211> LENGTH: 1116
<212> TYPE: DNA
<213> ORGANISM: Homo sapiens

<400> SEQUENCE: 7
atgctcatgg cgtccaccac ttccgctgtg cctgggcatc cctctctgcc cagcctgccc      60
agcaacagca gccaggagag gccactggac acccgggacc cgctgctagc ccgggcggag     120
```

-continued

```
ctggcgctgc tctccatagt ctttgtggct gtggccctga gcaatggcct ggtgctggcg      180
gccctagctc ggcggggccg gcggggccac tgggcaccca tacacgtctt cattggccac      240
ttgtgcctgg ccgacctggc cgtggctctg ttccaagtgc tgccccagct ggcctggaag      300
gccaccgacc gcttccgtgg gccagatgcc ctgtgtcggg ccgtgaagta tctgcagatg      360
gtgggcatgt atgcctcctc ctacatgatc ctggccatga cgctggacca ccaccgtgcc      420
atctgccgtc ccatgctggc gtaccgccat ggaagtgggg ctcactggaa ccggccggtg      480
ctagtggctt gggccttctc gctccttctc agcctgcccc agctcttcat cttcgcccag      540
cgcaacgtgg aaggtggcag cggggtcact gactgctggg cctgctttgc ggagccctgg      600
ggccgtcgca cctatgtcac ctggattgcc ctgatggtgt cgtggcacc tacccctgggt      660
atcgccgcct gccaggtgct catcttccgg gagattcatg ccagtctggt gccagggcca      720
tcagagaggc ctgggggggcg ccgcagggga cgccggacag gcagccccgg tgagggagcc      780
cacgtgtcag cagctgtggc caagactgtg aggatgacgc tagtgattgt ggtcgtctat      840
gtgctgtgct gggcacccct cttcctggtg cagctgtggg ccgcgtggga cccggaggca      900
cctctggaag gggcgccctt tgtgctactc atgttgctgg ccagcctcaa cagctgcacc      960
aaccccctgga tctatgcatc tttcagcagc agcgtgtcct cagagctgcg aagcttgctc     1020
tgctgtgccc ggggacgcac cccacccagc ctgggtcccc aagatgagtc ctgcaccacc     1080
gccagctcct ccctggccaa ggacacttca tcgtga                               1116
```

<210> SEQ ID NO 8
<211> LENGTH: 1548
<212> TYPE: DNA
<213> ORGANISM: Syrian golden hamster

<400> SEQUENCE: 8

```
atgaatcccg atctggacac cggccacaac acatcagcac ctgcccaatg gggagagttg       60
aaagatgcca acttcactgg ccccaaccag acctcgagca actccacact gccccagctg      120
gacgttacca gggccatctc tgtgggcctg tgtctgggcg ccttcatcct ctttgccatt      180
gtgggcaaca tcctggtcat cctgtcagtg gcctgcaatc ggcacctgcg gacgcccacc      240
aactacttca ttgtcaacct ggccattgct gacctgctgt tgagtttcac agtcctgccc      300
ttctccgcta cccctagaagt gcttggctac tgggttctgg ggcgcatctt ctgtgacatc      360
tgggcagcgg tggacgtcct gtgctgtacg gcctccatcc tgagcctatg tgccatctcc      420
attgatcact acattggggt gcgctactct ctgcagtacc ccactctggt cacccgcagg      480
aaggccatct tggcactcct cagtgtgtgg gttttgtcca cggtcatctc catcgggcct      540
ctccttggat ggaaagaacc agcgcccaac gacgacaagg aatgcggagt caccgaagaa      600
cccttctatg ccctctttc ctccctgggc tccttctaca tcccactcgc ggtcattctg      660
gtcatgtact gccgggtcta catcgtgcc aagaggacca ccaagaacct ggaggctgga      720
gtcatgaagg agatgtccaa ctccaaggag ctgaccctga ggatccactc aagaactttt     780
catgaggaca ccctcagcag taccaaggcc aagggccaca cccccaggag ttccatagct      840
gtcaaacttt ttaagttctc cagggaaaag aaagcagcca aaaccttggg cattgtggtc      900
ggaatgttca tcttgtgttg gctccccctt ttcatcgctc tcccacttgg ctccctgttc      960
tccactctca gcccccggaa cgccgtgttc aaggtggtat tctggctggg ctacttcaac     1020
agctgcctca accccatcat ctaccgtgc tccagcaagg agttcaagcg cgccttcatg     1080
cgtatccttg ggtgccagtg ccgtagtggc cgtcgccgcc gccgccgccg tcgtctgggc     1140
```

-continued

```
gcgtgcgctt acacctatcg gccgtggacg cgcggcggct cgctggagcg atcgcagtcg    1200
cggaaggact ccctggacga cagcggcagc tgcatgagtg gcagccagag gaccctgccc    1260
tcggcgtcgc ccagcccggg ctacctgggt cgcggagcgc agccaccact ggagctgtgc    1320
gcctaccccg aatggaaatc cggggctctg ctcagtctgc cagagcctcc gggtcgccgc    1380
ggtcgcctcg actctgggcc cctcttcact ttcaagctct gggagagcc ggagagcccg     1440 ggcaccgagg gcgatgccag caatgggggc tgcgacgcaa cgaccgacct ggccaatggg    1500
cagcccggtt tcaagagcaa catgcctctg gcacccgggc acttttag                 1548
```

<210> SEQ ID NO 9
<211> LENGTH: 1548
<212> TYPE: DNA
<213> ORGANISM: Syrian golden hamster

<400> SEQUENCE: 9

```
atgaatcccg atctggacac cggccacaac acatcagcac ctgcccaatg gggagagttg      60
aaagatgcca acttcactgg ccccaaccag acctcgagca actccacact gccccagctg     120
gacgttacca gggccatctc tgtgggcctg gtgctgggcg ccttcatcct ctttgccatt     180
gtgggcaaca tcctggtcat cctgtcagtg gcctgcaatc ggcacctgcg gacgcccacc     240
aactacttca ttgtcaacct ggccattgct gacctgctgt tgagtttcac agtcctgccc     300
ttctccgcta ccctagaagt gcttggctac tgggttctgg ggcgcatctt ctgtgacatc     360
tgggcagcgg tggacgtcct gtgctgtacg gcctccatcc tgagcctatg tgccatctcc     420
attgatgcct acattggggt gcgctactct ctgcagtacc ccactctggt cacccgcagg     480
aaggccatct tggcactcct cagtgtgtgg gttttgtcca cggtcatctc catcgggcct     540
ctccttggat ggaaagaacc agcgcccaac gacgacaagg aatgcggagt caccgaagaa     600
cccttctatg ccctcttttc ctccctgggc tccttctaca tcccactcgc ggtcattctg     660
gtcatgtact gccgggtcta catcgtggcc aagaggacca ccaagaacct ggaggctgga     720
gtcatgaagg agatgtccaa ctccaaggag ctgaccctga ggatccactc caagaacttt     780
catgaggaca ccctcagcag taccaaggcc aagggccaca accccaggag ttccatagct     840
gtcaaacttt ttaagttctc cagggaaaag aaagcagcca aaaccttggg cattgtggtc     900
ggaatgttca tcttgtgttg gctccccttc ttcatcgctc tcccacttgg ctccctgttc     960
tccactctca gccccggga cgccgtgttc aaggtggtat tctggctggg ctacttcaac    1020
agctgcctca accccatcat ctacccgtgc tccagcaagg agttcaagcg cgccttcatg    1080
cgtatccttg ggtgccagtg ccgtagtggc cgtcgccgcc gccgccgccg tcgtctgggc    1140
gcgtgcgctt acacctatcg gccgtggacg cgcggcggct cgctggagcg atcgcagtcg    1200
cggaaggact ccctggacga cagcggcagc tgcatgagtg gcagccagag gaccctgccc    1260
tcggcgtcgc ccagcccggg ctacctgggt cgcggagcgc agccaccact ggagctgtgc    1320
gcctaccccg aatggaaatc cggggctctg ctcagtctgc cagagcctcc gggtcgccgc    1380
ggtcgcctcg actctgggcc cctcttcact ttcaagctct gggagagcc ggagagcccg     1440 ggcaccgagg gcgatgccag caatgggggc tgcgacgcaa cgaccgacct ggccaatggg    1500
cagcccggtt tcaagagcaa catgcctctg gcacccgggc acttttag                 1548
```

<210> SEQ ID NO 10
<211> LENGTH: 1548
<212> TYPE: DNA

<213> ORGANISM: Syrian golden hamster

<400> SEQUENCE: 10

```
atgaatcccg atctggacac cggccacaac acatcagcac ctgcccaatg gggagagttg      60
aaagatgcca acttcactgg ccccaaccag acctcgagca actccacact gccccagctg     120
gacgttacca gggccatctc tgtgggcctg gtgctgggcg ccttcatcct ctttgccatt     180
gtgggcaaca tcctggtcat cctgtcagtg gcctgcaatc ggcacctgcg gacgcccacc     240
aactacttca ttgtcaacct ggccattgct gacctgctgt tgagtttcac agtcctgccc     300
ttctccgcta ccctagaagt gcttggctac tgggttctgg ggcgcatctt ctgtgacatc     360
tgggcagcgg tggacgtcct gtgctgtacg gcctccatcc tgagcctatg tgccatctcc     420
attgatgagt acattggggt gcgctactct ctgcagtacc ccactctggt cacccgcagg     480
aaggccatct tggcactcct cagtgtgtgg gttttgtcca cggtcatctc catcgggcct     540
ctccttggat ggaagaacc agcgcccaac gacgacaagg aatgcggagt caccgaagaa     600
cccttctatg ccctcttttc ctccctgggc tccttctaca tcccactcgc ggtcattctg     660
gtcatgtact gccgggtcta catcgtggcc aagaggacca ccaagaacct ggaggctgga     720
gtcatgaagg agatgtccaa ctccaaggag ctgaccctga ggatccactc caagaacttt     780
catgaggaca ccctcagcag taccaaggcc aagggccaca cccccaggag ttccatagct     840
gtcaaacttt ttaagttctc cagggaaaag aaagcagcca aaaccttggg cattgtggtc     900
ggaatgttca tcttgtgttg gctcccctttc ttcatcgctc tcccacttgg ctccctgttc     960
tccactctca agccccgga cgccgtgttc aaggtggtat tctggctggg ctacttcaac    1020
agctgcctca cccccatcat ctacccgtgc tccagcaagg agttcaagcg cgccttcatg    1080
cgtatccttg ggtgccagtg ccgtagtggc cgtcgccgcc gccgccgccg tcgtctgggc    1140
gcgtgcgctt acacctatcg gccgtggacg cgcggcggct cgctggagcg atcgcagtcg    1200
cggaaggact ccctggacga cagcggcagc tgcatgagtg gcagccagag gaccctgccc    1260
tcggcgtcgc ccagcccggg ctacctgggt cgcggagcgc agccaccact ggagctgtgc    1320
gcctaccccg aatggaaatc cggggctctg ctcagtctgc cagagcctcc gggtcgccgc    1380
ggtcgcctcg actctgggcc cctcttcact ttcaagctct tgggagagcc ggagagcccg    1440
ggcaccgagg gcgatgccag caatgggggc tgcgacgcaa cgaccgacct ggccaatggg    1500
cagcccggtt tcaagagcaa catgcctctg gcacccgggc acttttag              1548
```

<210> SEQ ID NO 11
<211> LENGTH: 1548
<212> TYPE: DNA
<213> ORGANISM: Syrian golden hamster

<400> SEQUENCE: 11

```
atgaatcccg atctggacac cggccacaac acatcagcac ctgcccaatg gggagagttg      60
aaagatgcca acttcactgg ccccaaccag acctcgagca actccacact gccccagctg     120
gacgttacca gggccatctc tgtgggcctg gtgctgggcg ccttcatcct ctttgccatt     180
gtgggcaaca tcctggtcat cctgtcagtg gcctgcaatc ggcacctgcg gacgcccacc     240
aactacttca ttgtcaacct ggccattgct gacctgctgt tgagtttcac agtcctgccc     300
ttctccgcta ccctagaagt gcttggctac tgggttctgg ggcgcatctt ctgtgacatc     360
tgggcagcgg tggacgtcct gtgctgtacg gcctccatcc tgagcctatg tgccatctcc     420
attgataact acattggggt gcgctactct ctgcagtacc ccactctggt cacccgcagg     480
```

-continued

```
aaggccatct tggcactcct cagtgtgtgg gttttgtcca cggtcatctc catcgggcct      540
ctccttggat ggaaagaacc agcgcccaac gacgacaagg aatgcggagt caccgaagaa      600
cccttctatg ccctcttttc ctccctgggc tccttctaca tcccactcgc ggtcattctg      660
gtcatgtact gccgggtcta catcgtggcc aagaggacca ccaagaacct ggaggctgga      720
gtcatgaagg agatgtccaa ctccaaggag ctgaccctga ggatccactc caagaacttt      780
catgaggaca ccctcagcag taccaaggcc aagggccaca cccccaggag ttccatagct      840
gtcaaacttt ttaagttctc cagggaaaag aaagcagcca aaaccttggg cattgtggtc      900
ggaatgttca tcttgtgttg gctccccttc ttcatcgctc tcccacttgg ctccctgttc      960
tccactctca agccccggga cgccgtgttc aaggtggtat tctggctggg ctacttcaac     1020
agctgcctca accccatcat ctacccgtgc tccagcaagg agttcaagcg cgccttcatg     1080
cgtatccttg ggtgccagtg ccgtagtggc cgtcgccgcc gccgccgccg tcgtctgggc     1140
gcgtgcgctt acacctatcg gccgtggacg cgcggcggct cgctggagcg atcgcagtcg     1200
cggaaggact ccctggacga cagcggcagc tgcatgagtg gcagcagaga gaccctgccc     1260
tcggcgtcgc ccagcccggg ctacctgggt cgcggagcgc agccaccact ggagctgtgc     1320
gcctaccccg aatggaaatc cggggctctg ctcagtctgc cagagcctcc gggtcgccgc     1380
ggtcgcctcg actctgggcc cctcttcact ttcaagctct gggagagcc ggagagcccg     1440 ggcaccgagg gcgatgccag caatgggggc tgcgacgcaa cgaccgacct ggccaatggg     1500
cagcccggtt tcaagagcaa catgcctctg gcacccgggc acttttag                  1548
```

<210> SEQ ID NO 12
<211> LENGTH: 1080
<212> TYPE: DNA
<213> ORGANISM: Rattus norvegicus

<400> SEQUENCE: 12

```
atggcccttta actcttctgc tgaagatggt atcaaaagaa tccaagatga ctgccccaag      60
gctggcaggc acagttacat atttgtcatg atccctaccc tctacagcat catctttgtg     120
gtgggaatat ttggaaacag cttggtggtg attgtcattt acttttacat gaagctgaag     180
actgtggcca cgctctttct ctcaatctcg gccttggctg acttatgctt tttgctgact     240 tgtccccctgt gggcagtcta taccgctatg gagtaccgct ggcccttcgg caatcaccta     300
tgtaagatcg cttcggccag cgtgacgttc aacctctacg ccagtgtgtt ccttctcacg     360
tgtctcagca tcgaccacta cctggccatc gtccacccaa tgaagtctcg ccttcgccgc     420
acgatgctgg tggccaaagt cacctgcatc atcatctggc tgatggctgg cttggccagt     480
ttgccagctg tcatccaccg aaatgtatac ttcatcgaga acaccaatat cacagtgtgc     540
gcgtttcatt atgagtctcg gaattcgacg ctccccatag ggctgggcct taccaagaat     600
attctgggct tcttgttccc tttccttatc attctcacca gctataccct tatttggaaa     660
gctctaaaga aggcttatga aattcaaaag aacaaaccaa gaaacgatga catctttagg     720
ataattatgg cgattgtgct tttcttcttc ttttcctggg tcccccacca aatattcact     780
ttcctggatg tgctgattca gctgggcgtc atccatgact gtaaaatttc tgacatcgtg     840
gacactgcca tgcccatcac catctgcata gcgtatttta acaactgcct gaaccctctg     900
ttctacggct ttctggggaa gaaatttaaa agtatttcc tccagctcct gaaatatatt     960
```

```
cccccaaagg ccaagtccca ctcaagcctg tctacgaaaa tgagcacgct ttcttaccgg    1020
ccttcggata acatgagctc atcggccaaa aagcctgcgt cttgttttga ggtggagtga    1080
```

NUCLEIC ACID ENCODING G-PROTEIN COUPLED RECEPTOR WITH MODIFIED DRY MOTIF

This application claims priority under 35 U.S.C. § 120 to U.S. Ser. No. 60/263,406, filed Jan. 23, 2001, the contents of which are hereby incorporated by reference in their entirety.

This work was supported by National Institutes of Health Grants HL 61365 and NS 19576, and therefore the government may have certain rights to the invention.

FIELD OF THE INVENTION

The present invention relates to modified G-protein coupled receptors (GPCRs). The modified GPCRs of the present invention include GPCRs that have been modified to have altered DRY motifs such that the proteins localize to endocytic vesicles or endosomes in an agonist-independent manner. This invention also includes mutant proteins that result in agonist-independent GPCR localization to endocytic vesicles or endosomes. This invention also relates to methods of detecting G protein-coupled receptor (GPCR) activity and methods of assaying GPCR activity. The present invention provides methods for identifying compounds that interact with components of the GPCR regulatory pathway and methods for identifying antagonists of GPCRs.

BACKGROUND OF THE INVENTION

G protein-coupled receptors (GPCRs) are cell surface proteins that translate hormone or ligand binding into intracellular signals. GPCRs have been found in all animals, insects, and plants studied to date. GPCR signaling plays a pivotal role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length.

The magnitude of the physiological responses controlled by GPCRs is linked to the balance between GPCR signaling and signal termination. The signaling of GPCRs is controlled by a family of intracellular proteins called arrestins. Arrestins bind activated GPCRs, including those that have been agonist-activated and especially those that have been phosphorylated by G protein-coupled receptor kinases (GRKs).

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See e.g., Jurgen Drews, (2000) "Drug Discovery: A Historical Perspective," *Science* 287:1960–1964.

Although only several hundred human GPCRs are known, it is estimated that upwards of a thousand GPCRs exist in the human genome. Of these known GPCRs, many are orphan receptors that have yet to be associated with a function or a ligand.

There is a need for accurate, easy to interpret methods of detecting G protein-coupled receptor activity and methods of assaying GPCR activity. One method, as disclosed in Barak et al., U.S. Pat. Nos. 5,891,646 and 6,110,693, uses a cell expressing a GPCR and a conjugate of an arrestin and a detectable molecule, the contents of which are incorporated by reference in their entirety.

The majority of the existing methods for identifying GPCR antagonists are dependent on the presence of agonist. Assays for identifying compounds that prevent the activation of GPCRs typically require that the GPCR is first activated in order to identify interfering compounds. For receptors with known agonists, these agonists are currently used to activate these receptors. However, many GPCRs are orphan receptors with no known ligand or agonist.

One method, as disclosed in Pausch et al., WO 00/12704, uses GPCRs with constitutively activating mutations that permit detection of the receptors' functional activity in the absence of activating ligands. In Pausch et al. modifications are made to the GPCR that result in a constitutively active receptor. The constitutively active GPCR mutants of Pausch et al. have elevated intrinsic activity compared to wild type receptors and interact with and activate intracellular heterotrimeric G proteins in an agonist-independent manner. The method of Pausch et al., although agonist-independent, utilizes constitutively active GPCR mutants.

The agonist-dependence of GPCR assays continues to be a problem because antagonist discovery for orphan receptors is typically dependent on the prior discovery of agonist or ligand. Therefore, there is a need to provide additional methods of GPCR activation that are not dependent on agonist.

SUMMARY

The present invention relates to modified GPCRs that are constitutively desensitized.

A first aspect of the present invention is a modified GPCR or biologically active fragment thereof comprising a DRY motif. In the modified GPCR of the present invention the DRY motif is modified to contain an amino acid other than arginine at position 2. The modified GPCR or biologically active fragment thereof is constitutively desensitized in absence of agonist. The modified GPCR of the present invention may bind arrestin, localize to clathrin-coated pits, or localize in endocytic vesicles or endosomes in absence of agonist. The modified GPCR may be derived from a naturally occurring GPCR. The modified GPCR may be a *Homo sapien* GPCR, a Class A GPCR, a Class B GPCR, an orphan GPCR, or an odorant or taste GPCR.

In an additional aspect, the present invention relates to an isolated modified arrestin polypeptide. The isolated modified arrestin polypeptide of the present invention produces a constitutively desensitized GPCR when expressed in a cell.

In a further aspect, the present invention relates to an isolated modified GRK polypeptide. The isolated modified GRK polypeptide produces a constitutively desensitized GPCR when expressed in a cell.

The present invention also includes modified GPCRs proteins having the activities noted herein, and that display the amino acid sequences set forth and described above and selected from SEQ. ID. NO: 1–SEQ. ID. NO.: 6. When expressed in a cell, the polypeptide binds arrestin in absence of agonist and may target to an endocytic vesicle or endosome in the absence of agonist. The polypeptide comprises a modified DRY motif wherein the arginine of the DRY motif is any naturally occurring amino acid or synthetic amino acid except arginine.

The present invention also relates to a nucleic acid encoding an isolated modified GPCR or biologically active fragment thereof of claim 1. The nucleic acid sequence of the present invention may be selected from SEQ. ID. No.: 7–SEQ. ID. No.: 12.

The present invention further relates to vectors comprising a nucleic acid sequence as described herein. The nucleic acid may be operatively linked to an expression control sequence and introduced into an appropriate host. The invention accordingly extends to unicellular hosts transformed with the cloned gene or recombinant DNA molecule comprising a DNA sequence encoding the present modified GPCR(s).

In a further aspect, the present invention relates to methods of screening compositions, compounds, and sample solutions. These methods include methods of identifying a compound which inhibits arrestin binding to a GPCR. The method comprises a) preparing an isolated modified GPCR or biologically active fragment thereof which targets to an endocytic vesicle or endosome without agonist; b) attaching the isolated modified GPCR or biologically active fragment thereof to a substrate; c) exposing the isolated modified GPCR or biologically active fragment thereof to a candidate compound; d) exposing the isolated modified GPCR or biologically active fragment thereof to an arrestin or biologically active fragment of arrestin; and e) determining if binding of arrestin or the biologically active fragment of arrestin is blocked.

The methods of the present invention also include methods of identifying compounds that interfere with agonist-independent localization of arrestin. This method comprises (a) preparing a modified GPCR or biologically active fragment thereof; (b) expressing the modified GPCR or biologically active fragment thereof in a cell that also expresses arrestin; (c) exposing the cell to a candidate compound; and (d) determining whether the candidate compound inhibits endosomal targeting of arrestin.

The methods of the present invention also include methods of identifying a compound that has GPCR antagonist or inverse agonist activity This method comprises a) preparing an isolated modified GPCR or biologically active fragment thereof which targets to an endosome or endocytic vesicle without agonist; b) expressing the modified GPCR or biologically active fragment thereof in a cell that also expresses a conjugate of arrestin and a detectable molecule; c) exposing the cell a candidate compound; and d) detecting whether interaction of the arrestin protein with the GPCR is decreased after exposure to the test compound, the decrease in interaction being an indication that the compound has activity.

In the methods of the present invention, the modified GPCR may be a class A receptor, a class B receptor, an odorant or taste receptor, or an orphan receptor. In the methods of the present invention, the arrestin may be conjugated to a detectable molecule. In the methods of the present invention, the modified GPCR may be conjugated to a detectable molecule. The detectable molecule may be a radioisotope, an epitope tag, an affinity label, an enzyme, a fluorescent group, or a chemiluminescent group.

The present invention also relates to compounds identified by the methods of the present invention. The invention further relates to pharmaceutical compositions for the treatment of a condition mediated by a GPCR in mammals comprising a therapeutically effective amount of a compound identified by the methods of the invention and a pharmaceutically acceptable carrier.

In an additional aspect, the invention relates to a non-human transgenic animal which expresses a modified GPCR. The animal may be a mouse, a primate, a feline, a canine, a porcine, a bovine, a caprine, or an ovine.

In a further aspect, the invention relates to a method of detecting a modified GPCR in a biological sample. The method comprises assaying the biological sample with an antibody which recognizes and binds to the modified GPCR and determining whether the antibody bound the modified GPCR.

In yet a further aspect, the invention relates to a method of detecting a nucleic acid of the present invention in a biological sample. The method comprises (a) exposing the biological sample to a modified GPCR probe; and (b) determining whether the modified GPCR probe bound the nucleic acid of the biological sample.

The invention also relates to a composition comprising a substrate and one or more nucleic acids of the present invention or fragments thereof which encode a motif of formula 1, wherein formula I is a modified DRY motif.

The invention further relates to a kit for detecting a modified GPCR in a biological sample. The kit comprises an antibody which recognizes and binds to the modified GPCR and reagents which detect the antibody that binds to the modified GPCR.

The invention additionally relates to an isolated immunoglobulin which recognizes and binds to a modified GPCR. The immunoglobulin may be a monoclonal antibody, a chimeric antibody, a human antibody, a bispecific antibody, a humanized antibody, a primatized antibody, or an antibody fragment. The immunoglobulin may be an antibody fragment and the antibody fragment may be Fab, Fab', F(ab')2, F(v), and scFv.

In yet another aspect, the invention relates to a method of inhibiting arrestin binding to a GPCR or GPCR localization to endocytic vesicles or endosomes in the absence of agonist by administering an effective amount of 2-ethyl-5,7-dimethyl-3-[[2'-(1H-tetrazol-5-yl)[1,1'-biphenyl]-4-yl]methyl]-3H-Imidazo[4,5-b]pyridine or phentolamine to a patient in need thereof.

Other objects and advantages will become apparent to those skilled in the art from a review of the ensuing description which proceeds with reference to the following illustrative drawings.

BRIEF DESCRIPTION OF DRAWINGS

The objects and advantages of the invention will be understood by reading the following detailed description in conjunction with the drawings in which:

An illustrative, non-limiting list of known GPCRs with which the present invention may be used is contained in FIG. 1. The receptors are grouped according to classical divisions based on structural similarities and ligands.

FIG. 2 illustrates (a) the wild-type DRY motif, as well as (b) the modified DRY motif.

FIG. 3 illustrates the amino acid sequences of the modified GPCRs described herein. Amino acids that differ from the wild-type sequence are in bold and underlined.

FIG. 8 illustrates the expression of V2R, V2R(R137H, Ala6), and V2R(R137H, T362) in HEK-293 cells. (A) Plasma membrane receptors were labeled with rhodamine-tagged mouse-monoclonal anti-HA antibody. The upper panels show receptor distribution in the absence of agonist. The lower panels show cells that were labeled with antibody before treatment with 100 nM AVP for 30 min. at 37° C. (B) Plasma membrane receptor expression measured by [$^3$H] AVP was normalized to wild-type V2R plasma membrane expression (approximately 5 pmol/mg). Data are expressed as the mean±SD from three independent experiments.

FIG. 17 illustrates the nucleic acid sequences encoding the modified GPCRs of the present invention. Nucleic acids that differ from the wild-type sequence are in bold and underlined. Sequences are listed in the 5'→3' orientation.

DETAILED DESCRIPTION OF ILLUSTRATIVE EMBODIMENTS

Figure 4A:
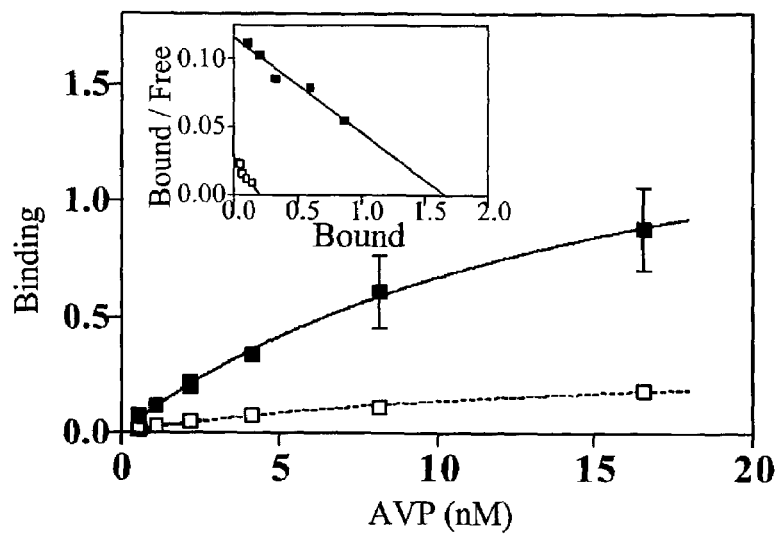
FIG. 4 illustrates the expression and adenylyl cyclase stimulation of V2R and V2R(R137H) in HEK-293 cells. Cells transiently transfected with cDNA for V2R (■) or V2R(R137H) (□) were exposed to varying concentrations of [$^3$H]AVP. (A) Scatchard analysis (Inset) indicates the receptors have similar affinity for AVP [V2R, 16±6 nM; V2R(R137H), 15±3 nM]. V2R expression varied between 2.5 and 5 pmol/mg of cell protein, with the plasma membrane expression of the V2R(R137H) being approximately $\frac{1}{12}$ of this (x intercept of Scatchard). The data are representative of three experiments, with each point measured in duplicate. (B) Fluorescence images of live unpermeabilized cells, labeled with rhodamine-tagged mouse-monoclonal anti-HA antibodies, expressing the V2R (Left) or the V2R (R137H) (Right). (C) cAMP measured in whole cells stimulated for 15 min. with concentrations of AVP between 0 and 250 nM. cAMP accumulation is expressed as total counts of [$^3$H]cAMP/total uptake of [$^3$H]adenine per well of cells. Results are the mean±SD of three experiments.

In accordance with the present invention there may be employed conventional molecular biology, microbiology, immunology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994)]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (2000)]; "Immobilized Cells And Enzymes" [IRL Press, (1986)]; B. Perbal, "A Practical Guide To Molecular Cloning" (1984); *Using Antibodies: A Laboratory Manual: Portable Protocol No. I*, Harlow, Ed and Lane, David (Cold Spring Harbor Press, 1998); *Using Antibodies: A Laboratory Manual*, Harlow, Ed and Lane, David (Cold Spring Harbor Press, 1999).

Unless otherwise stated, the following terms used in the specification and claims have the meanings given below:

An "immunoglobulin" includes antibodies and antibody fragments with immunogenic activity. Preferred immunogenic activity is where the immunoglobulin binds to a modified GPCR. An even more preferable immunoglobulin is one that can distinguish between a modified GPCR and a wild-type GPCR. And the most preferable immunoglobulin is that which binds to a modified DRY motif or a DRY motif of a GPCR. The term "antibody" refers to immunoglobulins, including whole antibodies as well as fragments thereof that recognize or bind to specific epitopes. The term antibody encompasses polyclonal, monoclonal, and chimeric antibodies, the last mentioned described in further detail in U.S. Pat. Nos. 4,816,397 and 4,816,567. The term "epitope" is used to identify one or more portions of an antigen or an immunogen which is recognized or recognizable by antibodies or other immune system components.

Exemplary immunoglobulins are intact immunoglobulin molecules, substantially intact immunoglobulin molecules and those portions of an immunoglobulin molecule that contains the paratope. Antibody fragments include those portions known in the art as Fab, Fab', F(ab')$_2$, F(v), and scFv which portions are preferred for use in the therapeutic methods described herein.

Fab and F(ab')$_2$ portions of antibody fragments are prepared by the proteolytic reaction of papain and pepsin, respectively, on substantially intact antibodies by methods that are well-known. See for example, U.S. Pat. No. 4,342,566 to Theofilopolous et al. Fab' antibody portions are also well-known and are produced from F(ab')$_2$ portions followed by reduction of the disulfide bonds linking the two heavy chain portions as with mercaptoethanol, and followed by alkylation with a reagent such as iodoacetamide. An antibody containing intact antibody portions is preferred herein.

An "antibody combining site" is that structural portion of an antibody comprised of heavy and light chain variable and hypervariable regions that specifically binds antigen.

The phrase "monoclonal antibody" in its various grammatical forms refers to an antibody having only one species of antibody combining site capable of immunoreacting with a particular epitope on an antigen. A monoclonal antibody may therefore contain a plurality of antibody combining sites, each immunospecific for a different antigen, e.g., a bispecific (chimeric) monoclonal antibody.

By "animal" is meant any member of the animal kingdom including vertebrates (e.g., frogs, salamanders, chickens, or horses) and invertebrates (e.g., worms, etc.). "Animal" is also meant to include "mammals." Preferred mammals include livestock animals (e.g., ungulates, such as cattle, buffalo, horses, sheep, pigs and goats), as well as rodents (e.g., mice, hamsters, rats and guinea pigs), canines, felines, primates, lupine, camelid, cervidae, rodent, avian and ichthyes.

"Antagonist(s)" include all agents that interfere with wild-type and/or modified GPCR binding to an agonist, wild-type and/or modified GPCR desensitization, wild-type and/or modified GPCR binding arrestin, wild-type and/or modified GPCR endosomal localization, and the like, including agents that affect the wild-type and/or modified GPCRs as well as agents that affect other proteins involved in wild-type and/or modified GPCR signaling, desensitization, endosomal localization, resensitization, and the like.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

"Abnormal GPCR desensitization" and "abnormal desensitization" mean that the GPCR desensitization pathway is disrupted such that the balance between active receptor and desensitized receptor is altered with respect to wild-type conditions. Either there is more active receptor than normal or there is more desensitized receptor than wild-type conditions. Abnormal GPCR desensitization may be the result of a GPCR that is constitutively active or constitutively desensitized, leading to an increase above normal in the signaling of that receptor or a decrease below normal in the signaling of that receptor.

"Arrestin" means all types of naturally occurring and engineered variants of arrestin, including, but not limited to, visual arrestin (sometimes referred to as Arrestin 1), βarrestin 1 (sometimes referred to as Arrestin 2), and βarrestin 2 (sometimes referred to as Arrestin 3).

"Biologically active fragment" of a modified GPCR means a polypeptide fragment of a modified GPCR which has ability to bind arrestin in an agonist-independent manner, target to endocytic vesicles or endosomes in an agonist-independent manner, or both.

"Biologically active fragment" of an arrestin means a fragment of arrestin which has the ability to bind a wild-type and/or modified GPCR.

"Biological sample" is intended to include tissues, cells and biological fluids isolated from a subject, as well as tissues, cells and fluids present within a subject; wherein said sample can be blood, serum, a urine sample, a fecal sample, a tumor sample, a cellular wash, an oral sample, sputum, biological fluid, a tissue extract, freshly harvested cells, or cells which have been incubated in tissue culture.

As used herein "carboxyl-terminal tail" means the carboxyl-terminal tail of a GPCR. The carboxyl-terminal tail of many GPCRs begins shortly after (within approximately 20 amino acids) the conserved NPXXY motif that marks the end of the seventh transmembrane domain (i.e. what follows the NPXXY motif is the carboxyl-terminal tail of the GPCR). The carboxyl-terminal tail may be relatively long (approximately tens to hundreds of amino acids), relatively short (approximately 10–100 amino acids), or virtually non-existent (less than approximately ten amino acids). As used herein, "carboxyl-terminal tail" shall mean all three variants (whether relatively long, relatively short, or virtually non-existent).

"Class A receptors" preferably do target to endocytic vesicles or endosomes in HEK-293 cells.

A "modified class A receptor" means those class A receptors that contain a DRY mutation.

"Class B receptors" preferably do not target to endocytic vesicles or endosomes in HEK-293 cells.

A "modified class B receptor" means those class B receptors that contain a DRY mutation.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

"Concurrent administration," "administration in combination," "simultaneous administration," or "administered simultaneously" mean that the compounds are administered at the same point in time or sufficiently close in time that the results observed are essentially the same as if the two or more compounds were administered at the same point in time.

"Conserved abnormality" means an abnormality in the GPCR pathway, including but not limited to, abnormalities in GPCRs, GRKs, arresting, AP-2 protein, clathrin, protein phosphatase and the like, that may cause abnormal GPCR signaling. This abnormal GPCR signaling may contribute to a GPCR-related disease.

For a "constitutively desensitized" GPCR, the equilibrium between a GPCR having the ability, versus inability, to properly activate conventional G protein signaling is shifted toward the inability to properly activate conventional G protein signaling. Additionally, the constitutively desensitized GPCRs of the present invention are constitutively phosphorylated, constitutively bind arrestin, constitutively localize in clathrin-coated pits, and/or constitutively localize to endocytic vesicles or endosomes. Constitutively desensitized receptors lack ability to properly respond to agonist and may be desensitized even in the absence of agonist. Constitutively desensitized GPCRs form independent of agonist stimulation of the sensitized GPCR. Constitutively desensitized may cover a host of degrees of inappropriate signaling and a constitutively desensitized receptor may or may not signal at some point during its lifetime.

"Detectable molecule" means any molecule capable of detection by spectroscopic, photochemical, biochemical, immunochemical, electrical, radioactive, and optical means, including but not limited to, fluorescence, phosphorescence, and bioluminescence and radioactive decay. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s).

"Desensitized GPCR" means a GPCR that presently does not have ability to respond to agonist and activate conventional G protein signaling. Desensitized GPCRs of the present invention do not properly respond to agonist, are phosphorylated, bind arrestin, constitutively localize in clathrin-coated pits, and/or constitutively localize to endocytic vesicles or endosomes "Desensitization pathway" means any cellular component of the desensitization process, as well as any cellular structure implicated in the desensitization process and subsequent processes, including but not limited to, arrestins, GRKs, GPCRs, AP-2 protein, clathrin, protein phosphatases, and the like. In the methods of assaying of the present invention, the polypeptides may be detected, for example, in the cytoplasm, at a cell membrane, in clathrin-coated pits, in endocytic vesicles, endosomes, any stages in between, and the like.

"DACs" mean any desensitization active compounds. Desensitization active compounds are any compounds that influence the GPCR desensitization mechanism by either stimulating or inhibiting the process. DACs influence the GPCR desensitization pathway by acting on any cellular component of the process, as well as any cellular structure implicated in the process, including but not limited to, arresting, GRKs, GPCRs, AP-2 protein, clathrin, protein phosphatases, and the like. DACs may include, but are not limited to, compounds that inhibit arrestin translocating to a GPCR, compounds that inhibit arrestin binding to a GPCR, compounds that stimulate arrestin translocating to a GPCR, compounds that stimulate arrestin binding to a GPCR, compounds that inhibit GRK phosphorylation of a GPCR, compounds that stimulate GRK phosphorylation of a GPCR, compounds that inhibit protein phosphatase dephosphorylation of a GPCR, compounds that stimulate protein phosphatase dephosphorylation of a GPCR, compounds that regulate the release of arrestin from a GPCR, antagonists of a GPCR, inverse agonists and the like. DACs preferably inhibit or stimulate the GPCR desensitization process without binding to the same ligand binding site of the GPCR as traditional agonists and antagonists of the GPCR.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

"DRY motif" means a highly conserved GPCR motif located near the cytoplasmic boundary of the third transmembrane region and the second intracellular loop. The DRY motif is most preferably a three amino acid motif: Aspartate-Arginine-Tyrosine, wherein Aspartate is the first amino acid, Arginine is the second amino acid, and tyrosine is the third amino acid (or DRY if using single amino acid substitions), wherein the DRY is also referred to as formula I. Variations of this amino acid sequence which do not confer agonist-independent binding to arrestin or agonist-independent endosomal localization to the GPCR are also included. For example, the first amino acid may be a Glutamate (i.e. ERY), Leucine, Proline, Glutamine, Threonine, Isoleucine, Cysteine, Glycine, Asparagine, Valine, Histidine, or Alanine. For example, the third amino acid may be a Histidine (i.e. DRH), Tryptophan, Phenylalanine, Serine, Isoleucine, Glutamine, Histidine, Glycine, Cysteine, Leucine, Aspartate, or Alanine. There may be more than one substitution in the DRY motif, or any combination of substitutions. The wild-type DRY motif and preferred modifications are illustrated in FIG. 2a.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

"GFP" means Green Fluorescent Protein which refers to various naturally occurring forms of GFP which may be isolated from natural sources or genetically engineered, as well as artificially modified GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered, including but not limited to, yellow fluorescent proteins (YFP), red fluorescent proteins (RFP), cyan fluorescent proteins (CFP), blue fluorescent proteins, luciferin, UV excitable fluorescent proteins, or any wave-length in between. As used herein, "GFP" shall mean all fluorescent proteins known in the art.

"GPCR signaling" means GPCR induced activation of G proteins. This may result in, for example, cAMP production.

"G protein-coupled receptor kinase" (GRK) includes any kinase that has the ability to phosphorylate a GPCR.

"*Homo sapien* GPCR" means a naturally occurring GPCR in a *Homo sapien*.

"Hybridization" means hydrogen bonding, which may be Watson-Crick, Hoogsteen or reversed Hoogsteen hydrogen bonding, between complementary nucleoside or nucleotide bases. For example, adenine (A) and thymine (T) are complementary nucleobases which pair through the formation of hydrogen bonds.

"Inverse agonist" means a compound which, upon binding to the GPCR, inhibits the basal intrinsic activity of the GPCR. An inverse agonist is a type of antagonist.

An "isolated" or "purified" GPCR nucleic acid molecule or protein, biologically active portion thereof, or antibody is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5 and 3 ends of the nucleic acid) in the genomic DNA of the organism from which the nucleic acid is derived. For purposes of the invention, "isolated" when used to refer to nucleic acid molecules, excludes isolated chromosomes. For example, in various embodiments, the isolated GPCR nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An GPCR protein that is substantially free of cellular material includes preparations of GPCR protein having less than about 30%, 20%, 10%, or 5% (by dry weight) of non-GPCR protein. When the GPCR protein or biologically active portion thereof is recombinantly produced, preferably, culture medium represents less than about 30%, 20%, 10%, or 5% of the volume of the protein preparation. When GPCR protein is produced by chemical synthesis, preferably the protein preparations have less than about 30%, 20%, 10%, or 5% (by dry weight) of chemical precursors or non-GPCR chemicals.

"Modified GPCR" refers to a GPCR that has one or more modifications resulting in a constitutively desensitized GPCR. As such, a modified GPCR may have one or additions, substitutions, or deletions of its amino acid sequence, preferably in its DRY motif.

"Modified GPCR probe" means a probe that binds specifically across the modified DRY region of nucleic acids encoding those polypeptides.

"Modified DRY motif" refers to a DRY motif of a GPCR that has one or modifications resulting in an amino acid sequence other than the DRY motif. This modified DRY motif results in a constitutively desensitized GPCR. Most preferably, the modified DRY motif consists of an amino acid other than arginine as the second amino acid. The second amino acid of the DRY motif is preferably Alanine, Aspartate, Glutamate, Histidine, or Asparagine, but may be any amino acid other than Arginine or Lysine, as shown in FIG. 2b.

"Modified GRK" means a GRK modified such that it alters desensitization.

"Naturally occurring GPCR" means a GPCR that is present in nature.

"Odorant ligand" means a ligand compound that, upon binding to a receptor, leads to the perception of an odor including a synthetic compound and/or recombinantly produced compound including agonist and antagonist molecules.

"Odorant receptor" means a receptor protein normally found on the surface of olfactory neurons which, when activated (normally by binding an odorant ligand) leads to the perception of an odor.

A "modified odorant receptor" will be those odorant receptors that contain a DRY mutation.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

An "origin of replication" refers to those DNA sequences that participate in DNA synthesis.

The phrase "pharmaceutically acceptable" refers to molecular entities and compositions that are physiologically tolerable and do not typically produce an allergic or similar untoward reaction, such as gastric upset, dizziness and the like, when administered to a human.

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Primatized antibody" means a recombinant antibody containing primate variable sequences or antigen binding portions, and human constant domain sequences.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

"Presently" means as a temporal context placing sensitization, desensitization, or resensitization in a time context.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A "replicon" is any genetic element (e.g., plasmid, chromosome, virus) that functions as an autonomous unit of DNA replication in vivo; i.e., capable of replication under its own control.

"Resensitized GPCR" means a GPCR, which was previously desensitized, which is presently sensitized.

"Resensitization active compounds" are compounds which result in resensitization of a GPCR.

"Sensitized GPCR" means a GPCR that presently has ability to respond to agonist and activate conventional G protein signaling.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Therapeutically effective amount" is meant an amount sufficient to prevent, and preferably reduce some feature of pathology such as for example, elevated blood pressure, respiratory output, etc.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

"Unknown or Orphan Receptor" means a GPCR whose function and/or ligands are unknown.

A "modified orphan receptor" means those orphan receptors that contain a DRY mutation.

A "vector" is a replicon, such as plasmid, phage or cosmid, to which another DNA segment may be attached so as to bring about the replication of the attached segment.

The invention features modified GPCR polypeptides comprising a modified DRY motif, preferably a substantially pure preparation of a modified GPCR polypeptide comprising a modified DRY motif, or a recombinant modified GPCR polypeptide comprising a modified DRY motif. In preferred embodiments: the polypeptide has biological activity; the polypeptide has an amino acid sequence at least about 60%, 70%, 80%, 90%, 95%, 98%, or 99% identical to an amino acid sequence of the invention contained in the Sequence Listing, preferably it has about 65% sequence identity with an amino acid sequence of the invention contained in the Sequence Listing, and most preferably it has about 92% to about 99% sequence identity with an amino acid sequence of the invention contained in the Sequence Listing; the polypeptide has an amino acid sequence essentially the same as an amino acid sequence of the invention contained in the Sequence Listing; the polypeptide is at least about 5, 10, 20, 50, 100, or 150 amino acid residues in length; the polypeptide includes at least about 5, preferably at least about 10, more preferably at least about 20, still more preferably at least about 50, 100, or 150 contiguous amino acid residues of the invention contained in the Sequence Listing. In yet another preferred embodiment, the amino acid sequence which differs in sequence identity by about 7% to about 8% from the amino acid sequences of the invention contained in the Sequence Listing is also encompassed by the invention.

In preferred embodiments: the modified GPCR polypeptide comprising a modified DRY motif is encoded by a nucleic acid of the invention contained in the Sequence Listing, or by a nucleic acid having at least about 60%, 70%, 80%, 90%, 95%, 98%, or 99% homology with a nucleic acid of the invention contained in the Sequence Listing.

In a preferred embodiment, the subject modified GPCR polypeptide comprising a modified DRY motif differs in amino acid sequence at about 1, 2, 3, 5, 10 or more residues from a sequence of the invention contained in the Sequence Listing. The differences, however, are such that the modified GPCR polypeptide comprising a modified DRY motif still exhibits a constitutively desensitized biological activity.

In preferred embodiments, the polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

Polypeptides of the invention include those which arise as a result of alternative transcription events, alternative RNA splicing events, and alternative translational and posttranslational events.

In a preferred embodiment, the encoded modified GPCR polypeptide comprising a modified DRY motif differs (e.g., by amino acid substitution, addition or deletion of at least one amino acid residue) in amino acid sequence at about 1, 2, 3, 5, 10 or more residues, from a sequence of the invention contained in the Sequence Listing. The differences, however, are such that: the encoded GPCR polypeptide comprising a modified DRY motif still exhibits a constitutively desensitized biological activity.

In preferred embodiments, the encoded polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

Included in the invention are: allelic variations; natural mutants; induced mutants; proteins encoded by DNA that hybridize under high or low stringency conditions to a nucleic acid which encodes a polypeptide of the invention contained in the Sequence Listing (for definitions of high and low stringency see Current Protocols in Molecular Biology, John Wiley & Sons, New York, 1989, 6.3.1–6.3.6, hereby incorporated by reference); and, polypeptides specifically bound by antisera to GPCR polypeptides comprising a modified DRY motif, especially by antisera to an active site or binding domain of modified GPCR polypeptides comprising a modified DRY motif polypeptide. The invention also includes fragments, preferably biologically active fragments. These and other polypeptides are also referred to herein as modified GPCR polypeptide analogs or variants.

The invention further provides nucleic acids, e.g., RNA or DNA, encoding a polypeptide of the invention. This includes double stranded nucleic acids as well as coding and antisense single strands.

In preferred embodiments, the subject nucleic acid encoding the modified GPCRs comprising a modified DRY motif will include a transcriptional regulatory sequence, e.g., at least one of a transcriptional promoter or transcriptional enhancer sequence, operably linked to the gene sequence of the modified GPCR comprising a modified DRY motif, e.g., to render the gene sequence encoding the modified GPCR comprising a modified DRY motif suitable for expression in a recombinant host cell.

In yet a further preferred embodiment, the nucleic acid which encodes a modified GPCR polypeptide comprising a modified DRY motif of the invention, hybridizes under stringent conditions to a nucleic acid probe corresponding to at least about 8 consecutive nucleotides, comprising the modified DRY motif, of the invention contained in the Sequence Listing; more preferably to at least about 12 consecutive nucleotides of the invention contained in the Sequence Listing; still more preferably to at least about 20 consecutive nucleotides of the invention contained in the Sequence Listing; most preferably to at least about 40 consecutive nucleotides of the invention contained in the Sequence Listing.

In another aspect, the invention provides a substantially pure nucleic acid having a nucleotide sequence which encodes a modified GPCR polypeptide comprising a modified DRY motif. In preferred embodiments: the encoded polypeptide has biological activity; the encoded polypeptide has an amino acid sequence at least about 60%, 70%, 80%, 90%, 95%, 98% or 99% homologous to an amino acid sequence of the invention contained in the Sequence Listing; the encoded polypeptide has an amino acid sequence essentially the same as an amino acid sequence of the invention contained in the Sequence Listing; the encoded polypeptide is at least about 5, 10, 20, 50, 100, or 150 amino acids in length; the encoded polypeptide comprises at least about 5, preferably at least about 10, more preferably at least about 20, still more preferably at least about 50, 100, or 150 contiguous amino acids of the invention contained in the Sequence Listing.

In another aspect, the invention encompasses: a vector including a nucleic acid which encodes a modified GPCR polypeptide comprising a modified DRY motif or a modified GPCR polypeptide comprising a modified DRY motif variant as described herein; a host cell transfected with the vector; and a method of producing a recombinant modified GPCR polypeptide comprising a modified DRY motif or modified GPCR polypeptide comprising a modified DRY motif variant; including culturing the cell, e.g., in a cell culture medium, and isolating a modified GPCR polypeptide comprising a modified DRY motif or variant, e.g., from the cell or from the cell culture medium.

One embodiment of the invention is directed to substantially isolated nucleic acids. Nucleic acids of the invention include sequences comprising at least about 8 nucleotides in length, more preferably at least about 12 nucleotides in length, even more preferably at least about 15–20 nucleotides in length, that correspond to a subsequence of any one of SEQ ID NO: 7–SEQ ID NO: 12 or complements thereof. Alternatively, the nucleic acids comprise sequences contained within any ORF (open reading frame), including a complete protein-coding sequence, of which any of SEQ ID NO: 7–SEQ ID NO: 12 forms a part. The invention encompasses sequence-conservative variants and function-conservative variants of these sequences. The nucleic acids may be DNA, RNA, DNA/RNA duplexes, protein-nucleic acid (PNA), or derivatives thereof.

In another aspect, the invention features a purified recombinant nucleic acid having at least about 50%, 60%, 70%, 80%, 90%, 95%, 98%, or 99% homology with a sequence of the invention contained in the Sequence Listing.

The invention also encompasses recombinant DNA (including DNA cloning and expression vectors) comprising these modified DRY motif-derived sequences; host cells comprising such DNA, including fungal, bacterial, yeast, plant, insect, and mammalian host cells; and methods for producing expression products comprising RNA and polypeptides encoded by the modified GPCR comprising a modified DRY motif sequences. These methods are carried out by incubating a host cell comprising a modified GPCR comprising a modified DRY motif-derived nucleic acid sequence under conditions in which the sequence is expressed. The host cell may be native or recombinant. The polypeptides can be obtained by (a) harvesting the incubated cells to produce a cell fraction and a medium fraction; and (b) recovering the modified GPCR polypeptide comprising a modified DRY motif from the cell fraction, the medium fraction, or both. The polypeptides can also be made by in vitro translation.

In another aspect, the invention features nucleic acids capable of binding mRNA of modified GPCR comprising a modified DRY motif. Such nucleic acid is capable of acting as antisense nucleic acid to control the translation of mRNA of modified GPCRs comprising a modified DRY motif. A further aspect features a nucleic acid which is capable of binding specifically to a modified GPCR polypeptide comprising a modified DRY motif nucleic acid. These nucleic acids are also referred to herein as complements and have utility as probes and as capture reagents.

In another aspect, the invention features an expression system comprising an open reading frame corresponding to the nucleic acid of a modified GPCR comprising a modified DRY motif. The nucleic acid further comprises a control sequence compatible with an intended host. The expression system is useful for making polypeptides corresponding to modified GPCR polypeptide comprising a modified DRY motif nucleic acid.

In another aspect, the invention encompasses: a vector including a nucleic acid which encodes a modified GPCR polypeptide comprising a modified DRY motif or variant as described herein; a host cell transfected with the vector; and a method of producing a recombinant modified GPCR polypeptide comprising a modified DRY motif or variant; including culturing the cell, e.g., in a cell culture medium, and isolating the modified GPCR polypeptide comprising a modified DRY motif or variant, e.g., from the cell or from the cell culture medium.

The invention further provides antibodies, preferably monoclonal antibodies, which specifically bind to the polypeptides of the invention. Methods are also provided for producing antibodies in a host animal. The methods of the invention comprise immunizing an animal with at least one modified GPCR comprising a modified DRY motif-derived immunogenic component, wherein the immunogenic component comprises one or more of the polypeptides encoded by any one of SEQ ID NO: 7–SEQ ID NO: 12 or sequence-conservative or function-conservative variants thereof; or polypeptides that are contained within any ORFs, including complete protein-coding sequences, of which any of SEQ ID NO: 7–SEQ ID NO: 12 forms a part; or polypeptide sequences contained within any of SEQ ID NO: 1–SEQ ID NO: 6; or polypeptides of which any of SEQ ID NO: 1–SEQ ID NO: 6 forms a part. Host animals include any warm blooded animal, including without limitation mammals and birds. Such antibodies have utility as reagents for immunoassays to evaluate the abundance and distribution of modified GPCR comprising a modified DRY motif-specific antigens.

The present invention is related to modified GPCRs, polypeptides of modified GPCRs, nucleic acid molecules that encode the modified GPCRs, vectors containing the nucleic acid molecules which encode the modified GPCRs, vectors enabling the nucleic acid construction of the modified GPCRs, and cells containing modified GPCRs. The invention further relates to assay systems using the modified GPCRs, assay systems using the cells containing modified GPCRs, compounds identified using the assay systems, methods of treatment using the compounds identified, methods of disease diagnosis using the assay systems, and kits containing assay reagents of the present invention and cells of the present invention. The invention also may relate to antisense and treatment techniques using the modified GPCR nucleic acids.

Mutations can be made in the GPCR or modified GPCR such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. The present invention should also be considered to include sequences containing non-conservative changes which do not significantly alter the activity or binding characteristics of the resulting protein.

In a particular embodiment, the modified GPCRs of the present invention include GPCRs that have been modified so that they localize to endocytic vesicles or endosomes in an agonist-independent manner. In a particular embodiment, the modified GPCRs of the present invention include GPCRs that have been modified so that they bind βarrestin in an agonist-independent manner. In a more preferred embodiment, the modified GPCRs of the present invention both bind βarrestin and localize to endocytic vesicles or endosomes.

The modified GPCRs of the present invention comprise a modified DRY motif. A DRY motif is a highly conserved GPCR motif located near the cytoplasmic boundary of the third transmembrane region and the second intracellular loop. The DRY motif is most preferably a three amino acid motif: Aspartate-Arginine-Tyrosine (DRY). A modified DRY motif refers to a DRY motif of a GPCR that has one or modifications resulting in an amino acid sequence other than the DRY motif. Most preferably, the modified DRY motif consists of an amino acid other than arginine as the second amino acid. The second amino acid of the DRY motif is preferably Alanine, Aspartate, Glutamate, Histidine, or Asparagine, but may be any amino acid other than arginine or Lysine.

This modified DRY motif results in a constitutively desensitized GPCR, which was not known prior to the present invention. As described herein, the DRY motif of any GPCR can be modified as described, resulting in a constitutively desensitized GPCR.

The modified GPCRs can include V2R, but V2R may also be excluded. The modified DRY motif of the V2R R137H can be used to replace the DRY motif of other GPCRs. Preferably, this three amino acid sequence is located near the cytoplasmic boundary of the third transmembrane region and the second intracellular loop. Modified GPCRs containing a mutation of the R of the DRY motif have an increased affinity for arrestin and colocalize with arrestin in endocytic vesicles or endosomes in an agonist-independent manner. This invention includes (is related to) modified GPCRs which colocalize with arrestin in endocytic vesicles or endosomes in an agonist-independent manner, preferably due to a mutation of R of the DRY motif.

The modified GPCRs of the present invention may also include modifications to include one or more sites of phosphorylation, preferably clusters of phosphorylation sites, properly positioned in their carboxyl terminal tails, as described in U.S. Ser. No. 09/993,844 "Modified G-Protein Coupled Receptor," filed Nov. 5, 2001, the contents of which are hereby incorporated by reference in their entirety. The clusters of amino acids may occupy two out of two, two out of three, three out of three, three out of four positions, four out of four, four out of five positions, five out of five, and the like consecutive amino acid positions. These clusters of phosphorylation sites are preferably serine and threonine residues located in the carboxyl-terminal tail of the GPCR. These modifications may be made by discrete point mutations of the amino acid residues, mutations made in the nucleic acid sequence of a GPCR, or by exchanging the carboxyl-terminal tail, in whole or in part, with that of a GPCR having properly positioned clusters of phosphorylation sites. The site of exchange may be after or including the conserved NPXXY motif. As an alternative, a putative site of palmitoylation of a GPCR may be identified at approximately 10 to 25 (preferably 15 to 20) amino acid residues downstream of the conserved NPXXY motif, and the site of exchange may be after or including the palmitoylated cysteine(s). The tails may be exchanged and the modified GPCRs may be constructed accordingly by manipulation of the nucleic acid sequence or the corresponding amino acid sequence.

The modified GPCRs of the present invention are useful in assays for screening compounds that may alter G protein-coupled receptor (GPCR) activity. These assays may utilize detectable molecules conjugated to arrestin, GPCR, or other proteins involved in desensitization. Detectable molecules are described herein, and include fluorescent groups (for example, GFP), enzymes (for example, β-galactosidase), radioisotopes, epitope tags, affinity labels, and chemiluminescent groups. Examples of assays in which the present invention may be used include, but are not limited to, those as described in U.S. Pat. Nos. 5,891,646 and 6,110,693, the disclosures of which are hereby incorporated by reference in their entireties. Additional examples of assays in which the present invention may be used include, but are not limited to, assays using chemiluminescence, Fluorescent Resonance Energy Transfer (FRET) and assays using Bioluminescence Resonance Energy Transfer (BRET) technology as described in Angers, S., Salahpour, A., Joly, E., Hilairet, S., Chelsky, "β2-adrenergic receptor dimerization in living cells using bioluminescence resonance energy transfer (BRET)," *Proc. Natl, Acad. Sci.* USA 97, 7: 3684–3689.

An illustrative, non-limiting list of known GPCRs with which the present invention may be used is contained in FIG. 1. The receptors are grouped according to classical divisions based on structural similarities and ligands.

By way of example, the major classes of GPCRs for known receptors are Class A receptors which preferably do target to endocytic vesicles or endosomes in HEK-293 cells, and Class B receptors which preferably do not target to endocytic vesicles or endosomes in HEK-293 cells.

It has been discovered that after agonists bind GPCRs, G-protein coupled receptor kinases (GRKs) phosphorylate intracellular domains of GPCRs. After phosphorylation, an arrestin protein associates with the GRK-phosphorylated receptor and uncouples the receptor from its cognate G protein. The interaction of the arrestin with the phosphorylated GPCR terminates GPCR signaling and produces a non-signaling, desensitized receptor.

The arrestin bound to the desensitized GPCR targets the GPCR to clathrin-coated pits for endocytosis by functioning as an adaptor protein, which links the GPCR to components of the endocytic machinery, such as adaptor protein-2 (AP-2) and clathrin. The internalized GPCRs are dephosphorylated and are recycled back to the cell surface desensitized. The present inventors have determined that the stability of the interaction of arrestin with the GPCR dictates the rate of GPCR dephosphorylation, recycling, and resensitization. The involvement of GPCR phosphorylation and dephosphorylation in the desensitization process has been exemplified in U.S. Ser. No. 09/933,844, filed Nov. 5, 2001, the disclosure of which is hereby incorporated by reference in its entirety.

The present inventors have discovered that the dependence on agonist, of the arrestin association with the GPCR, may be mediated by the DRY motif of the GPCR. The DRY motif may allow arrestin-GPCR association dependence on agonist.

GPCRs, which normally bind arrestin in an agonist-dependent manner, may be modified to comprise a modified DRY motif. This modification preferably allows the modified GPCR to bind arrestin in the absence of agonist. These modified GPCRs may be useful in screening for antagonists of GPCR activity.

GPCRs have been implicated in a number of disease states, including, but not limited to cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer. As such, modulation of GPCR activity and affinity for arrestin is a mechanism for ameliorating these disease states.

The present inventors have determined that a conserved abnormality(ies) in any part of the GPCR signaling pathway may cause abnormal GPCR signaling leading to a GPCR-related disease. For example, components of the GPCR signaling pathway, including but not limited to, GPCRs, GRKs, arrestins, protein phosphatases, AP-2 proteins, clathrin, and the like, may express a mutation(s). The mutation(s) may result in, for example, abnormal ligand binding, G protein coupling, GPCR trafficking, and the like, that may cause altered GPCR signaling. These mutations may result in a GPCR that is constitutively desensitized.

A wild-type GPCR cycles between being (1) sensitized, which means presently able to respond to agonist and activate conventional G protein signaling, (2) desensitized, which means presently unable to respond to agonist and activate conventional G protein signaling, and (3) resensitized, which means again presently able to respond to agonist and activate conventional G protein signaling. This balance can be disrupted, resulting, for example, in a constitutively desensitized GPCR. A constitutively desensitized GPCR does not cycle as above. Under wild-type conditions, a GPCR is desensitized subsequent to agonist activation of the sensitized GPCR; whereas, a constitutively desensitized GPCR forms independent of agonist stimulation of the sensitized GPCR. The constitutively desensitized GPCRs of the present invention are most preferably localized in endocytic vesicles or endosomes.

As described herein, the constitutively desensitized GPCRs can be associated with a diseased state. These constitutively desensitized GPCRs do not properly respond to agonist and do not activate conventional G protein signaling. This lack of conventional G protein signaling may be responsible for the diseased state. These constitutively desensitized GPCRs may be constitutively phosphorylated and constitutively bind arrestin. The arrestin binding may result in the GPCR localizing in the endocytic vesicles or endosomes.

Certain conditions can alter the constitutive desensitization of these receptors. Some of these conditions may result in desensitized receptors. Some of the conditions may result in the reversal of the relevant disease state.

For example, mutant receptors which are constitutively desensitized can harbor second mutations which prevent constitutive desensitization, particularly endosomal localization. By way of example, a modified GPCR may have additional mutations, wherein phosphorylation sites (for example, SSSTSS) are converted to non-phosphorylatable sites (for example, AAAAAA) in its carboxyl-terminal tail, that result in decreased βarrestin binding and prevent constitutive desensitization, particularly endosomal localization of the GPCR (FIG. 8). Mutant proteins in the desensitization pathway can inhibit the constitutive desensitization of the modified GPCR and its localization in endocytic vesicles or endosomal localization. (FIG. 14). Antagonists of the GPCR can prevent the constitutive desensitization, particularly endosomal localization (FIGS. 14 and 15). Compounds which bind other proteins, involved in the desensitization pathway, can also prevent the constitutive desensitization, particularly endosomal localization.

By way of example, a GPCR may have a modification(s) in any part of the GPCR including, but not limited to, in the carboxyl-terminal tail, in the intracellular loop(s), and/or in the cytoplasmic end of the transmembrane region. This modification may, for example, enhance the GPCR affinity for arrestin. If the GPCR affinity for arrestin is sufficiently enhanced by the mutation, the GPCR may become constitutively desensitized. A constitutively desensitized receptor may contribute to the etiology of a GPCR-related disease.

Arrestin also may have a modification(s) in any part thereof that either enhances or reduces the affinity of the arrestin for the GPCR. In addition, AP-2 protein and clathrin may have a modification in any part thereof that either enhances or reduces the ability of arrestins bound to a receptor to remain bound. The altered affinity of arrestin for the GPCR may lead to a constitutively desensitized GPCR, and thus, contribute to the etiology of a GPCR-related disease. Additionally, the expression of arrestin may be increased with respect to wild-type, leading to a constitutively desensitized GPCR.

Further, G protein-coupled receptor kinases (GRKs) may have a modification in any part thereof that either enhances phosphorylation of a GPCR, leading to enhanced affinity of the GPCR for arrestin. The modified GRK may lead to constitutive desensitization, and thus, contribute to the etiology of a GPCR-related disease. Additionally, the expression of GRKs may be increased with respect to wild-type, leading to a constitutively desensitized GPCR.

In addition, protein phosphatases may have a modification (e.g., genetic mutation or other functional alteration) in any part thereof that either enhances or reduces dephosphorylation of a GPCR, leading to enhanced or reduced affinity of the GPCR for arrestin. The modification in the protein phosphatases may lead to constitutive desensitization, and thus contribute to the etiology of a GPCR-related disease. Protein phosphatases that may be involved in the GPCR signaling pathway, include, for example, calcium regulated serine threonine phosphatases. Examples of Ca-regulated serine threonine phosphatases include the PPEF1/PPEF2 family of phosphatases.

In a particular embodiment, the modified GPCRs of the present invention include GPCRs that have been modified so that a percentage greater than basal levels localize to endocytic vesicles or endosomes in absence of agonist stimulation.

Modified GPCRs

The present invention is related to modified GPCRs. Most preferably, the modified GPCRs of the present invention are modified such that they constitutively localize in endocytic vesicles or endosomes. Normally, agonist binds GPCR, the activated GPCR is phosphorylated, binds arrestin, and is targeted to endocytic vesicles or endosomes. The phosphorylated domain may be in the carboxyl-terminal domain. The present inventors determined that modifications in regions of the GPCR other than the carboxyl-terminal domain can control the binding of the GPCR to arrestin. They determined that modifications can enable GPCR binding to arrestin in the absence of agonist. Modifications can form a constitutively desensitized receptor.

The present inventors have discovered that specific amino acid motifs may be involved in agonist-dependent formation of a GPCR/arrestin complex, and thus ultimately may promote recruitment of arrestin to endocytic vesicles or endosomes. Modification of these amino acid motifs may alleviate the agonist-dependence of the formation of the GPCR/arrestin complex. Most preferably, the amino acid motif involved in agonist-dependent formation of a GPCR/arrestin complex may be the DRY motif.

Most preferably, the modified GPCRs of the present invention comprise one or more modifications in the DRY motif. The DRY motif may be modified in 1, 2, or 3 of 3 amino acids, but must be modified at least in the Arginine. The DRY motif may be modified in whole or in part. A DRY motif is a highly conserved GPCR motif located near the cytoplasmic boundary of the third transmembrane region and the second intracellular loop. The DRY motif is most preferably a three amino acid motif: Aspartate-Arginine-Tyrosine (DRY). Modifications of this motif can form a constitutively desensitized receptor.

By way of example, as shown in FIG. 3, the V2R has a DRY motif at amino acids 136–138. Modifications of the DRY motif may promote agonist-independent formation of a GPCR/arrestin complex and constitutive localization to the endocytic vesicles or endosomes. The $\alpha_{1B}$-AR receptor comprises a DRY motif at amino acids 142–144 that promotes formation of a GPCR/arrestin complex and localizes to endocytic vesicles or endosomes. The $AT_{1A}R$ receptor comprises a DRY motif at amino acids 125–127 that also promotes formation of a GPCR/arrestin complex and localizes to the endocytic vesicles or endosomes.

The present invention includes the polypeptide sequences of these modified GPCRs. The modified GPCRs of the present invention include GPCRs that have been modified in the DRY motif to localize to endocytic vesicles or endosomes in an agonist-independent manner. The polypeptide sequences of the modified GPCRs of the present invention include sequences having one or more additions, deletions, substitutions, or mutations. These mutations are preferably substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention should be considered to include sequences containing conservative changes which do not significantly alter the activity or binding characteristics of the resulting protein. The present invention should also be considered to include sequences containing non-conservative changes which do not significantly alter the activity or binding characteristics of the resulting protein.

The present invention further includes isolated nucleic acid molecules that encode modified GPCRs. It should be appreciated that also within the scope of the present invention are DNA sequences encoding modified GPCRs which code for a modified GPCR having the same amino acid sequence as the modified GPCRs, but which are degenerate. By "degenerate" it is meant that a different three-letter codon is used to specify a particular amino acid.

To create a modified GPCR containing a modified DRY motif according to the present invention, a GPCR comprising a DRY motif may have one or more additions, substitutions, deletions, or mutations of amino acid residues in its DRY motif such that the modified GPCR is a constitutively desensitized receptor. By way of example, discrete point mutations of the amino acid residues may be made to provide a modified GPCR. By way of example, three consecutive amino acids may be mutated to provide a modified GPCR. By way of example, the Arginine may be mutated to any amino acid other than Lysine, most preferably Alanine, Glutamate, Aspartate, Asparagine, or Histidine, to provide a modified GPCR.

In addition, to create a modified GPCR containing a modified DRY motif, mutations may be made in a nucleic acid sequence of a GPCR such that a particular codon is changed to a codon which codes for a different amino acid. Such a mutation is generally made by making the fewest nucleotide changes possible. A substitution mutation of this sort can be made to change an amino acid in the resulting protein to create a modified DRY motif forming a constitutively desensitized receptor. Also by way of example, discrete point mutations of the nucleic acid sequence may be made.

Furthermore, to provide modified GPCRs of the present invention, a GPCR which binds arrestin in an agonist-dependent manner may also have its DRY motif, in whole or in part, exchanged with that of a GPCR having a modified DRY motif that forms a constitutively desensitized receptor. Preferably, the DRY motif of a GPCR which binds arrestin in an agonist-dependent manner is exchanged at an amino acid residue in close proximity to the DRY motif.

Modified GPCRs may be generated by molecular biological techniques standard in the genetic engineering art, including but not limited to, polymerase chain reaction (PCR), restriction enzymes, expression vectors, plasmids, and the like. By way of example, vectors may be designed to enhance the agonist-independent affinity of a GPCR for arrestin. PCR amplified DNA fragments of a GPCR to be modified may be digested by appropriate restriction enzymes and subcloned into the vector, such as pcDNA3.1/ zeo or pEGFP-N3. Modifications of the DNA may be introduced by standard molecular biological techniques as described above.

As may be shown by standard receptor binding assays, the modified GPCRs are essentially indistinguishable from their wild-type counterparts except for an agonist-independent affinity for arrestin, and thus, constitutive endosomal localization. For example, the modified GPCRs possess similar affinity for antagonists or inverse agonists, and the like.

Figure 5:
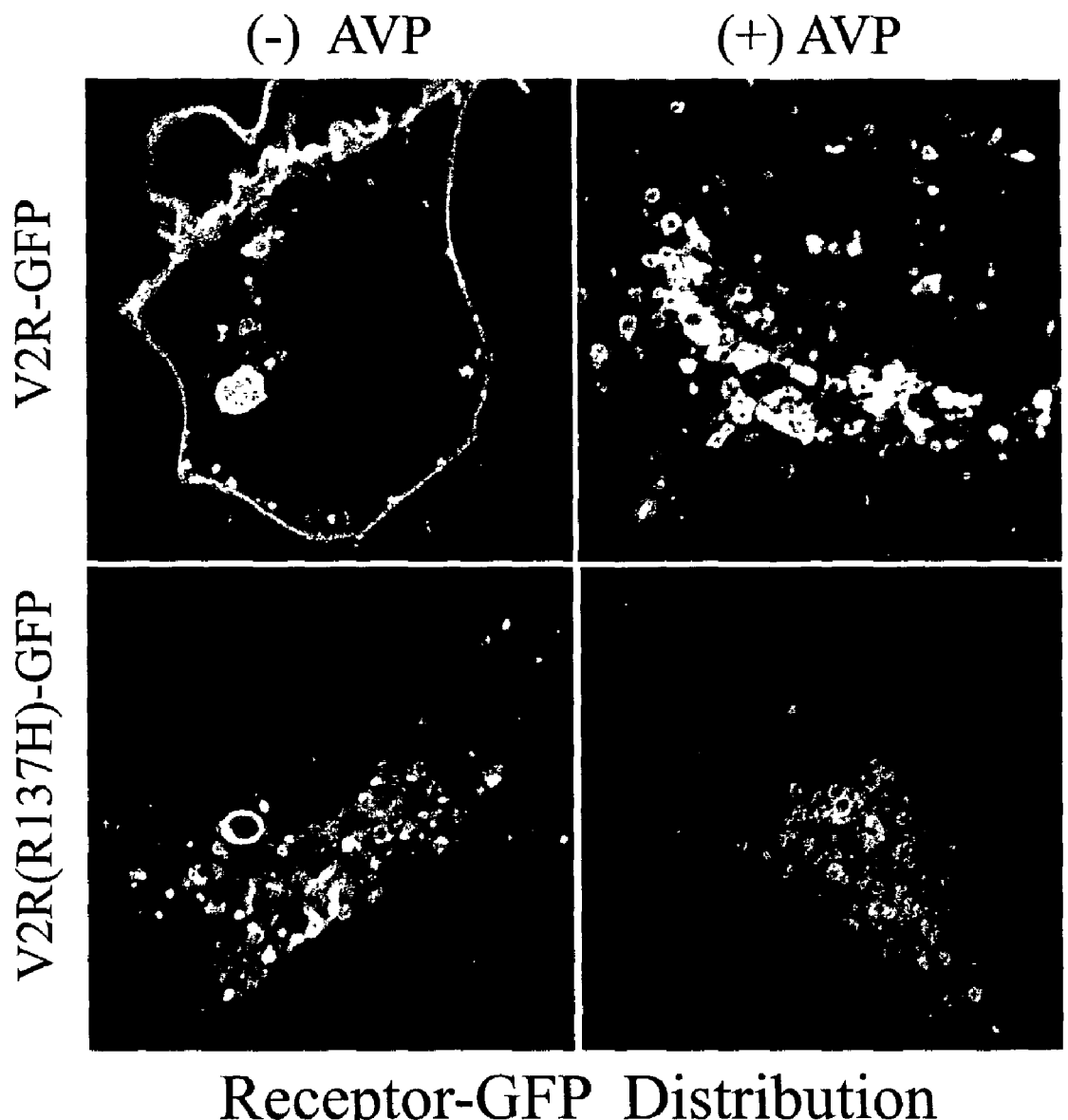
FIG. 5 illustrates the fluorescence images of V2R-GFP and V2R(R137H)-GFP in HEK-293 cells. Cells expressing V2R-GFP (Upper) or V2R(R137H)-GFP (Lower) were treated with vehicle or AVP for 30 min. at 37° C. The agonist-mediated redistribution of wild-type receptor (Upper) from the plasma membrane to endocytic vesicles contrasts with the agonist-independent localization of the V2R (R137H)-GFP in endosomes (Lower). Bar=25 μm.

By way of example, V2R may have a modification R137H (FIG. 3) resulting in modified endocytic targeting as shown in FIG. 5. This modified V2R may be implicated in nephrogenic diabetes insipidus (NDI).

Methods of Assaying GPCR Activity

The modified GPCRs of the present invention are useful in methods of assaying GPCR activity. The modified GPCRs of the present invention may be used in assays to study GPCRs that have stronger than desired interactions or associations with arrestins and GPCRs that have unknown interactions or associations with arresting. Methods of the present invention that use the modified GPCRs provide a sensitive assay and may provide for enhanced detection, for example, of arrestin/GPCRs in endocytic vesicles or endosomes. The assays using the modified GPCRs of the present invention may be useful for screening compositions, compounds, sample solutions, and the like for antagonists, inverse agonists, desensitization active compounds, resensitization active compounds, and the like. Once identified, these compounds may be useful as drugs capable of modulating GPCR activity and useful in the treatment of one or more of the disease states in which GPCRs have been implicated.

In a preferred assay according to the present invention, cells are provided that express modified GPCRs of the present invention and these cells may further contain a conjugate of an arrestin and a detectable molecule.

Arrestin coupled to a detectable molecule may be detected and monitored as it functions in the GPCR pathway. The location of the arrestin may be detected, for example, evenly distributed in the cell cytoplasm, concentrated at a cell membrane, concentrated in clathrin-coated pits, localized in endocytic vesicles or endosomes, and the like. The proximity of arrestin to a GPCR may be monitored, as well as the proximity to any other cell structure. The change in this proximity in the presence of antagonist can be analyzed. For example, in response to antagonist arrestin may be detected in proximity to GPCRs at a cell membrane, concentrated with GPCRs in clathrin-coated pits, colocalized with a GPCR on endocytic vesicles or endosomes, and the like.

Preferably, the modified GPCRs of the present invention have an increased affinity for arrestin in the absence of agonist and provide a stable complex of the modified GPCR with arrestin, and thereby promote colocalization of the modified GPCR with arrestin into endocytic vesicles or endosomes in the absence of agonist. In the methods of assaying of the present invention, arrestin may be detected, for example, in the cytoplasm, concentrated in proximity to modified GPCRs at a cell membrane, concentrated in proximity to modified GPCRs in clathrin-coated pits, colocalized with a modified GPCR on endocytic vesicles or endosomes, and the like. Preferably the arrestin may be detected colocalized with a GPCR on endocytic vesicles or endosomes. Preferably, compounds may alter this colocalization of arrestin with a GPCR on endocytic vesicles or endosomes.

The association of arrestin with a modified GPCR on endocytic vesicles or endosomes may be detected in absence of agonist. The colocalization of arrestin with a modified GPCR on endocytic vesicles or endosomes may be disrupted in the presence of antagonist. The association of arrestin with GPCRs on endocytic vesicles or endosomes may give a strong, readily recognizable signal. Under magnification of 40× objective lens, the signal may be doughnut-like in appearance. The signal resulting from the compartmentalization of arrestin and GPCR colocalized in endocytic vesicles or endosomes is typically easy to detect. Similarly, blocking this association is easy to detect. Examples of detection methods are described herein. Such methods include, for example, polarization microscopy, BRET, FRET, evanescent wave excitation microscopy, and standard or confocal microscopy.

The methods of assessing GPCR pathway activity of the present invention may comprise (a) preparing a modified GPCR or biologically active fragment thereof which targets to an endocytic vesicle or endosome without agonist, (b) attaching the modified GPCR or biologically active fragment thereof to a substrate, (c) exposing the modified GPCR or biologically active fragment thereof to an arrestin, and (e) determining the interaction of the modified GPCR with arrestin.

The methods of assessing GPCR pathway activity may comprise (a) preparing a modified GPCR or biologically active fragment thereof, (b) expressing the modified GPCR or biologically active fragment in a cell that comprises arrestin, and (c) determining the interaction of the modified GPCR with arrestin.

The methods of assessing GPCR pathway activity may comprise (a) preparing a modified GPCR or biologically active fragment thereof, (b) detecting cellular localization of GPCR within the cell.

The arrestin may be in proximity to the modified GPCR. The arrestin, the modified GPCR, and/or the arrestin/modified GPCR complex may be detected, for example, in endocytic vesicles or endosomes, in clathrin-coated pits, concentrated in proximity to a cell membrane, and the like. Preferably, the arrestin, the modified GPCR, and/or the arrestin/modified GPCR complex may be detected in endocytic vesicles or endosomes. The arrestin, the modified GPCR, and/or the arrestin/modified GPCR complex thus may be detected in endocytic vesicles or endosomes absence of agonist. The association of arrestin with a GPCR in endocytic vesicles or endosomes may give a strong, readily recognizable signal that persists for extended periods of time.

The modified GPCRs of the present invention can be used to screen for second site mutations which prevent endosomal localization and may be relevant for disease modulation. Mutant GPCRs which are constitutively desensitized can harbor second site mutations which prevent constitutive endosomal localization. By way of example, a mutant receptor may also have a mutation in its carboxyl-terminal tail, such as SSSTSS mutated to AAAAAA, that results in decreased βarrestin binding and results in prevention of constitutive endosomal localization (FIG. 8). The methods for identifying second site suppressor mutations in the GPCRs comprise (a) preparing a modified GPCR or biologically active fragment thereof; (b) expressing said modified GPCR or biologically active fragment thereof in a cell that expresses arrestin; (c) exposing said cell to mutagens; (d) detecting location of the GPCR within the cell, and determining whether the mutagen inhibits endosomal localization of the GPCR, and (e) identifying the second site mutation. The methods for identifying second site suppressor mutations in the GPCRs comprise (a) preparing a modified GPCR or biologically active fragment thereof comprising additional mutations generated by standard molecular biological techniques such as PCR; (b) expressing said modified GPCR or biologically active fragment thereof in a cell that comprises arrestin; (c) detecting location of the mutated GPCR within the cell, and determining whether the mutation inhibits endosomal localization of the GPCR, and (e) identifying the second site mutation. This approach may also be used for the identification of second site suppressors in proteins implicated in the GPCR desensitization pathway, such as, for example, GRKs, βarrestin, and the like.

Mutant proteins in the desensitization pathway may be identified in the above screen. For example, mutant proteins in the endocytosis pathway can prevent the constitutive endosomal localization. By way of example, a dynamin (K44A) mutant prevents constitutive endosomal localization of the desensitized receptors, which, in the presence of wild-type dynamin, constitutively localize in endosomes (FIG. 14).

Preferably, the arrestin and/or the GPCR are conjugated to a detectable molecule, as described herein.

Methods of Screening

The modified GPCRs of the present invention may be used to screen compositions, compounds, sample solutions, chemical libraries, combinatorial libraries, mimetic libraries, immunoglobulins and the like for antagonists, inverse agonists, agents that interfere with constitutive endosomal localization of the modified GPCR, and the like. The modified GPCRs accordingly enable screening for the above agents in the absence of agonist. By way of example, FIGS. 14 and 15 illustrate antagonist interfering with constitutive endosomal localization of the GPCR. Likewise, other antagonists and the like could be identified accordingly.

The methods of assessing GPCR pathway activity of the present invention may comprise (a) preparing a modified GPCR or biologically active fragment thereof thereof which targets to an endocytic vesicle or endosome without agonist, (b) attaching the modified GPCR or biologically active fragment thereof to a substrate, (c) exposing the modified GPCR or biologically active fragment thereof to a candidate compound, (d) exposing said modified GPCR or biologically active fragment thereof to an arrestin (or biologically active fragment thereof), and (e) determining if arrestin binding is blocked by said candidate compound.

The methods of identifying compounds that interfere with agonist-independent arrestin binding to a modified GPCR, may comprise (a) preparing a modified GPCR or biologically active fragment thereof, (b) expressing said modified GPCR or biologically active fragment thereof in a cell that comprises arrestin, (c) exposing the cell to a candidate compound, (d) detecting cellular localization of arrestin within the cell, and determining whether the candidate compound interferes with endosomal localization of arrestin.

The methods of identifying compounds that interfere with agonist-independent endosomal localization of the modified GPCR, may comprise (a) preparing a modified GPCR or biologically active fragment thereof; (b) expressing said modified GPCR or biologically active fragment thereof in a cell that comprises arrestin; (c) exposing the cell to a candidate compound; (d) detecting location of the modified GPCR within the cell, and determining whether the candidate compound interferes with endosomal localization of the modified GPCR.

Preferably, the arrestin and/or the modified GPCR are conjugated to a detectable molecule, as described herein.

By way of example, compounds and sample solutions may be screened for GPCR antagonist or inverse agonist activity using the modified GPCRs of the present invention. Cells that express at least one modified GPCR of the present invention and that further comprise a conjugate of an arrestin and a detectable molecule are provided. The cells are exposed to compositions to be tested. It is detected whether exposure to the compound interferes with endosomal localization of the arrestin or modified GPCR, interference being an indication that the composition has GPCR antagonist or inverse agonist activity. The modified GPCR may also be conjugated to a detectable molecule, preferably at the carboxyl-terminus. As explained above, modifications to GPCRs as in the present invention should not affect the natural affinity of the GPCR for antagonists or inverse agonists.

Further by way of example, compounds, compositions, and sample solutions may be screened for GPCR resensitization activity using the modified GPCRs of the present invention. First cells that express at least one first modified GPCR of the present invention and that further comprise a conjugate of an arrestin and a detectable molecule are provided. The first cells are exposed to compounds or sample solutions to be tested. It is detected whether interaction of the arrestin with the first modified GPCR is decreased after exposure to the composition. For compositions which decrease the interaction of the arrestin with the first modified GPCR, the cell and solution are then exposed to the known agonist or ligand of the receptor. It is then determined whether interaction of the arrestin with the first modified GPCR is increased after exposure to agonist or ligand, indicating that the composition has resensitization activity. Interaction of the arrestin with the modified GPCR may be detected in endocytic vesicles or endosomes, in clathrin-coated pits, in proximity to a cell membrane, and the like, as would be known in the art. Then second cells that express at least one second modified GPCR of the present invention and that further comprise a conjugate of an arrestin and a detectable molecule are provided. The second modified GPCR is not related to the first modified GPCR. The second cells are exposed to the compositions to be tested. It is detected whether interaction of the arrestin with the second modified GPCR is decreased or not after exposure to the composition. For compositions which decrease the interaction of the arrestin with the second modified GPCR, the cell and solution are then exposed to the known agonist or ligand of the receptor; an increase in interaction being an indication that the composition has GPCR resensitization activity independent of the GPCR expressed. Interaction of the arrestin with the modified GPCR may be detected in endocytic vesicles or endosomes, in clathrin-coated pits, in proximity to a cell membrane, and the like. Preferably, the first detection step detects interaction of the arrestin with the modified GPCR in endocytic vesicles or endosomes, the second detection step detects interaction of the arrestin with the modified GPCR in clathrin-coated pits or in proximity to a cell membrane, and the third detection step detects interaction of the arrestin with the modified GPCR in endocytic vesicles or endosomes.

In addition to compounds that target the GPCRs directly (as shown in FIGS. 14 and 15). Compounds which target other proteins involved in the desensitization pathway can also prevent constitutive desensitization, particularly the localization to endocytic vesicles or endosomes. By way of example, a compound which inhibits dynamin would prevent constitutive endosomal localization of the desensitized receptors, which in the absence of a dynamin inhibitor, and constitutively localize in endosomes. The above dynamin inhibitor may mimic the effects of the dynamin(K44A) mutant, which demonstrates the functioning of such inhibitor.

Cell Free Assays

A modified GPCR or biologically active fragment thereof can be analyzed in cell free assays.

In cell-free assays of the present invention, a substrate having deposited thereon a modified GPCR of the present invention is provided. A fluid containing a conjugate of an arrestin and a detectable molecule may also be provided.

The modified GPCR and arrestin may be obtained from whole cells and used in the cell-free assay after purification. The modified GPCR has arrestin binding sites and may be supported in a multilayer or bilayer lipid vesicle. The vesicle supporting the modified GPCR may be deposited on the substrate, and the modified GPCR may be supported in the lipid vesicle and deposited on the substrate such that the arrestin binding sites are exposed to arrestin. The substrate may be any artificial substrate on which the modified GPCR may be deposited, including but not limited to, glass, plastic, diamond, ceramic, semiconductor, silica, fiber optic, biocompatible monomer, biocompatible polymer, polymer beads (including organic and inorganic polymers), and the like.

The Conjugates

The cells used in the methods of assaying of the present invention may comprise a conjugate of an arrestin protein and a detectable molecule. In the cells and methods of the present invention, the cells may also comprise a conjugate of a modified GPCR of the present invention and a detectable molecule.

All forms of arrestin, naturally occurring and engineered variants, including but not limited to, visual arrestin, βarrestin 1 and βarrestin 2, may be used in the present invention. The modified GPCRs of the present invention may interact to a detectable level with all forms of arrestin.

Detectable molecules that may be used to conjugate with the arrestin include, but are not limited to, molecules that are detectable by spectroscopic, photochemical, biochemical, immunochemical, electrical, radioactive, and optical means, including but not limited to bioluminescence, phosphorescence, and fluorescence. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s). These detectable molecules should be a biologically compatible molecule and should not compromise the ability of the arrestin to interact with the GPCR system and the interaction of the arrestin with the GPCR system must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the arrestin protein by methods as described in Barak et al. (U.S. Pat. Nos. 5,891, 646 and 6,110,693). The detectable molecule may be conjugated to the arrestin at the front-end, at the back-end, or in the middle.

The modified GPCRs or biologically active fragments thereof may also be conjugated with a detectable molecule. Preferably, the carboxyl-terminus of the modified GPCR is conjugated with a detectable molecule. A carboxyl-terminal tail conjugated or attached to a detectable molecule can be used in a carboxyl-terminal tail exchange to provide the modified GPCRs of the present invention.

If the modified GPCR is conjugated with a detectable molecule, proximity of the modified GPCR with the arrestin may be readily detected. In addition, if the modified GPCR is conjugated with a detectable molecule, compartmentalization of the modified GPCR with the arrestin may be readily confirmed. The detectable molecule used to conjugate with the modified GPCRs may include those as described above, including, for example, optically detectable molecules, such that they may be excited chemically, mechanically, electrically, or radioactively to emit fluorescence, phosphorescence, or bioluminescence. Preferred optically detectable molecules may be detected by immunofluorescence, luminescence, fluorescence, and phosphorescence.

For example, the modified GPCRs may be antibody labeled with an antibody conjugated to an immunofluorescence molecule or the modified GPCRs may be conjugated with a luminescent donor. In particular, the modified GPCRs may be conjugated with, for example, luciferase, for example, *Renilla* luciferase, or a rhodamine-conjugated antibody, for example, rhodamine-conjugated anti-HA mouse monoclonal antibody. Preferably, the carboxyl-terminal tail of the modified GPCR may be conjugated with a luminescent donor, for example, luciferase. The modified GPCR, preferably the carboxyl-terminal tail, also may a be conjugated with GFP as described in L. S. Barak et al. "Internal Trafficking and Surface Mobility of a Functionally Intact $\beta_2$-Adrenergic Receptor-Green Fluorescent Protein Conjugate", *Mol. Pharm.* (1997) 51, 177–184.

Cell Types and Substrates

The cells of the present invention may express at least one modified GPCR of the present invention. The cells may further comprise a conjugate of an arrestin protein and a detectable molecule. Useful cells include eukaryotic and prokaryotic cells, including, but not limited to, bacterial cells, yeast cells, fungal cells, insect cells, nematode cells, plant cells, and animal cells. Suitable animal cells include, but are not limited to, HEK-293 cells, HeLa cells, COS cells, and various primary mammalian cells. An animal model expressing a conjugate of an arrestin and a detectable molecule throughout its tissues or within a particular organ or tissue type, may also be used.

The cells of the present invention may express one modified protein that results in agonist-independent localization of GPCRs to endocytic vesicles or endosomes.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

Expression of Modified GPCRs

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Such vectors may be plasmids, linear DNA, and the like, and may be introduced into hosts via standard methods such as transformation, transfection, gene guns, and the like. Suitable vectors include derivatives of SV40 and known bacterial plasmids (e.g., *E. coli* plasmids col EI, pCR1, pBR322, pMB9 and their derivatives), plasmids such as RP4; phage DNA (e.g., the numerous derivatives of phage λ, e.g., NM989), and other phage DNA (e.g., M13 and filamentous single stranded phage DNA); yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (i.e., sequences that control the expression of a DNA sequence operatively linked to it) may be used in these vectors to express the DNA sequences of this invention. Such useful expression control sequences include, for example, the early or late promoters of SV40, CMV, vaccinia virus, polyoma virus or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts (e.g. *Saccharomyces*), plant cells, nematode cells, and animal cells, such as HEK-293, CHO, RI.I, B-W and L-M cells, African Green Monkey kidney cells (e.g., COS-1, COS-7, BSC1, BSC40, and BMT10 cells), insect cells (e.g., Sf9 cells), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered, because the vector must be operable therein. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that modified GPCR analogs may be prepared from nucleotide sequences of the protein complex/subunit derived within the scope of the present invention. Analogs, such as fragments of modified GPCRs, may be produced, for example, by pepsin digestion of modified GPCR material. Other analogs, such as muteins, can be produced by standard site-directed mutagenesis of modified GPCR coding sequences. Analogs which function like modified GPCRs, such as small molecules, whether functioning as promoters or inhibitors, may be identified by known in vivo and/or in vitro assays.

As mentioned above, a DNA sequence encoding a modified GPCR can be prepared synthetically rather than cloned. The DNA sequence can be designed with the appropriate codons for the modified GPCR amino acid sequence. In general, one will select preferred codons for the intended host if the sequence will be used for expression. The complete sequence is assembled from overlapping oligonucleotides prepared by standard methods and assembled into a complete coding sequence. See, e.g., Edge et al., *Nature*, 292:756–762 (1981); Nambiar et al., *Science*, 223: 1299–1301 (1984); Jay et al., *J. Biol. Chem.*, 259:6311–6317 (1984).

Synthetic DNA sequences allow convenient construction of genes which will express GPCR analogs or "muteins". Alternatively, DNA encoding muteins can be made by site-directed mutagenesis of native or modified GPCR genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids. Generally, unnatural amino acids are commercially available from vendors such as Aldrich and Bachem. Examples of unnatural amino acids include, homoserine, homocysteine, N-α-methylarginine, norleucine, N-methylisoleucine, phenylglycine, hydroxyproline, pyroglutamine, ornithine, 2-aminoisobutyric acid, 2-aminobutyric acid, β-cyclohexylalanine, 3-(1-naphthyl)alanine, 3-(2-naphthyl) alanine, citrulline, pipecolinic acid, piperazic acid, 4-chlorophenylalanine, 4-fluorophenylalanine and sarcosine.

Methods of Detection

Methods of detecting the intracellular location of the conjugate of arrestin and a detectable molecule, the intracellular location of a GPCR fused to a detectable molecule, or interaction of the arrestin, which is conjugated to a detectable molecule, with a GPCR or any other cell structure, including for example, the concentration of arrestin at a cell membrane, colocalization of arrestin with GPCR in endocytic vesicles or endosomes, and concentration of arrestin in clathrin-coated pits, and the like, will vary dependent upon the detectable molecule(s) used. One skilled in the art readily will be able to devise detection methods suitable for the detectable molecule(s) used. For optically detectable molecules, any optical method may be used where a change in the fluorescence, bioluminescence, or phosphorescence may be measured due to a redistribution or reorientation of emitted light. Such methods include, for example, polarization microscopy, BRET, FRET, evanescent wave excitation microscopy, and standard or confocal microscopy.

In a preferred embodiment, arrestin may be conjugated to GFP and the arrestin-GFP conjugate may be detected by confocal microscopy. In another preferred embodiment, arrestin may conjugated to a GFP and the modified GPCR may be conjugated to an immunofluorescent molecule; the conjugates may be detected by confocal microscopy. In an additional preferred embodiment, arrestin may be conjugated to a GFP, and the carboxy-terminus of the modified GPCR may be conjugated to a luciferase. These conjugates can be detected by bioluminescence resonance emission technology. In a further preferred embodiment, arrestin may be conjugated to a luciferase, and the modified GPCR may be conjugated to a GFP. The luciferase/GFP conjugates may be detected by bioluminescence resonance emission technology. The methods of the present invention are directed to detecting GPCR activity. The methods of the present invention allow enhanced monitoring of the GPCR pathway in real time.

Diagnostic and Therapeutic Treatments

The possibilities of both diagnostic and therapeutic treatments that are raised by the existence of the GPCR derive from the fact that the factors appear to participate in direct and causal protein-protein interaction between a ligand thereto, and those factors that thereafter initiate an intracellular signal. As discussed earlier and elaborated further on herein, the present invention contemplates pharmaceutical intervention in the cascade of reactions in which the native or modified GPCRs are implicated, to modulate the activity initiated by the GPCR.

Thus, in instances where it is desired to reduce or inhibit the activity resulting from a particular stimulus or factor, an appropriate inhibitor of the GPCR could be introduced to block the interaction of the GPCR with a ligand. Correspondingly, instances in which insufficient activation of a G protein or second messenger is taking place could be remedied by introduction of additional quantities of the GPCR or its chemical or pharmaceutical cognates, analogs, fragments and the like.

The present invention further contemplates therapeutic compositions useful in practicing the therapeutic methods of this invention. A subject therapeutic composition includes, in admixture, a pharmaceutically acceptable excipient (carrier) and one or more of an agonist, antagonist, or DAC of the GPCR, as described herein as an active ingredient. In a preferred embodiment, the composition comprises a drug capable of modulating the specific binding of the GPCR with a ligand on a target cell.

Antibodies

Also, antibodies including both polyclonal and monoclonal antibodies, and drugs that modulate the production or activity of the modified GPCRs and/or their biologically active fragments or subunits may possess certain diagnostic applications and may for example, be utilized for the purpose of detecting and/or measuring conditions such as viral infection or the like. For example, the modified GPCR or fragments or subunits thereof may be used to produce both polyclonal and monoclonal antibodies, to the modified GPCR or fragments or subunits thereof, in a variety of cellular media, by known techniques such as the hybridoma technique utilizing, for example, fused mouse spleen lymphocytes and myeloma cells. Likewise, small molecules that mimic or antagonize the activity(ies) of the modified GPCRs of the invention may be discovered or synthesized, and may be used in diagnostic and/or therapeutic protocols.

The present invention likewise extends to the development of antibodies against the modified GPCR(s), including naturally raised and recombinantly prepared antibodies. For example, the antibodies could be used to screen expression libraries to obtain the gene or genes that encode the modified GPCR(s). Such antibodies could include both polyclonal and monoclonal antibodies prepared by known genetic techniques, as well as bispecific (chimeric) antibodies, and antibodies including other functionalities suiting them for additional diagnostic use conjunctive with their capability of modulating modified GPCR activity. Preferably, the anti-modified-GPCR antibody used in the diagnostic methods of this invention is an affinity purified polyclonal antibody. More preferably, the antibody is a monoclonal antibody (mAb). In addition, it is preferable for the anti-modified-GPCR antibody fragments used herein be in the form of Fab, Fab', F(ab')$_2$, F(v), or scFv.

The general methodology for making monoclonal antibodies by hybridomas is well known. Methods for producing monoclonal anti-GPCR antibodies are also well-known in the art. See Niman et al., *Proc. Natl. Acad. Sci. USA*, 80:4949–4953 (1983). Typically, the GPCR or a peptide analog is used either alone or conjugated to an immunogenic carrier, as the immunogen in the before described procedure for producing anti-GPCR monoclonal antibodies. The culture is maintained under conditions and for a time period sufficient for the hybridoma to secrete the antibodies into the medium. The hybridomas are screened for the ability to produce an antibody that immunoreacts with the GPCR or peptide analog. The antibody-containing medium is then collected. The antibody can then be further isolated by well-known techniques. Immortal, antibody-producing cell lines can also be created by techniques other than fusion, such as direct transformation of B lymphocytes with oncogenic DNA, or transfection with Epstein-Barr virus. See, e.g., *Using Antibodies: A Laboratory Manual*, Harlow, Ed and Lane, David (Cold Spring Harbor Press, 1999).

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. A preferred inbred mouse strain is the Balb/c.

Methods for producing polyclonal anti-polypeptide antibodies are well-known in the art. See U.S. Pat. No. 4,493,795 to Nestor et al. A monoclonal antibody, and immunologically active fragments thereof, can be prepared using the hybridoma technology described in *Using Antibodies: A Laboratory Manual*, Harlow, Ed and Lane, David (Cold Spring Harbor Press, 1999), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a GPCR. Splenocytes are typically fused with myeloma cells using polyethylene glycol (PEG) 6000 MW. Fused hybrids are selected by their sensitivity to HAT (hypoxanthine, aminopterin, thymidine) supplemented media. Hybridomas producing a monoclonal antibody useful in practicing this invention are identified by their ability to immunoreact with the present GPCR and their ability to inhibit specified GPCR activity in target cells.

In particular, antibodies against specifically phosphorylated factors can be selected and are included within the scope of the present invention for their particular ability in following activated protein. Thus, activity of the modified GPCR or of the specific polypeptides believed to be causally connected thereto may therefore be followed directly by the assay techniques discussed herein, through the use of an appropriately labeled quantity of the modified GPCR or antibodies or analogs thereof.

Panels of monoclonal antibodies produced against modified GPCR peptides can be screened for various properties; i.e., isotype, epitope, affinity, and the like. Of particular interest are monoclonal antibodies that neutralize the activity of the modified GPCR or its subunits. Such monoclonals can be readily identified in GPCR assays. High affinity antibodies are also useful when immunoaffinity purification of native or recombinant modified GPCRs is possible.

Thus, the modified GPCR(s), their analogs and/or analogs, and any antagonists or antibodies that may be raised thereto, are capable of use in connection with various diagnostic techniques, including immunoassays, such as a radioimmunoassay, using for example, an antibody to the GPCR(s) that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against specifically phosphorylated factors may be selected and appropriately employed in the exemplary assay protocol, for the purpose of following activated protein as described above.

In the instance where a radioactive label, such as, but not limited to, the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques discussed herein and as known in the art.

As suggested earlier, the diagnostic method of the present invention comprises examining a cellular sample or medium by means of an assay including an effective amount of an antagonist to a modified GPCR/protein, such as an anti-modified-GPCR antibody, preferably an affinity-purified polyclonal antibody, and more preferably a mAb. In addition, it is preferable for the anti-modified-GPCR antibody fragments used herein to be in the form of Fab, Fab', F(ab')$_2$, F(v), or scFv. As previously discussed, patients capable of benefitting from this method include those suffering from cancer, a pre-cancerous lesion, a viral infection or other like pathological condition or disease. Methods for isolating the modified GPCR, inducing anti-modified-GPCR antibodies, and determining and optimizing the ability of anti-modified-GPCR antibodies to assist in the examination of the target cells are all well-known in the art.

The present invention includes an assay system which may be prepared in the form of a test kit for the quantitative analysis of the extent of the presence of the modified GPCRs, or to identify drugs or other agents that may mimic or block their activity. The system or test kit may comprise a labeled component prepared by one of the radioactive and/or enzymatic techniques discussed herein, coupling a label to the modified GPCR(s), their agonists and/or antagonists, and one or more additional immunochemical reagents, at least one of which is a free or immobilized ligand, capable either of binding with the labeled component, its binding partner, one of the components to be determined or their binding partner(s).

Antisense Compositions and Use Thereof

In another embodiment, antisense compositions and methods are provided for modulating the expression of genes identified by the above described methods. Preferable antisense compositions are those which target nucleic acids identified using a systematic in silico discovery method disclosed herein or known in the art. Preferred antisense compositions can target, for example, SEQ ID NO: 7–SEQ ID NO: 12. (FIG. 17)

It is preferred to target specific nucleic acids for antisense. "Targeting" an antisense composition to a particular nucleic acid would preferably be to a nucleic acid which encodes a protein, wherein the nucleic acid is one identified by a systematic in silico process disclosed herein. The gene can be from a pathogenic organism. The targeting includes determination of a site or sites within the target gene for the antisense reaction (e.g., joinder of the sense and antisense strands to thereby modulate function of the gene or gene transcript). Preferred antisense compositions are those that recognize and bind with a site encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes).

It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a protein which was identified by a systematic in silico method disclosed herein or one of the sequences disclosed herein.

A translation termination codon (or "stop codon") of a gene transcript may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Preferred antisense compositions would recognize and bind to areas containing a termination codon and/or an initiation codon of any target gene or the mRNA transcript it encodes.

The open reading frame (ORF) or "coding region," which is known in the art to refer to the region between the translation initiation codon and the translation termination codon, is also a region which may have preferred targets of the antisense compositions. Other target regions include the 5' untranslated region (5'-UTR) and the 3' untranslated region (3'-UTR). The 5'-UTR is known in the art to refer to the portion of an mRNA in the 5' direction from the translation initiation codon, and thus including nucleotides between the 5' cap site and the translation initiation codon of an mRNA or corresponding nucleotides on the gene. The 3' untranslated region (3'-UTR) is known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'→5' triphosphate linkage. The 5' cap region of an mRNA is considered to include the 5' cap structure itself, and the first 50 nucleotides adjacent to the cap. The 5' cap region may also be a preferred target region for an antisense composition.

In eukaryotic organisms, the genes are composed of introns and exons, with the exons containing the material which will encode the protein product of the gene. The intronic material, although transcribed from the gene to produce the mRNA, will be excised from the mRNA transcript prior to its translation into a protein. The exons are spliced together to form a continuous mRNA sequence. The mRNA splice sites, i.e., intron-exon junctions, may also be preferred target regions of antisense compositions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compositions targeted, for example, to DNA or pre-mRNA.

Once one or more target sites are identified in the genes identified using a systematic discovery process, oligonucleotides are chosen which are sufficiently complementary to the target, i.e., hybridize sufficiently well and with sufficient specificity, to result produce the desired biological outcome (e.g., inhibition and/or prevention of the GPCR-associated disease or condition, modulation of the activity of the modulated GPCR, modulation of the activity of the arrestin).

In the context of this invention, "hybridization" means hydrogen bonding, which may be Watson-Crick, Hoogsteen or reversed Hoogsteen hydrogen bonding, between complementary nucleoside or nucleotide bases. For example, adenine (A) and thymine (T) are complementary nucleobases which pair through the formation of hydrogen bonds. "Complementary," as used herein, refers to the capacity for precise pairing between typically two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. It is understood in the art that the sequence of an antisense composition need not be 100% complementary to that of its target nucleic acid to be specifically hybridizable. Alternatively, oligonucleotides which form triple helices with the gene can be supplied. An antisense composition typically is specifically hybridizable when binding of the composition to the target DNA or RNA molecule interferes with the normal function of the target DNA or RNA to cause a loss of utility. The loss of utility occurs when there is a sufficient degree of complementarity to avoid non-specific binding of the antisense composition to non-target sequences under conditions in which specific binding is desired. Preferred conditions for specific binding are physiological conditions in the case of in vivo assays or therapeutic treatment, and in the case of in vitro assays, under conditions in which the assays are performed.

Preferred antisense compositions contemplated would be for use as research reagents and diagnostics. For example, antisense oligonucleotides, which are able to inhibit gene expression, are often used by those of ordinary skill to elucidate the function of particular genes. Antisense compositions are also used, e.g., to distinguish between functions of various members of a biological pathway. Antisense modulation has, therefore, been harnessed for research use.

Oligonucleotides have been employed as therapeutic moieties in the treatment of disease states in animals and man. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, e.g., enhanced cellular uptake, enhanced affinity for nucleic acid target and increased stability in the presence of nucleases.

While antisense oligonucleotides are a preferred form of antisense composition, the present invention comprehends other oligomeric antisense compositions, including but not limited to oligonucleotide mimetics such as are described below. The antisense compositions in accordance with this invention preferably comprise from about 8 to about 30 nucleobases (i.e., from about 8 to about 30 linked nucleosides, and all lengths in between). The antisense compositions can be longer than 30 (e.g., 35, 40, 45, 50, 55, 60, 65, 70, 75, 80, 85, 90, 95, 100 or more as well as ranges in between). However, more preferred antisense compositions are comprise from about 12 to about 25 nucleobases and all lengths in between.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric composition. In turn, the respective ends of this linear polymeric structure can be further joined to form a circular structure. However, open linear structures are generally preferred for use as antisense compositions. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compositions useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones for use in antisense compositions include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'→5' linkages, 2'→5' linked analogs of these, and those having inverted polarity wherein the adjacent pairs of nucleoside units are linked 3'→5' to 5'→3' or 2'→5' to 5'→2'. Various salts, mixed salts and free acid forms are also included. For additional methods for preparing such phosphorus containing linkages, see for example, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones, which do not include a phosphorus atom, may have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. For methods of preparing modified oligonucleotide backbones which lack phosphorous atoms, see, e.g., U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other preferred oligonucleotide mimetics include replacement of both the sugar and the internucleoside linkage, i.e., the backbone, of the nucleotide units are replaced with novel groups. The base units are maintained for hybridization with an appropriate nucleic acid target composition. One such oligomeric composition, an oligonucleotide mimetic that has been shown to have excellent hybridization properties, is referred to as a peptide nucleic acid (PNA). In PNA compositions, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. For discussion of such methods, see for example, U.S. Pat. Nos. 5,539,082; 5,714,331; and 5,719,262 and Nielsen et al., *Science*, 1991, 254: 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) and amide backbones such as those described in U.S. Pat. No. 5,602,240. Also preferred are oligonucleotides having morpholino backbone structures, such as those described in U.S. Pat. No. 5,034,506.

Modified oligonucleotides used as antisense compositions as contemplated herein may also contain one or more substituted sugar moieties. Preferred oligonucleotides comprise one of the following at the 2' position: —OH; F—; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides may comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$—$CH_2$—O$CH_3$, also known as 2'-O-(2-methoxyethyl) or 2'-MOE) (Martin et al., *Helv. Chim. Acta*, 1995, 78: 486–504), i.e., an alkoxyalkoxy group. Another preferred modification includes 2'-dimethylaminooxyethoxy(i.e., a O($CH_2$)$_2$ ON($CH_3$)$_2$ group, also known as 2'-DMAOE) and 2'-dimethylaminoethoxyethoxy (also known in the art as 2'-O-dimethylaminoethoxyethyl or 2'-DMAEOE).

Other preferred modifications to the antisense compositions contemplated include 2'-methoxy (2'-O—$CH_3$), 2'-aminopropoxy (2'-O$CH_2$$CH_2$$CH_2$$NH_2$) and 2'-fluoro (2'-F). Similar modifications may also be made at other positions on the oligonucleotide, particularly at the 3' position of the sugar on the 3' terminal nucleotide or in 2'-5' linked oligonucleotides and the 5' position of 5' terminal nucleotide. Oligonucleotides may also have sugar mimetics, such as cyclobutyl moieties in place of the pentofuranosyl sugar. For methods of preparing such modified sugar structures, see for example, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). The invention also contemplates the use of modified nucleobases in the antisense compositions. Such modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8substituted adenines and guanines, 5-halo (e.g., particularly 5-bromo, 5-trifluoromethyl) and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional nucleobases would be known to the skilled artisan. See, for example, U.S. Pat. No. 3,687,808; THE CONCISE ENCYCLOPEDIA OF POLYMER SCIENCE AND ENGINEERING, 858–859 (Kroschwitz, J. I., ed. John Wiley & Sons, 1990); Englisch et al., ANGEWANDTE CHEMIE, v. 30, p. 613 (International Edition, 1991); and Sanghvi, Y. S., Chapter 15, ANTISENSE RESEARCH AND APPLICATIONS, 289–302 (Crooke et al., CRC Press, 1993). Certain of these nucleobases are particularly useful for increasing the binding affinity of the oligomeric compositions of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., et al., 1993) and are presently preferred base substitutions, even more particularly when combined with 2'-O-methoxyethyl sugar modifications.

Another oligonucleotide modification contemplated for use in the antisense compositions involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86: 6553–6), cholic acid (Manoharan et al., *Bioorg. Med. Chem. Lett.*, 1994, 4: 1053–60), a thioether, e.g., hexyl-S-tritylthiol (Manoharan et al., *Ann. N.Y. Acad. Sci.*, 1992, 660: 306–9; and Manoharan et al., *Bioorg. Med. Chem. Lett.*, 1993, 3: 2765–70), a thiocholesterol (Oberhauser et al., *Nucl. Acids Res.*, 1992, 20: 533–8), an aliphatic chain, e.g., dodecandiol or undecyl residues (Saison-Behmoaras et al., *EMBO J.*, 1991, 10: 1111–8; Kabanov et al., *FEBS Lett.*, 1990, 259: 327–30; and Svinarchuk et al., *Biochimie*, 1993, 75: 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36: 3651–4; and Shea et al., *Nucl. Acids Res.*, 1990, 18: 3777–83), a polyamine or a polyethylene glycol chain (Manoharan et al., *Nucleosides & Nucleotides*, 1995, 14: 969–73), or adamantane acetic acid (Manoharan et al., *Tetrahedron Lett.*, 1995, 36: 3651–4), a palmitoyl moiety (Mishra et al., *Biochim. Biophys. Acta*, 1995, 1264: 229–237), or an octadecylamine or hexylamino-carbonyl-oxycholesterol moiety (Crooke et al., *J. Pharmacol. Exp. Ther.*, 1996, 277: 923–937).

Methods for preparing such oligonucleotide conjugates would be known in the art and include but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

One or more of the positions in a given compound can be modified. It is not necessary for all positions in a given compound to be uniformly modified, and in fact more than one of the aforementioned modifications may be incorporated in a single compound or even at a single nucleoside within an oligonucleotide.

The present invention also includes antisense compositions which are chimeric compositions. "Chimeric" antisense compositions or "chimeras" in the context of antisense compositions, are compounds which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have are also known as hybrids or gapmers. Methods of preparing such hybrids include but are not limited to the teachings of U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

The antisense compounds contemplated herein may be conveniently and routinely made through the well-known technique of solid phase synthesis. The oligonucleotides can be prepared for example using the equipment and techniques of Applied Biosystems. Any other means for such synthesis known in the art may additionally or alternatively be employed.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Methods and preparations for such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The contemplated antisense compounds and compositions disclosed herein also include any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds of the invention, pharmaceutically acceptable salts of such prodrugs, and other bioequivalents.

Pharmaceutical Compositions

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A GPCR agonist, antagonist, or DAC obtained by the methods disclosed herein can be formulated into the therapeutic composition as neutralized pharmaceutically acceptable salt forms. Pharmaceutically acceptable salts include the acid addition salts (formed with the free amino groups of the polypeptide or antibody) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent (i.e., carrier, or vehicle).

The data obtained from the cell culture assays and animal studies can be used in formulating a range of dosage for use in humans. The dosage of such compositions lies preferably within a range of circulating concentrations that include the ED50 with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range which includes the IC50 (i.e., the concentration of the test composition which achieves a half-maximal inhibition of symptoms) as determined in cell culture. Such information can be used to more accurately determine useful doses in humans. Levels in plasma may be measured, for example, by high performance liquid chromatography.

The compositions are administered in a manner compatible with the dosage formulation, and in a therapeutically effective amount. The quantity to be administered depends on the subject to be treated, capacity of the subject's immune system to utilize the active ingredient, and degree of modulation of GPCR activity desired. Precise amounts of active ingredient required to be administered depend on the judgment of the practitioner and are peculiar to each individual. However, suitable dosages may range from about 0.001 to 30, preferably about 0.01 to about 25, and more preferably about 0.1 to 20 milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The skilled artisan will appreciate that certain factors may influence the dosage required to effectively treat a subject, including but not limited to, the severity of the disease or condition, disorder, or disease, previous treatments, the general health and/or age of the subject, and other diseases present. Moreover, treatment of a subject with a therapeutically effective amount of the composition(s) can include a single treatment or, preferably, can include a series of treatments. In a preferred example, a subject is treated with the composition in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of the composition used for treatment may increase or decrease over the course of a particular treatment. Changes in dosage may result and become apparent from the results of diagnostic assays as described herein.

The therapeutic compositions may further include an effective amount of the GPCR agonist, antagonist, or DAC and one or more of the following active ingredients: an antibiotic, a steroid, and the like.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention can be prepared as SATE ((S-acetyl-2-thioethyl) phosphate) derivatives according to the methods disclosed for example in WO 93/24510 and in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. The compounds for modulating any of the disclosed genes, gene transcripts or proteins encoded thereby include antisense compounds as well as other modulatory compounds.

Pharmaceutically acceptable base addition salts for use with antisense as well as other modulatory compounds are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, e.g., Berge et al., "Pharmaceutical Salts," J. Pharma. Sci., 1977, 66: 1–19). The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are known in the art and include basic salts of a variety of inorganic and organic acids, such as, for example, with inorganic acids (e.g., hydrochloric acid, hydrobromic acid, sulfuric acid or phosphoric acid); with organic carboxylic, sulfonic, sulfo- or phospho-acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid.

Pharmaceutically acceptable salts of compounds may also be prepared with a pharmaceutically acceptable cation. Suitable pharmaceutically acceptable cations are well known in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds and other modulatory compounds described herein can be utilized in pharmaceutical compositions by adding an effective amount of an antisense compound or other modulatory compound to a suitable pharmaceutically acceptable diluent or carrier. Use of the compounds and methods of the invention may also be useful prophylactically.

The antisense compounds of the invention are useful for research and diagnostics, because these compounds hybridize to nucleic acids encoding a gene identified using the systematic discovery technique or a mRNA transcript thereof. Such hybridization allows the use of sandwich and other assays to easily be constructed to exploit this fact. Hybridization of the antisense oligonucleotides of the invention with a nucleic acid encoding a gene or gene transcript identified by a systematic discovery method can be detected by means known in the art. Such means may include, for example, conjugation of an enzyme to the oligonucleotide, radiolabelling of the oligonucleotide or any other suitable detection means. Kits using such detection means for detecting the level of a transcript of a gene in a sample may also be prepared.

The present invention also includes pharmaceutical antisense compositions and formulations which include the antisense compounds and other modulatory compounds and compositions of the invention. The pharmaceutical compositions of the present invention may be administered in a number of ways depending upon whether local or systemic treatment is desired and upon the area to be treated.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compositions may be combined with a carrier so that an effective dosage is delivered, based on the desired activity.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer, salts, flavoring, coloring and sweetening agents as appropriate.

Preparations for oral administration may be suitably formulated to give controlled release of the active composition.

The compositions may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For administration by inhalation, the compositions for use according to the present invention are conveniently delivered in the form of an aerosol spray, presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the composition and a suitable powder base such as lactose or starch.

The compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Pharmaceutical compositions (e.g., gene, gene transcript or protein product modulatory agents as described herein) of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature, these formulations vary in the components and the consistency of the final product. The preparation of such compositions and formulations is generally known to those skilled in the pharmaceutical and formulation arts and may be applied to the formulation of the compositions of the present invention.

The compositions of the present invention may be prepared and formulated as emulsions. Emulsions are typically heterogenous systems of one liquid dispersed in another in the form of droplets usually exceeding 0.1 m in diameter. See, e.g., Idson, in Pharmaceutical Dosage Forms v. 1, p. 199 (Lieberman, Rieger and Banker (Eds.), 1988, Marcel Dekker, Inc., New York); Rosoff, in Pharmaceutical Dosage Forms, v. 1, p. 245; Block in Pharmaceutical Dosage Forms, v. 2, p. 335; Higuchi et al., in Remington's Pharmaceutical Sciences 301 (Mack Publishing Co., Easton, Pa., 1985). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms v. 1, p. 199 (Lieberman, Rieger and Banker (Eds.), 1988, Marcel Dekker, Inc., New York).

Synthetic surfactants, also known as surface active agents, have found wide applicability in the formulation of emulsions and have been reviewed in the literature (Rieger, in Pharmaceutical Dosage Forms, v. 1, p. 285; Idson, in Pharmaceutical Dosage Forms, v. 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers, especially in combination with surfactants and in viscous preparations. These include polar inorganic solids, such as heavy metal hydroxides, non-swelling clays (e.g., bentonite, attapulgite, hectorite, kaolin, montmorillonite, colloidal aluminum silicate and colloidal magnesium aluminum silicate), pigments and nonpolar solids (e.g., carbon or glyceryl tristearate).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, v. 1 p. 385 (Lieberman, Rieger and Banker (Eds.), 1988, Marcel Dekker, Inc., New York)).

Hydrophilic colloids or hydrocolloids include naturally occurring gums and synthetic polymers, such as polysaccharides (e.g., acacia, agar, alginic acid, carrageenan, guar gum, karaya gum, and tragacanth), cellulose derivatives (e.g., carboxymethylcellulose and carboxypropylcellulose), and synthetic polymers (e.g., carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers (e.g., tocopherols, alkyl gallates, butylated hydroxyanisole, butylated hydroxytoluene) or reducing agents (e.g., ascorbic acid and sodium metabisulfite), and antioxidant synergists (e.g., citric acid, tartaric acid, and lecithin).

The application of emulsion formulations via dermatological, oral and parenteral routes and methods for their manufacture have been reviewed in the literature (Idson, in Pharmaceutical Dosage Forms, v. 1, p. 199). Emulsion formulations for oral delivery have been very widely used because of reasons of ease of formulation, efficacy from an absorption and bioavailability standpoint. (Rosoff, in Pharmaceutical Dosage Forms, v. 1, p. 245 (Lieberman, Rieger and Banker (Eds.), 1988, Marcel Dekker, Inc., New York); Idson, in Pharmaceutical Dosage Forms). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, v. 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in Controlled Release of Drugs: Polymers and Aggregate Systems, 185–215 (Rosoff, M., Ed., 1989, VCH Publishers, New York). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, 271 (Mack Publishing Co., Easton, Pa., 1985).

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with co-surfactants. The co-surfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of co-surfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono-, di-, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharm. Res., 1994, 11:1385–90; Ritschel, Meth. Find. Exp. Clin. Pharmacol., 1993, 13: 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., 1994; Ho et al., J. Pharm. Sci., 1996, 85: 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids and other active agents from the gastrointestinal tract, as well as improve the local cellular uptake of oligonucleotides and nucleic acids and other active agents within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Crit. Rev. Therap. Drug Carrier Systems, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, are useful because of their specificity and the duration of action. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo. Selection of the appropriate liposome depending on the agent to be encapsulated would be evident given what is known in the art.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: (a) liposomes obtained from natural phospholipids are biocompatible and biodegradable; (b) liposomes can incorporate a wide range of water and lipid soluble drugs; (c) liposomes can protect encapsulated drugs in their internal compartments from metabolism and degradation (Rosoff, in Pharmaceutical Dosage Forms). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Another embodiment also contemplates the use of liposomes for topical administration. Such advantages include reduced side-effects related to high systemic absorption of the administered drug, increased accumulation of the administered drug at the desired target, and the ability to administer a wide variety of drugs, both hydrophilic and hydrophobic, into the skin. Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Comm., 1987, 147:980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., J. Controlled Release, 1992, 19: 269–74).

Another contemplated liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

"Sterically stabilized" liposomes, which refers to liposomes comprising one or more specialized lipids that, when incorporated into liposomes, result in enhanced circulation lifetimes relative to liposomes lacking such specialized lipids are also contemplated. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Lett., 1987, 223: 42; Wu et al., Can. Res., 1993, 53: 3765).

Many liposomes comprising lipids derivatized with one or more hydrophilic polymers, and methods of preparation thereof, are known in the art. See, e.g., Sunamoto et al. (Bull. Chem. Soc. Jpn., 1980, 53: 2778) described liposomes comprising a nonionic detergent, 2C12 15G, that contains a PEG moiety. Illium et al. (FEBS Lett., 1984, 167: 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268: 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029: 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 Bl and WO 90/04384 to Fisher. Liposome compositions containing 1–20 mole percent of PE derivatized with PEG, and methods of use thereof, are described by, e.g., Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.). Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

Methods of encapsulating nucleic acids in liposomes is also known in the art. See, WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, p. 285 (Marcel Dekker, Inc., New York, N.Y., 1988, p. 285)).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, 285 (Marcel Dekker, Inc., New York, N.Y., 1988).

In one embodiment, the present invention employs various penetration enhancers to effect the efficient delivery of nucleic acids and other agents, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Another embodiment of the invention contemplates pharmaceutical compositions comprising surfactants. Surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Crit. Rev. Therap. Drug Carrier Systems, 1991, 92); and perfluorochemical emulsions, such as FC-43 (Takahashi et al., J. Pharm. Pharmacol., 1988, 40: 252).

Another embodiment contemplates the use of various fatty acids and their derivatives to act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1–10 alkyl esters thereof (e.g., methyl, isopropyl and t-butyl), and mono- and di-glycerides thereof (i.e., oleate, laurate, caprate, myristate, palmitate, stearate, linoleate, and the like) (Lee et al., 1991; Muranishi, Crit. Rev. Therap. Drug Carrier Systems, 1990, 7: 1–33; El Hariri et al., J. Pharm. Pharmacol., 1992, 44: 651–4).

The compositions comprising the active agents of the invention may further comprise bile salts. The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, N.Y., 1996, pp. 934–935). Various natural bile salts, and their synthetic derivatives, act as penetration enhancers. Thus, the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., 1991; Swinyard, Chapter 39 In: Remington's Pharmaceutical Sciences, 18th Ed., Gennaro, ed., Mack Publishing Co., Easton, Pa., 1990, pages 782–783; Muranishi, 1990; Yamamoto et al., J. Pharm. Exp. Ther., 1992, 263: 25; Yamashita et al., J. Pharm. Sci., 1990, 79: 579–83).

The invention further contemplates compositions comprising chelating agents. Chelating agents can be defined as compounds that remove metallic ions from solution by forming complexes therewith, with the result that absorption of oligonucleotides through the mucosa is enhanced. With regards to their use as penetration enhancers for use when the active agent is an antisense agent, chelating agents have the added advantage of also serving as DNase inhibitors, as most characterized DNA nucleases require a divalent metal ion for catalysis and are thus inhibited by chelating agents (Jarrett, J. Chromatogr., 1993, 618: 315–39). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., 1991; Muranishi, 1990; Buur et al., J. Control Rel., 1990, 14:43–51).

The invention also contemplates pharmaceutical compositions comprising active agents and non-chelating non-surfactants. Non-chelating non-surfactant penetration enhancing compounds can be defined as compounds that demonstrate insignificant activity as chelating agents or as surfactants, but that nonetheless enhance absorption of oligonucleotides through the alimentary mucosa (Muranishi, 1990). This class of penetration enhancers include, for example, unsaturated cyclic ureas, 1-alkyl- and 1-alkenylazacyclo-alkanone derivatives (Lee et al., 1991); and non-steroidal anti-inflammatory agents such as diclofenac sodium, indomethacin and phenylbutazone (Yamashita et al., J. Pharm. Pharmacol., 1987, 39: 621–6).

For pharmaceutical compositions comprising oligonucleotides, agents that enhance uptake of oligonucleotides at the cellular level may also be added to the pharmaceutical and other compositions of the present invention. For example, cationic lipids, such as lipofectin (Junichi et al., U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes (e.g., limonene and menthone).

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'-isothiocyano-stilbene-2,2'-disulfonic acid (Miyao et al., Antisense Res. Dev., 1995, 5: 115–121; Takakura et al., Antisense & Nucl. Acid Drug Dev., 1996, 6: 177–183).

The pharmaceutical compositions disclosed herein may also comprise a excipients. In contrast to carrier compounds described above, these excipients include a pharmaceutically acceptable solvent, suspending agent or any other pharmacologically inert vehicle for delivering one or more nucleic acids or other active agents to an animal. The excipient may be liquid or solid and is selected, with the planned manner of administration in mind, so as to provide for the desired bulk, consistency, etc., when combined with a nucleic acid or other active agent and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids and other contemplated active agents may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids or other contemplated active agents can be used.

The compositions of the present invention may additionally contain other adjunct components conventionally found in pharmaceutical compositions, at their art-established usage levels. Thus, for example, the compositions may contain additional, compatible, pharmaceutically-active materials such as, e.g., antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In another related embodiment, compositions of the invention may contain one or more antisense compound or other active agents. Two or more combined compounds may be used together or sequentially.

Test Kits

In a further embodiment of this invention, commercial test kits suitable for use by a medical specialist may be prepared to determine the presence or absence of predetermined modified GPCR activity or predetermined GPCR activity capability in suspected target cells. In accordance with the testing techniques discussed above, one class of such kits will contain at least the labeled GPCR or its binding partner, for instance an antibody specific thereto, and directions, of course, depending upon the assay method selected, e.g., "competitive," "sandwich," "DASP" and the like. The kits may also contain peripheral reagents such as buffers, stabilizers, components for detecting molecules in the kit, etc.

Accordingly, a test kit may be prepared for the demonstration of the presence or capability of cells for predetermined GPCR activity, comprising:

(a) a predetermined amount of at least one labeled immunochemically reactive component obtained by the direct or indirect attachment of a modified GPCR or a specific binding partner thereto, to a detectable label; and (b) other reagents.

More specifically, the diagnostic test kit may comprise:

(a) as a control, a known amount of a modified GPCR (or a modified GPCR binding partner, or in the alternative, bound to a suitable tag, or plural such end products, etc. (or their binding partners) one of each; and (b) if necessary, other reagents.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling a GPCR to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined.

In accordance with the above, an assay system for screening potential drugs effective to modulate the activity of the GPCR may be prepared. The modified GPCRs may be introduced into a test system, and the prospective drug may also be introduced into the resulting cell culture, and the culture thereafter examined to observe any changes in the GPCR activity (e.g., signaling, recycling, affinity for arrestin, and the like) in the cells.

Knock-out Mice and Animals

For use as disease models and to test compounds identified herein, modified GPCR transgenic and knock-out mice and animals may be produced and utilized. For use as disease models and to test compounds identified herein, transgenic and knock-out mice and animals comprising modified components of the desensitization pathway described herein may be produced and utilized.

An additional aspect of the present invention is a knock-out mouse, the cells of the mouse containing at least one inactive endogenous arrestin gene (including for example, visual arrestin-gene, βarrestin-1-gene, and βarrestin-2 gene). The mouse may be a complete knockout or homozygous for the inactive endogenous arrestin gene, or the mouse may be a partial knockout or heterozygous for the inactive endogenous arrestin gene.

The knockout mouse may be useful for verification that a compound is in fact an arrestin inhibitor. For example, the knockout mouse of the present invention may be used as a model for comparison with wild-type mice that have been treated with an arrestin inhibitor. This comparison may be used to verify that the compound administered to the wild-type mice is an arrestin inhibitor.

The knockout mouse may also be useful for verification that a compound is in fact an arrestin activator. For example, partial knockout mice that have been treated with an arrestin activator may be used as a model for comparison with wild-type mice and complete knockout mice. This comparison may be used to verify that the compound administered is an arrestin activator.

The production of arrestin knockout mice can be carried out in view of the disclosure provided herein and in light of techniques known to those skilled in the art, such as described in U.S. Ser. No. 09/469,554, filed Dec. 22, 1999, U.S. Pat. No. 5,767,337 to Roses et al.; U.S. Pat. No. 5,569,827 to Kessous-Elbaz et al.; and U.S. Pat. No. 5,569, 824 to Donehower et al. (the disclosures of which are hereby incorporated by reference in their entirety); and A. Harada et al., Nature 369, 488 (1994).

The cells of the knockout mouse of the present invention contain at least one inactive endogenous arrestin gene (including, for example, visual arrestin-gene, βarrestin-1-gene, and βarrestin-2 gene). The mouse may be a complete knockout or homozygous for the inactive endogenous arrestin gene, or the mouse may be a partial knockout or heterozygous for the inactive endogenous arrestin gene.

Preferred mice for carrying out the present invention include those which contain at least one inactive endogenous visual arrestin-gene, βarrestin-1-gene, and βarrestin-2 gene. Knockout mice containing at least one inactive endogenous visual arrestin-gene may be used to monitor activity in eyes. Knockout mice containing at least one inactive endogenous βarrestin-1-gene and/or βarrestin-2 gene may be used to monitor activity in a wide variety of other organs.

An example of mice for carrying out the present invention are as disclosed below.

Although the present invention has been described in detail with reference to examples above, it is understood that various modifications can be made without departing from the spirit of the invention, and would be readily known to the skilled artisan. Additionally, the invention is not to be construed to be limited by the following examples.

EXAMPLES

The invention will be further explained by the following illustrative examples which are intended to be non-limiting.

Materials—Arginine vasopressin was obtained from Sigma Chemicals (St. Louis, Mo.), and [$^3$H]-AVP from Amersham (Piscataway, N.J.). Norepinephrine (NE) was obtained from Research Biochemical International (Natick, Mass.), [$^3$H]prazosin was from NEN (Boston, Mass.), phentolamine and angiotensin II (AngII) were from Sigma.

L158,809 (2-ethyl-5,7-dimethyl-3-[[2'-(1H-tetrazol-5-yl)[1,1'-biphenyl]-4-yl]methyl]-3H-Imidazo[4,5-b]pyridine; CAS registry number 133240-46-7) was a generous gift from Dr. E. Escher (Université de Sherbrooke, PQ, Canada). The golden hamster wild type $\alpha_{1B}$-AR, and R143A was a gift obtained from Dr. S. Cotecchia (Université de Lausanne, Switzerland). HEK-293 and COS cells were from the American Type Culture Collection (Manassas, Va.) and cell culture reagents were from Life Technologies (Rockville, Md.) and Cellco (Kensington, Md.).

Cell Culture and Transfection—For V2R experiments: HEK-293 cells were grown in Eagle's minimal essential medium with Earle's salt (MEM) supplemented with 10% fetal bovine serum and a 1:100 dilution of penicillin/streptomycin (Sigma Chemicals, St. Louis, Mo.). Cells were transiently transfected with plasmid cDNA using a modified calcium phosphate co-precipitation method as described in Barak et al., 1997, Mol. Pharmacol., 51:177–84. For $\alpha_{1B}$-AR and $AT_{1A}R$ experiments: Cells were transiently transfected in 10 cm² dishes (Falcon) with 1 μg receptor or GRK plasmid cDNA in pCDNA3.1(−) using above modified calcium phosphate transfection coprecipitation method for inositol phosphate and binding assays. For confocal microscopy, cells were transiently transfected in collagen (Sigma) coated 35 mm² glass bottom confocal dishes (MatTek, Ashland, Mass.) with Lipofectamine®2000 and Opti-MEM media (Life Technologies) using a standard method (Ciccarone, V., et al., 1999, Focus 21.2, 54–55). Cells for confocal microscopy were transfected with 30 ng of βarrestin or receptor plasmid cDNA in pEGFP and 250 ng of dynamin (K44A), GRK, or receptor in pcDNA3.1/zeo.

Receptor Binding and Adenylyl Cyclase Production—For V2R experiments: HEK-293 cells transiently expressing receptor cDNA were plated into 12 well Falcon dishes. The cells were washed twice in cold MEM and a 250 μl solution of 2% BSA in 4° C. MEM containing various concentrations of [$^3$H]AVP was added to each well for 30 minutes. Non-specific binding was determined in the presence of a 100-fold excess of cold AVP. The cells were then washed three times with cold MEM/BSA and the bound [$^3$H]AVP was extracted with 250 μl of 0.5M NaOH in PBS, neutralized with HCl, and measured using a liquid scintillation counter. cAMP production in intact HEK-293 cells containing V2R variants was measured as described in Barak et al., Mol. Pharmacol., 51:177–84 (1997). For $\alpha_{1B}$-AR and $AT_{1A}R$ experiments: Transiently transfected HEK-293 cells in 10 cm² dishes were washed twice in cold binding buffer (MEM+2% bovine serum albumin [BSA]), incubated for 1 hour at room temperature in binding buffer with varying concentrations of [$^3$H]prazosin (0.25 nM–8 nM), and washed three times in cold binding buffer to remove unbound ligand. Cell bound [$^3$H]prazosin was measured using a scintillation counter. Nonspecific binding was determined in the presence of 1000-fold molar excess of phentolamine (10 μM). For binding assays done to measure the effect of the co-expression of dynamin(K44A) or the addition of phentolamine in FIG. 14, a fixed concentration of 8 nM [$^3$H]prazosin was used.

Inositol Phosphate Determination—Transiently transfected HEK-293 cells in 10 cm² dishes were plated onto 12-well plates (Falcon) coated with 25 mg/ml poly-D-lysine (Sigma) and incubated overnight in MEM+10% FBS (fetal bovine serum) at 37° C. To assay for inositol phosphate production, cells were incubated overnight at 37° C. in labeling media (1 μCi/0.5 ml/well of [$^3$H]inositol in MEM+5% fetal bovine serum). Cells were washed with MEM, 20 mM HEPES, pH 7.4, 20 mM LiCl for 5 minutes at 37° C. and then treated with agonist. Total inositol phosphate was extracted and separated as previously described in Cotecchia, S., et al., 1992, J. Biol. Chem. 267: 1633–1639.

Confocal Microscopy—HEK-293 cells were plated on the day following transfection onto collagen (Sigma Chemical, St. Louis, Mo.) treated 35 mm² glass-bottomed culture dishes. Confocal microscopy was performed with a Zeiss laser-scanning microscope (LSM-510). GFP images were collected using the 488 nm argon excitation and a 505 nm long pass filter. For $\alpha_{1B}$-AR and $AT_{1A}R$ experiments: HEK-293 cells were transiently transfected in 35 mm² confocal dishes. Cells were stimulated with 10 μM NE or 1 μM AngII and incubated at 37° C. for 30 minutes before viewing. Alternatively, cells were cultured overnight at 37° C. in 10 μM phentolamine or 1 μM L158,809. Confocal microscopy was performed at 100× magnification with a Zeiss laser-scanning microscope (LSM-510). GFP and FITC images were collected using 488-nm excitation and a 505-nm long-pass filter.

Antibody Labeling—Live transfected cells were plated in 35 mm² dishes with glass-bottomed wells. They were incubated at room temperature with a 1:100 dilution of rhodamine-tagged antiHA mouse monoclonal antibody (Boehringer, Indianapolis, Ind.) in a 2% BSA/MEM solution with 10 mM HEPES for 40 minutes, washed three times in MEM/HEPES, and examined by fluorescence and confocal microscopy with the Zeiss LSM-5 10.

Whole Cell Phosphorylation—Receptor phosphorylation was performed essentially as described in Barak et al., J.

Biol. Chem., 274:7565–7569 (1999). Equivalent amounts of receptor, as determined by [$^3$H]AVP binding on whole cells, and the amount of solubilized protein in each sample were subjected to SDS-polyacrylamide gel electrophoresis and processed for autoradiography.

Receptor Immunoprecipitation and Western Blotting—HEK-293 cells were stimulated with or without AVP for 10 minutes, washed with ice-cold PBS, scraped into precipitation buffer as described in Barak et al., J. Biol. Chem., 274:7565–7569 (1999), and solubilized for 1 hour at 4° C. After centrifugation, supernatants were collected and HA-tagged receptors were immunoprecipitated at 4° C. using the anti-HA 12CA5 mouse monoclonal antibody (Boehringer Mannheim, Indianapolis, Ind.). Recovered proteins were subjected to SDS-polyacrylamide gel electrophoresis and immunoblotted with the anti-HA rabbit polyclonal antibody (BAbCO, Richmond, Calif.).

Example 1

Construction of Plasmid DNA

The N-terminal HA-tagged human vasopressin type II receptor, the V2R(Ala6), and the V2R(T362) were expressed in pcDNA3.1/zeo (Oakley, R. H., Laporte, S. A., Holt, J. A., Barak, L. S. & Caron, M. G. (1999) J. Biol. Chem. 274, 32248–32257). Their R137H analogues were generated by the polymerase chain reaction and inserted into the expression vector pEGFPN3 (Clontech, Palo Alto, Calif.) with stop codons intact using SacI/SalI restriction sites (FIG. 17, SEQ ID NO: 7). The green fluorescent protein conjugates of the wild type human V2 and V2R(RI37H) receptors were generated by the polymerase chain reaction from the human V2R and human V2R(RI37H) cDNA and inserted in frame at XhoI/SalI and SacI/SalI restriction sites of pEGFP-N3. βarrestin 2-GFP (S65T) was constructed as described in Shi et al., Biochemistry, 37:4869–4874 (1998).

The N-terminus HA epitope-tagged constructs were generated by PCR using 5' primers containing the HA sequence (TACCCATACGACGTCCCAG-ACTACGCT) followed by the gene sequence and cloned into pcDNA3.1/zeo (Invitrogen) and pEGFP-N3 (CLONTECH) at the NheI/HindIII and NheI/SalI sites, respectively. Dynamin(K44A) and βarrestin-GFP were constructed as previously described (Zhang, et al., 1997, J. Biol. Chem. 272:27005–27014. and Barak, et al., 1997, J. Biol. Chem. 272:27497–27500).

$\alpha_{1B}$-AR R143H, R143E, and R143N were generated by PCR and inserted into the NheI/SacII and the XhoI/PstI sites of pcDNA3.1/zeo and pEGFP-N3, respectively (FIG. 17, SEQ ID NO: 8, SEQ ID NO: 10, SEQ ID NO: 11).

The rat AT$_{1A}$R R126H was generated by PCR and cloned into pcDNA3.1/zeo and pEGFP-N3 at the NheI/HindIII and NheI/SalI sites, respectively (FIG. 17, SEQ ID NO: 12).

Example 2

Expression and Signaling of the V2R and V2R(RI37H) in HEK-293 Cells

The V2R(RI37H) mutation occurs in a conserved GPCR region associated with G protein coupling rather than receptor-ligand interactions. To begin to assess the effect of the R137H mutation, cells expressing the V2R and V2R (RI37H) receptors were compared with respect to ligand binding, plasma membrane expression levels, and downstream signaling. The affinity of the V2R(R137H) mutant for the ligand AVP was compared to the affinity of wild-type V2R for the ligand AVP. The expression levels of V2R and V2R(RI37H) on the plasma membrane were compared, and cAMP accumulation was measured in cells expressing the V2R and V2R(R137H) receptors to compare signaling.

Figure 4B:
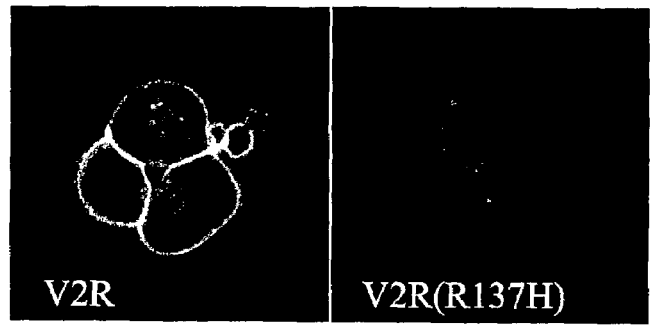
Figure 4C:
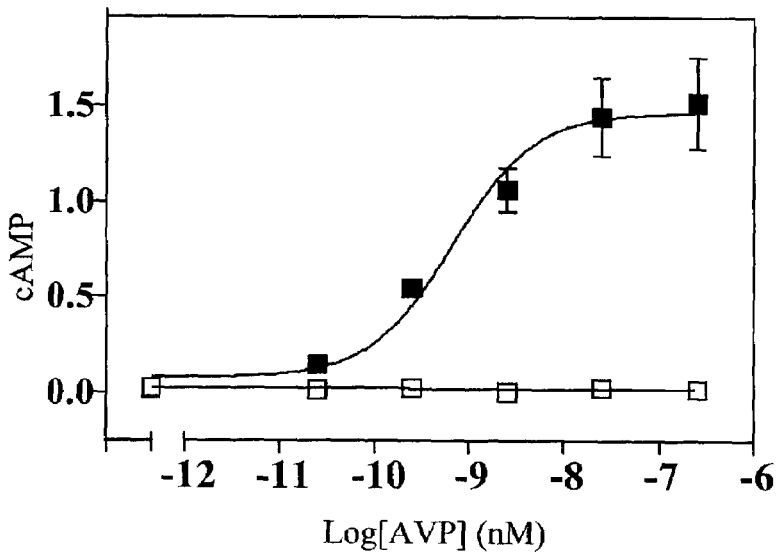

The HEK-293 whole cell binding data presented in FIG. 4A indicate that the wild type V2R and V2R(RI37H) have the same affinity for AVP. In contrast, the Scatchard Plot (inset A) suggests that plasma membrane V2R(R137H) expression is much lower. This finding is confirmed by comparing the amount of fluorescence originating from HA-tagged V2R (FIG. 4B, left panel) and V2R(R137H) (FIG. 4B right panel) at the surface of live, unpermeabilized HEK-293 cells labeled with rhodamine-conjugated anti-HA antibody. FIG. 4C shows the amount of whole cell, AVP stimulated (0 to 250 nM) cAMP production in HEK-293 cells transfected with wild type V2R or V2R(RI37H). Essentially no adenylyl cyclase activity above basal is observed in the V2R(RI37H) transfected cells. These data indicate that the V2R(RI37H) NDI may arise from an inability of the receptor to activate G protein.

Example 3

Distribution and Trafficking of the V2R and V2R(R137H) in Response to AVP

Many GPCRs express mutations that uncouple the receptors from G proteins without affecting receptor expression at the plasma membrane. Even though plasma membrane expression of the V2R(RI37H) is relatively small, its intracellular complement in the absence of agonist is relatively large, as described in reference Schoneberg et al., Hum. Mutat., 12:196–205 (1998). Thus, the R137H mutation may also affect the trafficking mechanisms that determine receptor localization, as described in Schoneberg et al., Embo. J., 15:1283–1291 (1996).

In order to study V2R and V2R(RI37H) trafficking in HEK-293 cells, a strategy using V2R- or V2R(RI37H) green fluorescent protein chimeras were used. FIG. 5 demonstrates that in the absence of agonist, V2R-GFP fluorescence originated predominantly from the plasma membrane (upper left panel). The addition of 100 nM AVP produces a loss of membrane fluorescence and a redistribution of V2R to endocytic vesicles (upper right panel) in a manner similar to wild type V2R. Vesicles can be observed in either the cytosol or in the perinuclear region, depending on the time after agonist addition or the position of the confocal slice through the cell. In contrast, the majority of V2R(RI37H)-GFP is cytosolic and vesicular (FIG. 5, lower left panel) in the absence of agonist, and exposure to 100 nM AVP for 30 minutes does not appreciably alter V2R(RI37H)GFP distribution.

Example 4

Figure 6:
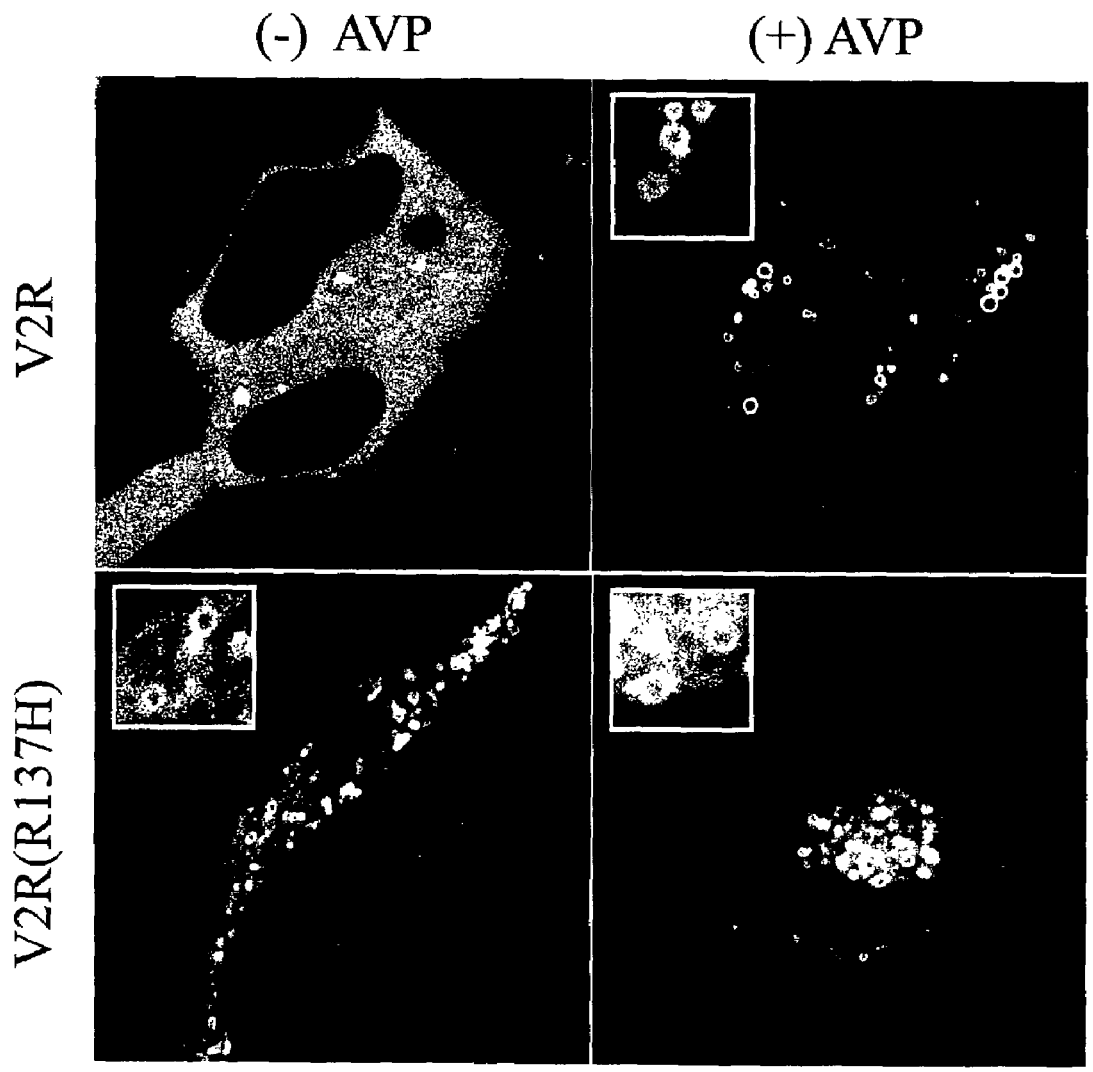
FIG. 6 illustrates the fluorescence images of the association between βarrestin2-GFP and V2R or V2R(R137H) in HEK-293 cells. Left shows the agonist-independent distribution of βarrestin2-GFP in living cells expressing the V2R (Upper) or V2R(R137H) (Lower). Without agonist treatment, βarrestin2-GFP is cytosolic in cells containing wild-type V2R (Left Upper), but in cells containing the V2R (R137H) (Left Lower), it is also in endocytic vesicles. Following 30 min. of exposure to 100 nM AVP (Right), βarrestin-GFP is localized on endocytic vesicles with both receptor subtypes.

Distribution and Trafficking of βarrestin in HEK-293 Cells Expressing the V2R or V2R(RI37H) in Response to AVP AVP-mediated endocytosis of the V2R in HEK-293 cells has been demonstrated to require βarrestins, as described in Barak et al., J. Biol. Chem., 274:7565–7569 (1999). The observed vesicular localization of the V2R(RI37H)-GFP in the absence or presence of AVP is characteristic of βarrestin-mediated endocytosis and suggests that the V2R(RI37H) may bind βarrestin sufficiently well without agonist to promote its own internalization. To examine the interaction of βarrestin with the V2R(RI37H) in live HEK-293 cells, either the V2R or V2R(RI37H) and a βarrestin 2-GFP fusion protein was transfected, as described in Lohse, et al., *Science*, 248:1547–1550 (1990) and Barak et al., *J. Biol. Chem* 274:7565–7569 (1999). When βarrestin2-GFP is expressed with the V2R in the absence of agonist, the fluorescence is cytosolic and homogeneous (FIG. 6, upper left panel). Addition of AVP results in the translocation of βarrestin to plasma membrane V2R, and the subsequent AP2-directed clustering of the βarrestin-receptor complex in clathrin-coated vesicles, and internalization of the βarrestin-receptor complex into endosomes. The appearance of βarrestin2-GFP in endosomes following AVP treatment is indicated by the vesicular distribution of GFP fluorescence shown in FIG. 6 (upper right panel and insert).

In contrast to the findings for the V2R, βarrestin2-GFP is distributed in endosomes in cells expressing the V2R (RI37H) independent of agonist (FIG. 6 lower left and right panels). The localization of βarrestin-GFP in endocytic vesicles (insets) suggests that the intracellular V2R(RI37H) population may arise from plasma membrane receptors through a βarrestin-directed process. This suggests that the inability of V2R(R137H) to activate G proteins may be due in part to a ligand independent desensitization rather than an inability to activate G proteins.

Example 5

Inhibition of Internalization of the V2R or V2R(R137H) βarrestin Complex in the Presence of Dominant Negative Dynamin The cytosolic protein dynamin is required for the separation of clathrin-coated vesicles from the plasma membrane, and overexpression of the dynamin(K44A) variant, which competitively inhibits clathrin-coated vesicle dissociation, has been used to assess clathrin mediated GPCR internalization, as described in Zhang et al., *J. Biol. Chem.*, 274:10999–11006 (1999). To determine if the spontaneous association of βarrestin with the receptor in the absence of agonist is sufficient to induce receptor internalization, the ability of dynamin(K44A) to redistribute the complement of cytosolic βarrestin2-GFP to the plasma membrane in cells expressing the V2R(RI37H) was assessed.

Figure 7A:
FIG. 7 illustrates the βarrestin2 association with and phosphorylation of V2R and V2R(R137H) in HEK-293 cells. (A) Dynamin(K44A) was expressed with βarrestin2-GFP and either V2R or V2R(R137H). Exposure of V2R to AVP (100 nM) (Left) resulted in appreciable βarrestin2-GFP translocation that remains visible at 30 min. as a punctate distribution at the cell membrane rather than as a vesicular distribution inside the cell. In the absence of agonist, the cells containing dynamin(K44A) and V2R(R137H) also show βarrestin2-GFP fluorescence distributed in punctate areas at the plasma membrane. A similar pattern was apparent even in the presence of agonist (Right). (B) Left panel shows receptors that were immunoprecipitated with a mouse anti-HA antibody and blotted with a rabbit anti-HA antibody. The faint 50-kDa band present in all six lanes is cross-reactive mouse Ig heavy chain. Right panel depicts receptors that were assayed for phosphorylation as described in Experimental Procedures. Equal amounts of receptor (40 fmol) were loaded into each lane. The arrows mark the positions of the receptor species migrating at approximately 70, 50, and 40 kDa as revealed by anti-HA antibody. Results are representative of three experiments.

In HEK-293 cells in the absence of agonist the expression of dynamin(K44A) with the V2R did not significantly change the homogeneous cytosolic distribution of βarrestin-GFP. In contrast, after 30 minutes of AVP treatment βarrestin-GFP remained at the plasma membrane in a punctate distribution and did not traffic into endocytic vesicles, compare FIG. 7A (Left panel) and FIG. 6. Thus, dynamin(K44A) expression inhibited the internalization of the V2R-βarrestin complex via clathrin-coated pits. In the absence of agonist the simultaneous expression of dynamin(K44A) and V2R (RI37H) produced a plasma membrane distribution of βarrestin 2-GFP similar to the βarrestin 2-GFP distribution observed for the V2R in the presence of agonist (FIG. 7A, Left panel). AVP addition did not appreciably change the plasma membrane distribution of βarrestin2-GFP (FIG. 7A, Right panel); however βarrestin2-GFP coated vesicles did become apparent in some cells. The ability of dynamin (K44A) to redistribute the complement of cytosolic βarrestin2-GFP to the plasma membrane in cells expressing the V2R(RI37H) suggests that the spontaneous association of βarrestin with the receptor in the absence of agonist, is sufficient to induce receptor internalization.

Example 6

Constitutive Phosphorylation of the V2R(R137H)

Figure 7B:
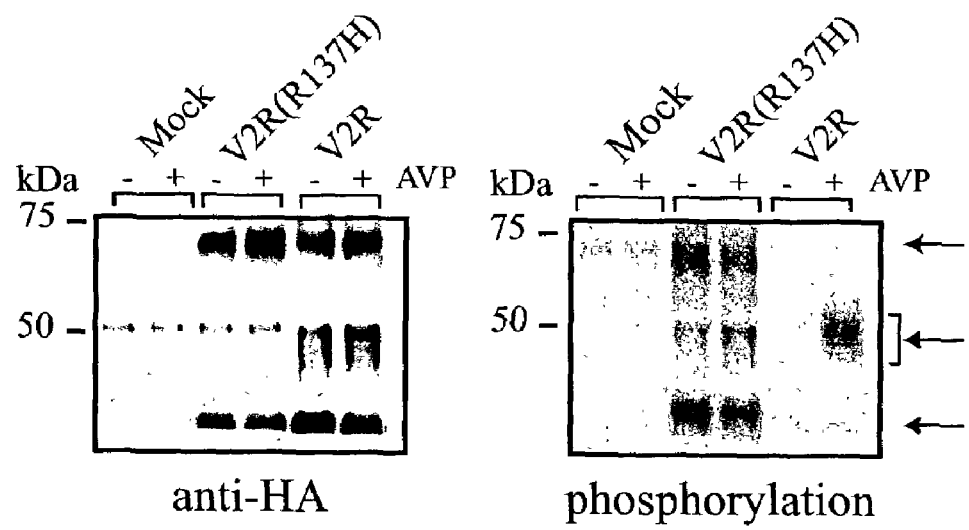

The affinity between many GPCRs and βarrestin is regulated by GRK phosphorylation. Therefore, the phosphorylation states of the V2R and V2R(RI37H) expressed in HEK-293 cells in the absence and presence of AVP was studied. Western blot analysis of immunoprecipitated V2R revealed three major species of this receptor migrating at approximately 70, 50, and 40 kDa (FIG. 7B, arrows, left panel). The amount of basal phosphorylation observed for each V2R species was minimal and only the 50 kDa form was phosphorylated in response to agonist (FIG. 7B, right panel). Western blot analysis of immunoprecipitated V2R (RI37H) revealed forms of this receptor migrating at approximately 70 and 40 kDa (FIG. 7B, left panel) that were sensitive to digestion by Endoglycosidase H and PNGase A (data not shown) that most probably represent immature glycosylated forms of the receptor (Sadeghi, H. & Birnbaumer, M. (1999) *Glycobiology* 9:731–737; Sadeghi, H. M., Innamorati, G. & Birnbaumer, M. (1997) *J. Recept. Signal Transduct. Res*. 17:433–445). Each of these forms of the V2R(RI37H) were constitutively phosphorylated (FIG. 7B, right panel). Although a 50 kDa species of the V2R (RI37H) was not detected on the Western blot, the more sensitive phosphorylation assay revealed a small amount of agonist mediated phosphorylation to this form of the receptor (FIG. 7B, middle arrow, right panel), which is most probably membrane associated. Moreover, the 50 kDa form of the V2R(RI37H) was also phosphorylated in the absence of agonist. Therefore, it appears that the abnormal phenotypic behavior of the V2R(RI37H) may primarily reflect the constitutive association of βarrestin with a phosphorylated receptor.

Example 7

Reversal of V2R(R137H) Constitutive Desensitizaton and βarrestin Affinity

An increased receptor affinity for arrestins in the absence of agonist could mask the ability of the V2R(RI37H) to couple normally to G-protein and stimulate cAMP. Since arrestins both desensitize GPCRs and promote their internalization, interventions that decrease arrestin affinity for the V2R(RI37H) may reestablish a more normal receptor response.

Alanine substitution and C-tail truncation mutants of the wild type V2R (the V2R(Ala6) and V2R(T362) respectively) demonstrated that a single cluster of three serines in the tail of the V2R GPCR can substantially decrease the receptor's ability to bind βarrestin, as described in Barak et al., *J. Biol. Chem*., 274:7565–7569 (1999). Analogous mutants were constructed for the V2R(R137H), V2R (RI37H, Ala6) and V2R(RI37H, T362). The mutants demonstrated a decreased βarrestin affinity that normalized the receptor localization at the plasma membrane and corrected its ability to stimulate adenylyl cyclase. FIG. 8A (upper panels) shows representative images of HA-tagged V2R, V2R(RI37H, Ala6), and V2R(RI37H, T362) on live, unpermeabilized HEK-293 cells labeled with rhodamine-anti HA antibody. Each receptor subtype is easily observable at the plasma membrane by rhodamine fluorescence in the absence of agonist. The result contrasts to findings demonstrating relatively little antibody-labeled V2R(RI37H) on the surface of unpermeabilized HEK-293 cells (FIG. 4). Addition of AVP to cells containing V2R, V2R(RI37H, Ala6) and V2R (RI37H, T362) results in the loss of plasma membrane fluorescence and the appearance of cytosolic fluorescence as a result of receptor endocytosis (FIG. 8A lower panels). The return of the plasma membrane population of V2R(RI37H) tail mutants towards wild type levels was confirmed by the binding of AVP (FIG. 8B).

Figure 9A:
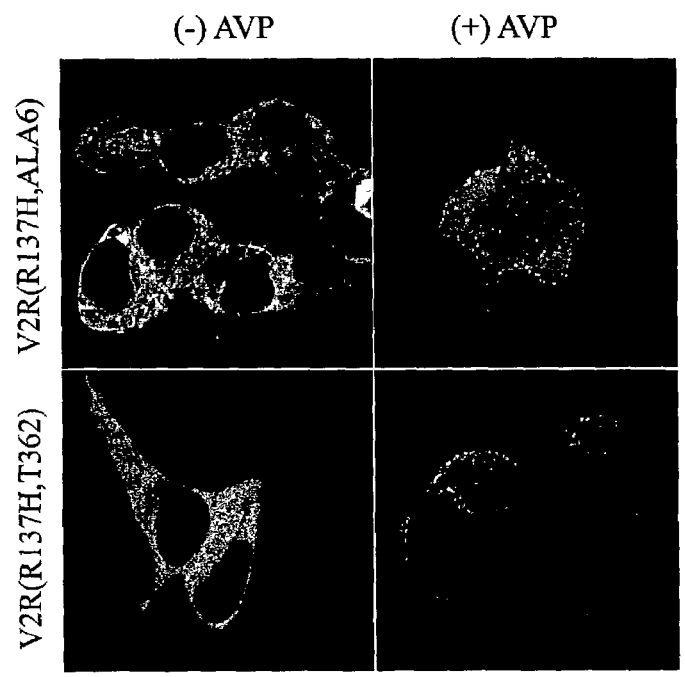
FIG. 9 illustrates the βarrestin2-GFP translocation and adenylyl cyclase response of V2R, V2R(R137H, Ala6), and V2R(R137H, T362) in HEK-293 cells. (A) In the absence of agonist (Left), GFP fluorescence is cytosolic. Following exposure of the cells to 100 nM AVP for 30 min. at 37° C., GFP fluorescence redistributes to punctate areas of plasma membrane (Right). (B) Cells were treated with vehicle or 2.5 μM AVP for 15 min., and whole cell cAMP was determined as described in the Examples below. The absolute basal and stimulated cAMP responses were presented in units of (counts of [$^3$H]cAMP per min. per well)/(counts of [$^3$H] adenine uptake per minute per well) and were: mock (0.019±0.009, 0.017±0.006, n=3); V2R(R137H) (0.018±0.0045, 0.040±0.008, n=4); V2R(R137H,Ala6) (0.020±0.0017, 0.23 ±0.040, n=4); V2R(Ala6) (0.017±0.0006, 1.3±0.31, n=3); V2R(R137H, T362) (0.022±0.0056, 0.22±0.070, n=4); V2R(T362) (0.015±0.0021, 1.3±0.34, n=3); and V2R (0.021±0.0024, 1.4±0.19, n=4). Data are expressed as the mean±SD of three to four separate experiments.

That the V2R(RI37H, Ala6) and V2R(RI37H, T362) receptor mutants have a lower affinity for βarrestin is demonstrated in FIG. 9A, using the βarrestin2-GFP fusion protein. In contrast to the findings for the V2R(RI37H), the V2R(RI37H, Ala6) and V2R(RI37H, T362) are not constitutively associated with βarrestin as indicated by the homogenous distribution of βarrestin2-GFP in the cytoplasm of cells in the absence of hormone. Addition of AVP promotes βarrestin2-GFP redistribution to punctuate at the plasma membrane, but its subsequent redistribution with the receptor into endocytic vesicles does not occur. The inability of βarrestin 2-GFP to remain associated and traffic with V2R in which the serine cluster has been removed reflects decreased receptor affinity for arrestins.

Figure 9B:
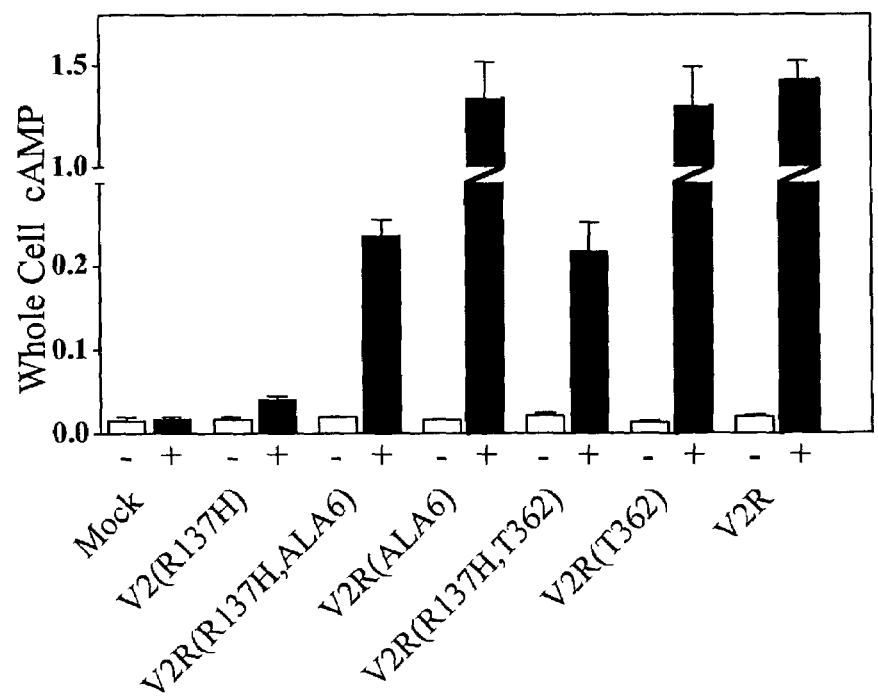

The reduced ability of the V2R(RI37H, Ala6) and V2R (RI37H, T362) to bind βarrestins may improve their ability to stimulate cAMP. FIG. 9B shows that the basal cAMP responses of all the receptor variants are similar. Consistent with findings made in COS-7 cells, a small agonist-mediated increase in cAMP concentration over basal cAMP for the V2R(RI37H) was observed. Mutation of the serine cluster in the V2R(RI37H) C-tail resulted in a six-fold enhancement in cAMP production of both the V2R(RI37H, Ala6) and V2R (RI37H, T362) mutants (FIG. 9B). These data suggest that the V2R(RI37H) interacts with G-protein, albeit less well than the wild type V2R, and that its strong affinity for arrestin markedly inhibits this interaction.

Example 8

Figure 10A:
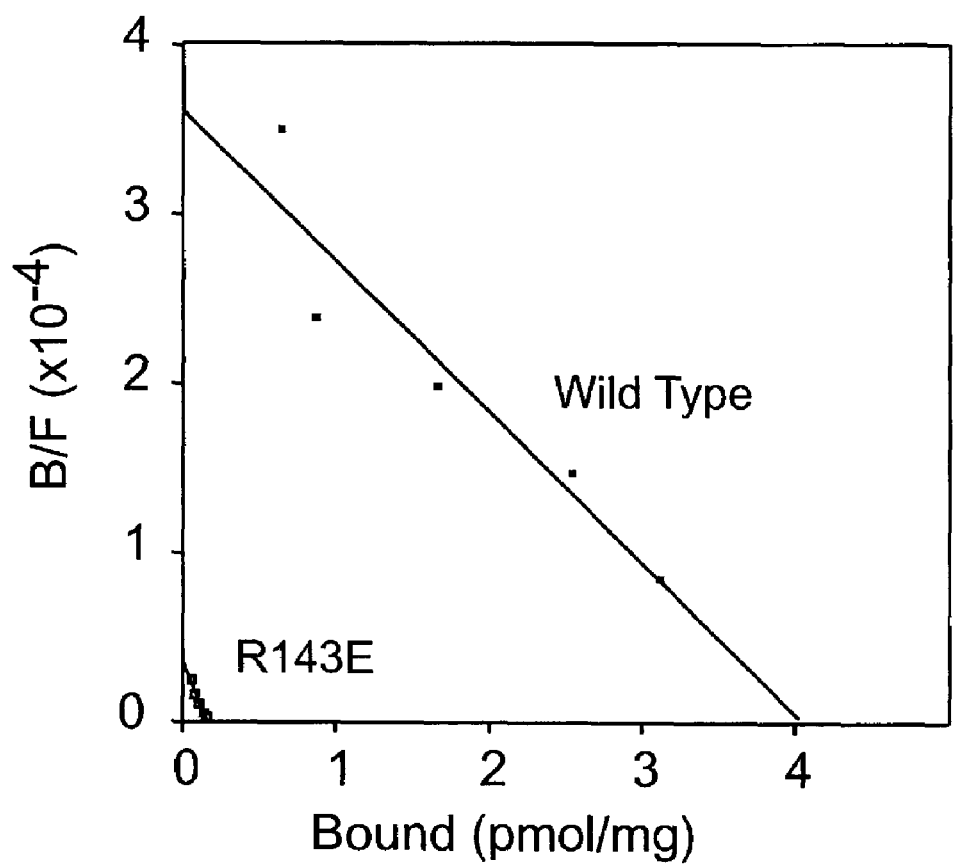
FIG. 10 illustrates the expression of wild type $\alpha_{1B}$-AR and $\alpha_{1B}$-AR R143A in HEK-293 cells. Cells transiently transfected with cDNA for the wild type $\alpha_{1B}$-AR (■) or the $\alpha_{1B}$-AR R143A mutant (□) were exposed to varying concentrations of [$^3$H]prazosin. (A) Scatchard analysis indicates that the $\alpha_{1B}$-AR R143A mutants display a lower $B_{max}$ than the wild type $\alpha_{1B}$-AR. Plasma membrane expression of the wild type $\alpha_{1B}$-AR varied between 1.5 and 4 pmol/mg of whole cell protein, while the expression of $\alpha_{1B}$-AR R143A varied between 0.2 and 0.5 pmol/mg. The $K_D$ of the $\alpha_{1B}$-AR R143A mutant for norepinephrine (NE) was similar to the $K_D$ of the wild type $\alpha_{1B}$-AR for NE (between 1.5 and 3.5 nM). The data are representative of three independent experiments, with each point measured in duplicate. (B) Fluorescence images of live, unpermeabilized HEK-293 cells expressing the wild type $\alpha_{1B}$-AR (Left) or the $\alpha_{1B}$-AR R143A (Right) illustrate the lower surface expression of the $\alpha_{1B}$-AR R143A compared to the wild type $\alpha_{1B}$-AR. Cells were labeled with mouse monoclonal anti-HA antibody and mouse anti-IgG FITC-conjugated secondary antibody.
Figure 10B:
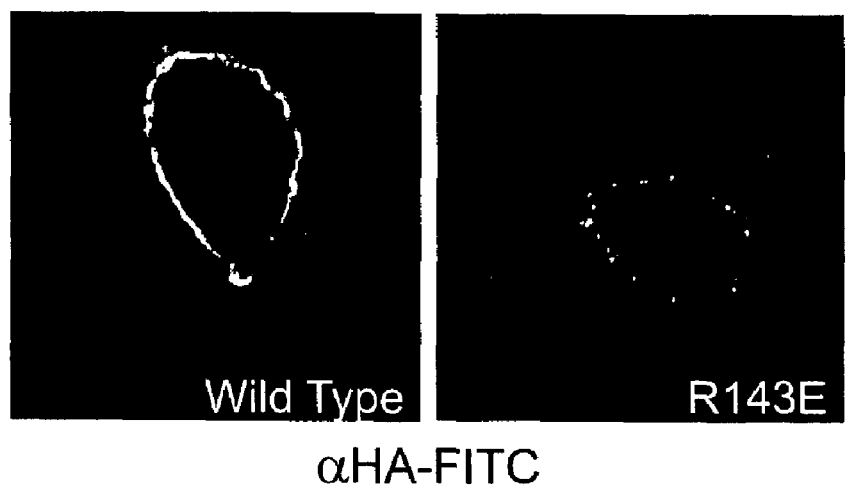

Expression of Wild Type $\alpha_{1B}$-AR and $\alpha_{1B}$-AR R143E in HEK-293 Cells The plasma membrane expression of $\alpha_{1B}$-AR and $\alpha_{1B}$-AR R143E were determined by whole cell binding of [$^3$H] prazosin, as shown in FIG. 10. Scatchard plot analysis indicates that the $B_{max}$ of the $\alpha_{1B}$-AR R143E is markedly lower than the wild type $\alpha_{1B}$-AR. This observation was confirmed by immunofluorescence using live, unpermeabilized cells expressing wild type $\alpha_{1B}$-AR or $\alpha_{1B}$-AR R143E tagged with an HA-epitope. Cells were incubated with an anti-HA antibody followed by a FITC labeled secondary antibody. The amount of fluorescence originating from the plasma membrane of the cells expressing the $\alpha_{1B}$-AR R143E (FIG. 10B, right panel) is much lower than the wild type $\alpha_{1B}$-AR (left panel), indicating a reduced surface expression of the $\alpha_{1B}$-AR R143E.

Example 9

Signaling of the $\alpha_{1B}$-AR and $\alpha_{1B}$-AR R143 Mutants

Figure 11:
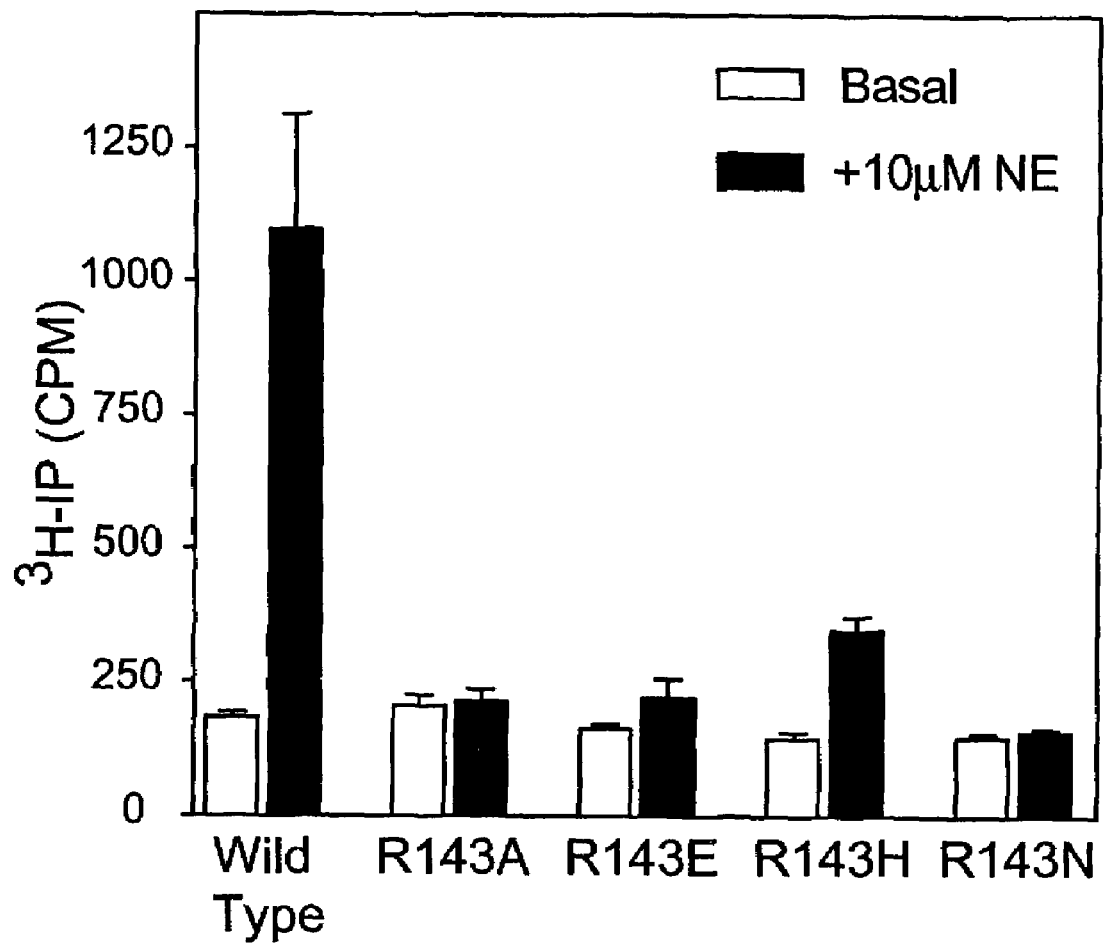
FIG. 11 illustrates the norepinephrine (NE) stimulation of inositol phosphate (IP) accumulation. HEK-293 cells transiently transfected with cDNA for the wild type $\alpha_{1B}$-AR or the $\alpha_{1B}$-AR R143 mutants and stimulated for 30 min. with 10 μM NE. Inositol phosphate accumulation is measured as described and expressed as the total counts of [$^3$H]IP per well of cells. The data are representative of three independent experiments, with each point measured in triplicate.

To determine if the $\alpha_{1B}$-AR R143 mutants are constitutively desensitized, the $\alpha_{1B}$-AR R143 mutants (R143 mutants here refers to substitution with Alanine, Glutamic acid, Histidine, or Asparagine), the [$^3$H]IP accumulation in HEK-293 cells expressing wild type $\alpha_{1B}$-AR or $\alpha_{1B}$-AR R143 mutants was measured (FIG. 11). Cells expressing wild type $\alpha_{1B}$-AR displayed a low accumulation of [$^3$H]-IP in the absence of agonist, with a 6-fold increase upon addition of 10 µM NE. In contrast, the $\alpha_{1B}$-AR R143 mutants displayed a significantly impaired ability to mediate an agonist-induced IP response. In contrast, the $AT_{1A}R$ R126H mutant when stimulated with 1 µM AngII only displays a slight impairment of signaling compared to the stimulated wild type $AT_{1A}R$.

Example 10

Localization of $\alpha_{1B}$-AR and $\alpha_{1B}$-AR R143-GFP Mutants in Response to Norepinephrine (NE)

Figure 12A:
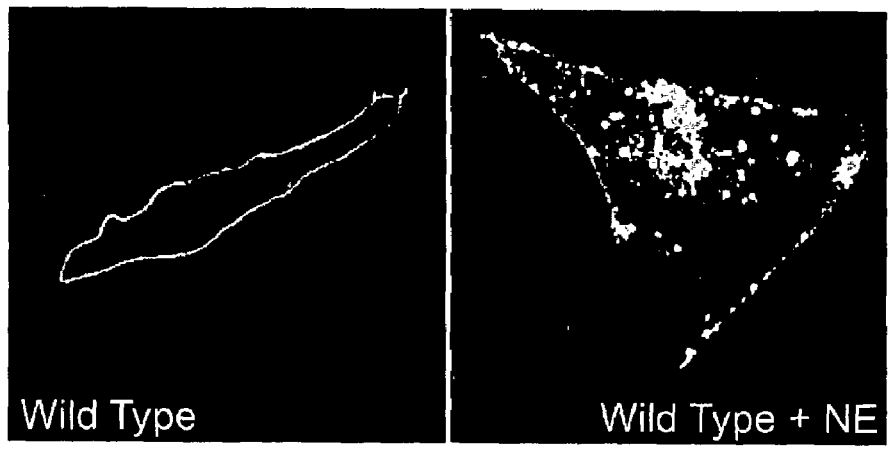
FIG. 12 illustrates the fluorescence images of the wild type $\alpha_{1B}$-AR-GFP and the $\alpha_{1B}$-AR R143-GFP mutants in HEK-293 cells. (A) Cells expressing wild type $\alpha_{1B}$-AR-GFP, when left unstimulated, localize to the plasma membrane (Left). Addition of 10 μM NE to the cells results in the redistribution of the receptor to endosomes (Right). (B) Cells expressing $\alpha_{1B}$-AR R143-GFP mutants are localized in endosomes in the absence of agonist.
Figure 12B:
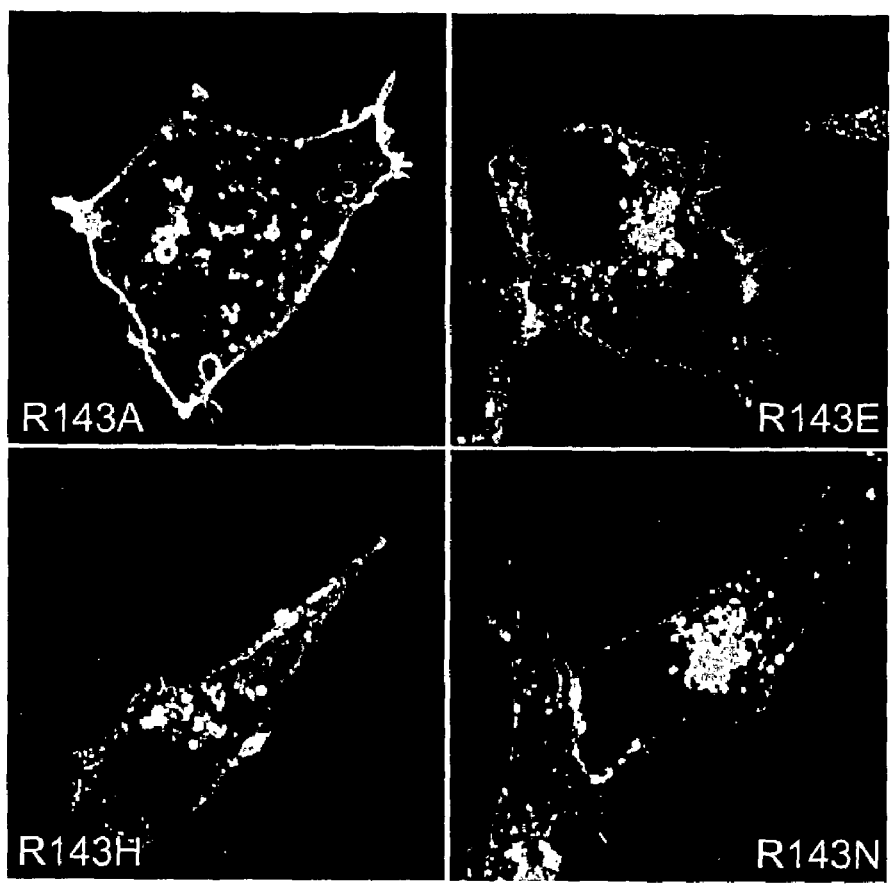

Since the lack of membrane expression of the $\alpha_{1B}$-AR R143A shown by the binding data might suggest an impairment of receptor processing, we determined the cellular localization of wild type $\alpha_{1B}$-AR and the $\alpha_{1B}$-AR R143 mutants using chimeras of the receptors tagged at the C-terminus with green fluorescent protein (GFP). FIG. 12A illustrates that when HEK-293 cells are transfected with wild type $\alpha_{1B}$-AR-GFP, the fluorescence signal as revealed by confocal microscopy originates predominantly from the plasma membrane in the absence of agonist. Addition of 10 µM NE to cells expressing wild type $\alpha_{1B}$-AR-GFP results in a loss of plasma membrane expression and the redistribution of the receptor to endocytic vesicles. In contrast, FIG. 12B illustrates that even in the absence of agonist, the $\alpha_{1B}$-AR R143-GFP mutants are localized predominantly in endocytic vesicles, similar to what was found with the constitutively desensitized V2R R137H. Exposure of cells expressing $\alpha_{1B}$-AR R143-GFP mutants to agonist enhanced the endosomal distribution of the remaining plasma membrane receptor (data not shown).

Example 11

Distribution of βarrestin-GFP in HEK-293 Cells Expressing $\alpha_{1B}$-AR

Figure 13A:
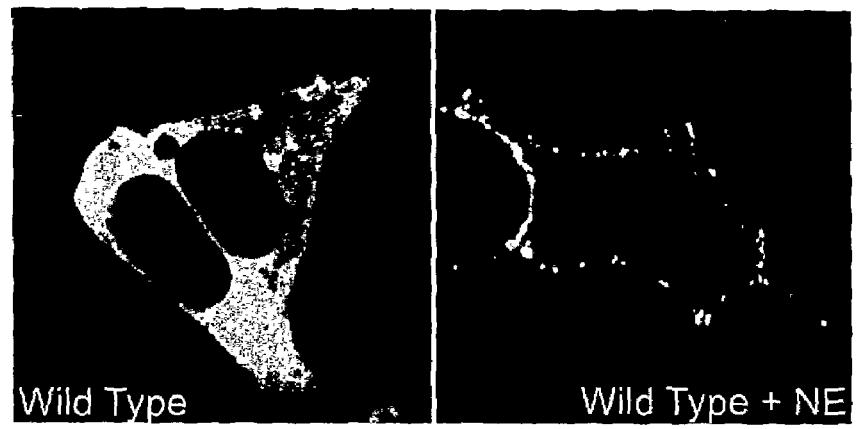
FIG. 13 illustrates the fluorescence images in HEK-293 cells of the association between βarrestin-GFP and the wild type $\alpha_{1B}$-AR or the $\alpha_{1B}$-AR R143 mutants. (A) βarrestin-GFP is distributed predominantly in the cytosol when co-expressed with the wild type $\alpha_{1B}$-AR (Left). Addition of 10 μM NE causes βarrestin-GFP translocation to the plasma membrane in cells expressing the wild type $\alpha_{1B}$-AR (Right). (B) βarrestin-GFP is partially translocated to the plasma membrane in the absence of agonist when expressed with the $\alpha_{1B}$-AR R143 mutants.
Figure 13B:
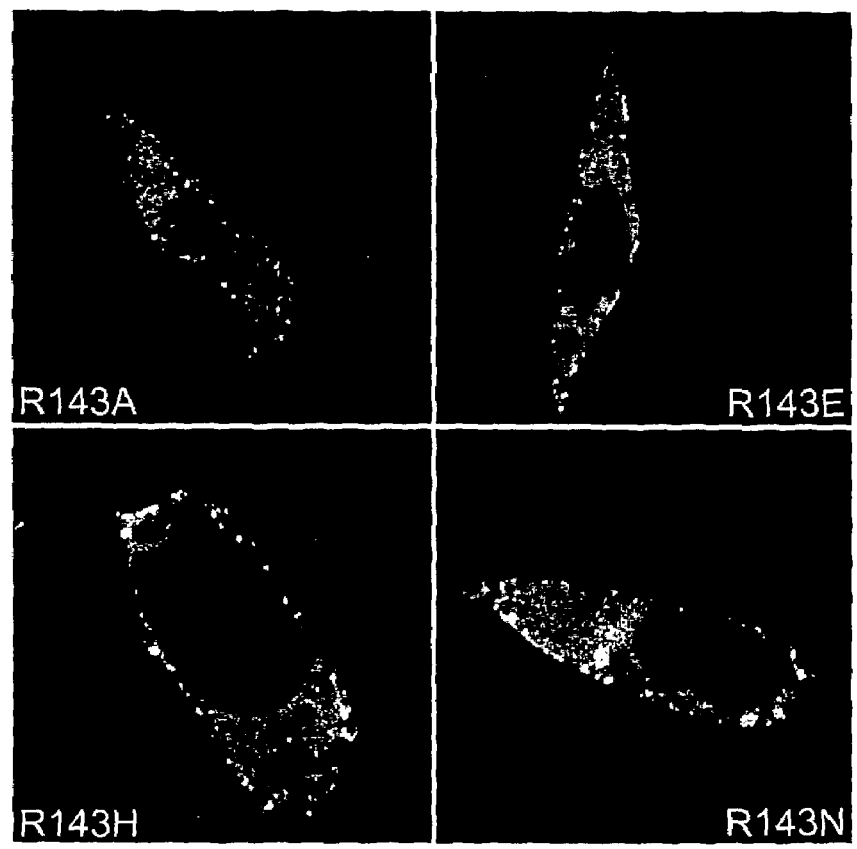

Agonist-stimulated $\alpha_{1B}$-AR have been previously shown to promote the translocation of cytosolic βarrestin to the plasma membrane, an event that is associated with the desensitization and endocytosis of activated receptors (Mhaouty-Kodja, S., et al., 1999, Mol. Pharmacol. 55: 339–347). To observe how the distribution of βarrestin is affected by the $\alpha_{1B}$-AR R143 mutants, we co-expressed βarrestin-GFP with these receptors in HEK-293 cells. FIG. 13A illustrates that in the absence of agonist, βarrestin-GFP is uniformly distributed in the cytosol of cells expressing the wild type $\alpha_{1B}$-AR, and that the addition of 10 µM NE to the cells results in the rapid translocation of βarrestin-GFP to the plasma membrane. This pattern of translocation is reminiscent of so-called class A receptors such as the β$_2$-adrenergic receptor (β$_2$-AR) (Oakley, R. H., et al., 2000, J. Biol. Chem. 275: 17201–17210). Activation of class A receptors leads to plasma membrane translocation of βarrestin without its subsequent co-trafficking into endocytic vesicles, as is the case for class B receptors such as the V2R (Oakley, R. H., et al). In cells co-expressing βarrestin-GFP and the $\alpha_{1B}$-AR R143 mutants, the localization of βarrestin-GFP also appears partially at the plasma membrane without the addition of agonist, in contrast to its distribution with the wild type $\alpha_{1B}$-AR (FIG. 13B). The ability of the mutants to translocate βarrestin-GFP in the absence of agonist suggests that they have a higher affinity for βarrestin than does the wild type receptor without agonist (Oakley, R. H., et al.).

The addition of 10 µM NE to cells co-expressing βarrestin-GFP and the $\alpha_{1B}$-AR R143 mutants enhances this translocation (data not shown).

Example 12

Reversal of the $\alpha_{1B}$-AR R143 Constitutive Desensitization with Antagonist or Dynamin(K44A)

Figure 14A:
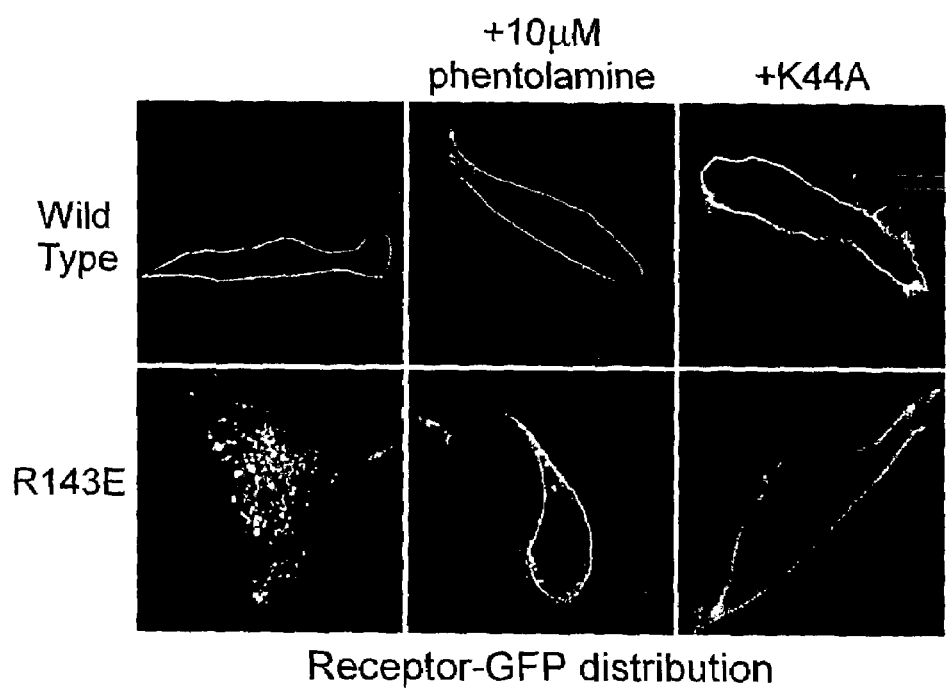
FIG. 14 illustrates the fluorescence images in HEK-293 cells of the wild type $\alpha_{1B}$-AR-GFP and the $\alpha_{1B}$-AR R143E-GFP mutants when cultured with phentolamine or co-expressed with dynamin(K44A). (A) Cells expressing the wild type $\alpha_{1B}$-AR-GFP (Upper) or $\alpha_{1B}$-AR R143E-GFP (Lower) were left untreated (Left), cultured in 10 μM phentolamine at 37° C. overnight (Center), or co-expressed with dynamin (K44A) (Right). Both the phentolamine treatment and the co-expression of dynamin(K44A) result in a redistribution of the $\alpha_{1B}$-AR R143E-GFP from endosomes to the plasma membrane, while the same conditions have no effect on the distribution of the wild type $\alpha_{1B}$-AR-GFP. (B) Whole cell binding with [$^3$H]prazosin was evaluated in HEK-293 cells expressing the wild type $\alpha_{1B}$-AR-GFP or the $\alpha_{1B}$-AR R143E-GFP mutants. Cells were either left untreated, cultured in 10 µM phentolamine at 37° C. overnight, or co-expressed with dynamin(K44A). The $\alpha_{1B}$-AR R143E-GFP is expressed at a lower density on the plasma membrane than the wild type $\alpha_{1B}$-AR-GFP. Expression of the $\alpha_{1B}$-AR R143E-GFP mutant increases to the level of the wild type receptor when the cells are either cultured in phentolamine or co-expressed with dynamin(K44A).
Figure 14B:
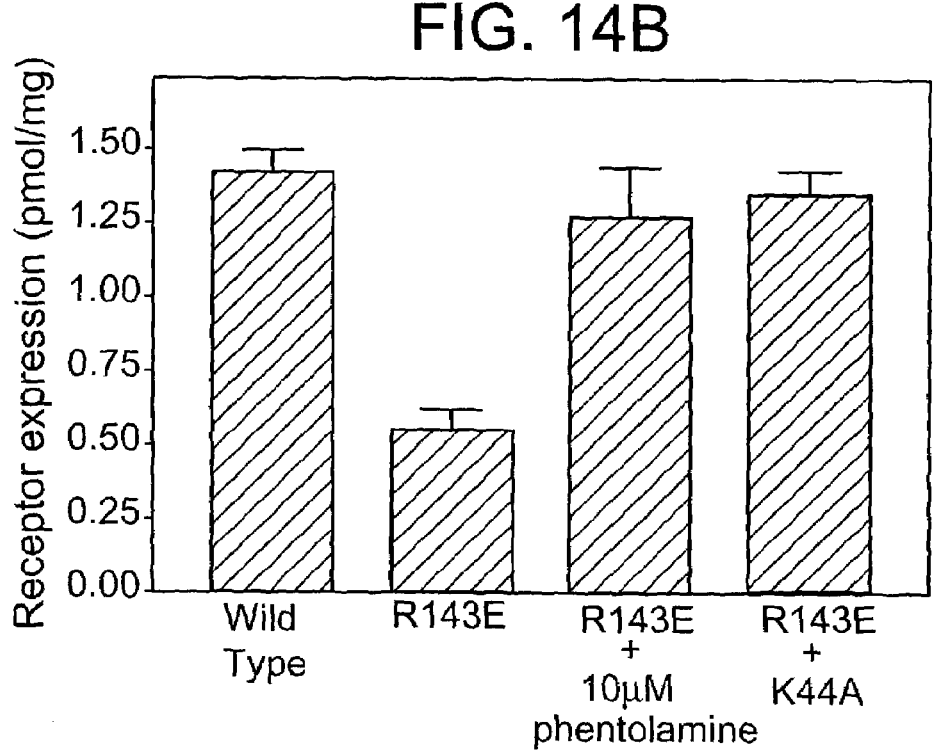

The low membrane expression and intracellular localization of the mutant receptors as revealed by the receptor-GFP constructs may reflect their inability to ever reach the plasma membrane. For instance, the receptors may be inappropriately folded and/or processed in the endoplasmic reticulum. However, if the loss of expression is due to their constitutive association with βarrestin, as shown in FIG. 14B, it would suggest that the mutant receptors traffic to the plasma membrane before being internalized into endocytic vesicles. Two approaches were employed to determine if the $\alpha_{1B}$-AR R143E mutants could be trapped on the plasma membrane, reversing the constitutive internalization in endocytic vesicles. The first method utilized a selective antagonist to the $\alpha_{1B}$-AR, phentolamine. FIG. 14A illustrates that HEK-293 cells transfected with the wild type $\alpha_{1B}$-AR-GFP express the receptor predominantly at the plasma membrane (upper left panel). HEK-293 cells transfected with the wild type $\alpha_{1B}$-AR-GFP and cultured overnight in the presence of 10 µM phentolamine showed no alteration in the expression of the receptor at the plasma membrane (upper center panel). However, the $\alpha_{1B}$-AR R143E-GFP in HEK-293 cells was predominantly localized inside endocytic vesicles (lower left panel), while in the presence of phentolamine a complete reversal was observed and the mutants were localized at the plasma membrane (lower center panel). The second method employed to reverse the constitutive desensitization was the co-expression of the receptors with dynamin(K44A), an endocytic protein variant that competitively inhibits the fission of clathrin-coated vesicles from the plasma membrane (Zhang, J., et al., 1997, J. Biol. Chem. 272: 27005–27014). $\alpha_{1B}$-AR R143E-GFP when co-expressed with dynamin(K44A) was unable to undergo endocytosis and its expression remained at the plasma membrane (lower right panel). Whole cell binding (FIG. 14B) confirmed that while the untreated $\alpha_{1B}$-AR R143E cells displayed a lower receptor expression on the plasma membrane compared to the wild type $\alpha_{1B}$-AR, the presence of an antagonist or the co-expression of dynamin(K44A) was able to increase the expression of the $\alpha_{1B}$-AR R143E on the plasma membrane to the level of the wild type $\alpha_{1B}$-AR.

Example 13

Distribution of βarrestin in HEK-293 Cells Expressing $AT_{1A}R$

Figure 15A:
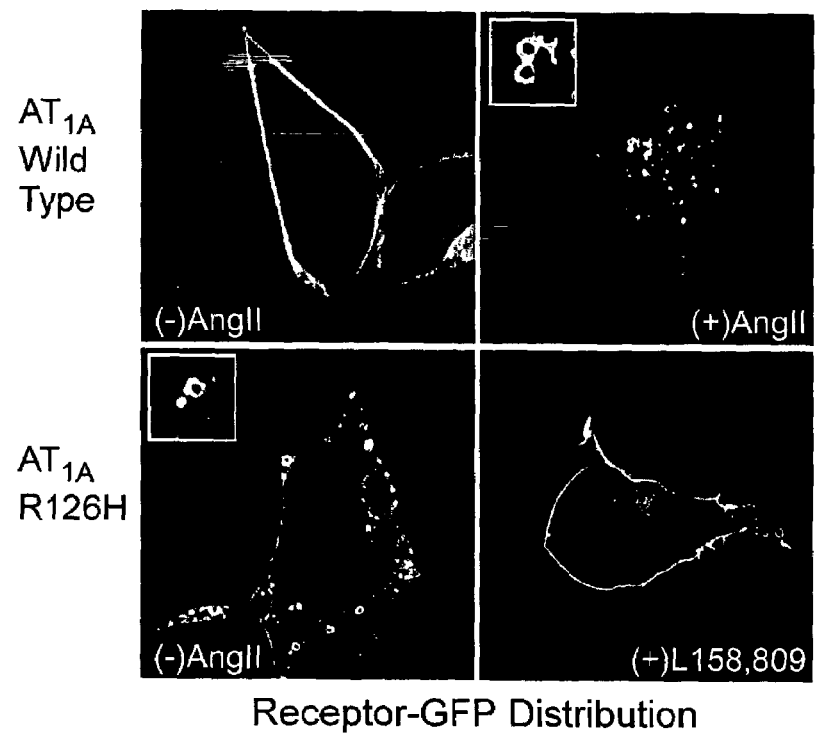
FIG. 15 illustrates the fluorescence images illustrating the distribution of the wild type $AT_{1A}$R-GFP, the $AT_{1A}$R-R126H-GFP mutant, and βarrestin-GFP in HEK-293 cells. (A) Cells express $AT_{1A}$R-GFP predominantly on the plasma membrane, and the addition of 1 µM angiotensin II (AngII) results in the redistribution of the receptor from the plasma membrane to endosomes (Upper). Cells express $AT_{1A}$R R126H-GFP in endosomes in the absence of agonist, and culturing the cells in 1 µM L158,809 results in the redistribution of the receptor back to the plasma membrane (Lower). (B) βarrestin-GFP co-expressed with wild type $AT_{1A}$R is distributed predominantly in the cytosol, and the addition of 1 µM AngII results in the translocation of βarrestin-GFP to endosomes (Upper). In contrast, βarrestin-GFP co-expressed with $AT_{1A}$R R126H-GFP is distributed in endosomes in the absence of agonist, and this distribution is enhanced upon addition of 1 µM AngII (Lower).
Figure 15B:
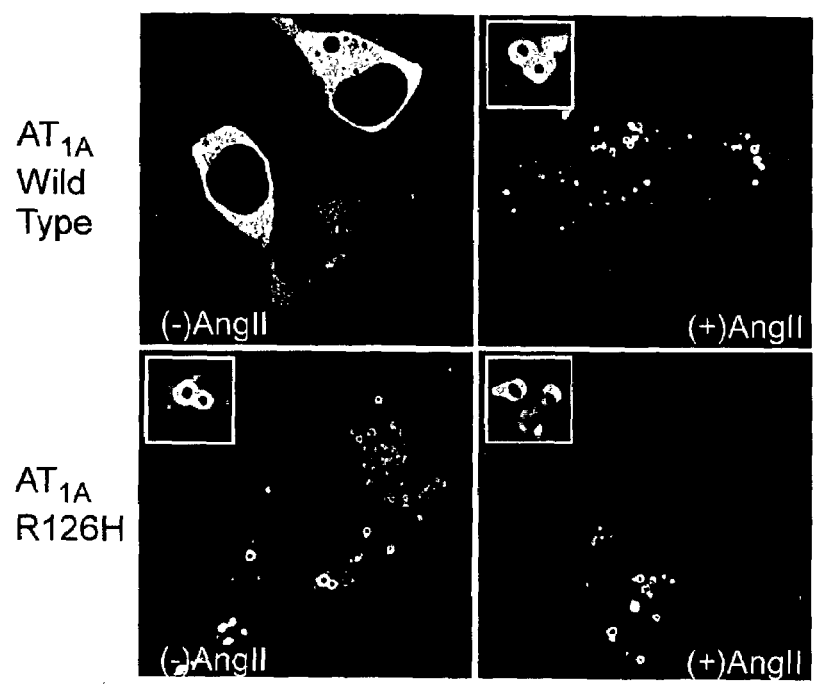

To determine if the constitutive desensitization resulting from mutation of the DRY motif arginine could be extended to another GPCR, we repeated the receptor-GFP localization and βarrestin-GFP translocation experiments using the $AT_{1A}R$. FIG. 15A illustrates that wild type $AT_{1A}R$-GFP when transfected into HEK-293 cells is expressed predominantly on the plasma membrane, and that addition of 1 µM angiotensin II (AngII) results in the internalization of the receptor into endocytic vesicles. In contrast, $AT_{1A}R$ R126H-GFP transfected into HEK-293 cells is localized in endocytic vesicles without the addition of agonist. Furthermore, when cells expressing $AT_{1A}R$ R126H-GFP are cultured in the $AT_{1A}R$ selective antagonist, L158,809, a reversal of the receptor localization back to the plasma membrane occurs. FIG. 15B illustrates that βarrestin-GFP is uniformly distributed in the cytosol of HEK-293 cells expressing the wild type $AT_{1A}R$, and that addition of 1 µM AngII causes redistribution of the βarrestin-GFP into endocytic vesicles. In contrast, βarrestin-GFP when co-expressed with the $AT_{1A}R$ R126H is distributed predominantly in endocytic vesicles in the absence of agonist. Addition of 1 µM AngII to cells expressing $AT_{1A}R$ R126H resulted in an enhanced distribution of βarrestin-GFP into endocytic vesicles.

Example 14

Signaling of the $AT_{1A}R$ R126H in the Presence or Absence of GRKs

Figure 16A:
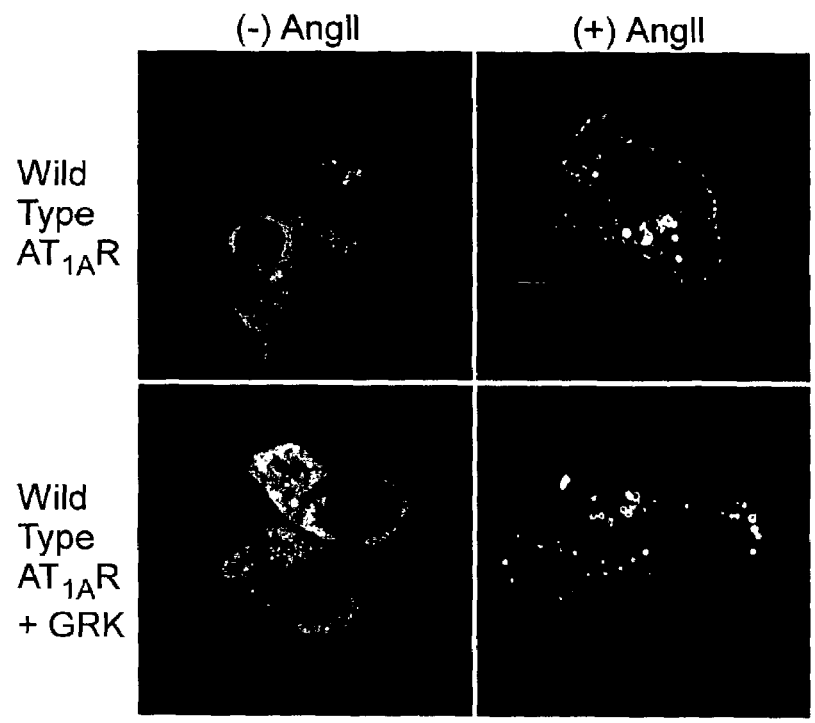
FIG. 16 illustrates the effect of overexpression of the GRKs on the internalization of the $AT_{1A}$R. (A) Upper panels illustrate the localization of βarrestin-GFP in HEK-293 transfected with wild-type $AT_{1A}$R, in the presence and absence of AngII. Lower panels illustrate the localization of βarrestin-GFP in HEK-293 transfected with wild-type $AT_{1A}$R, with the co-transfection of GRKs. (B) Upper panels illustrate the localization of βarrestin-GFP in HEK-293 transfected with the R126H mutant of $AT_{1A}$R, in the presence and absence of AngII. Lower panels illustrate the localization of βarrestin-GFP in HEK-293 transfected with R126H mutant of $AT_{1A}$R, with the co-transfection of GRKs. (C) [$^3$H]-IP accumulation was determined for the above cells.
Figure 16B:
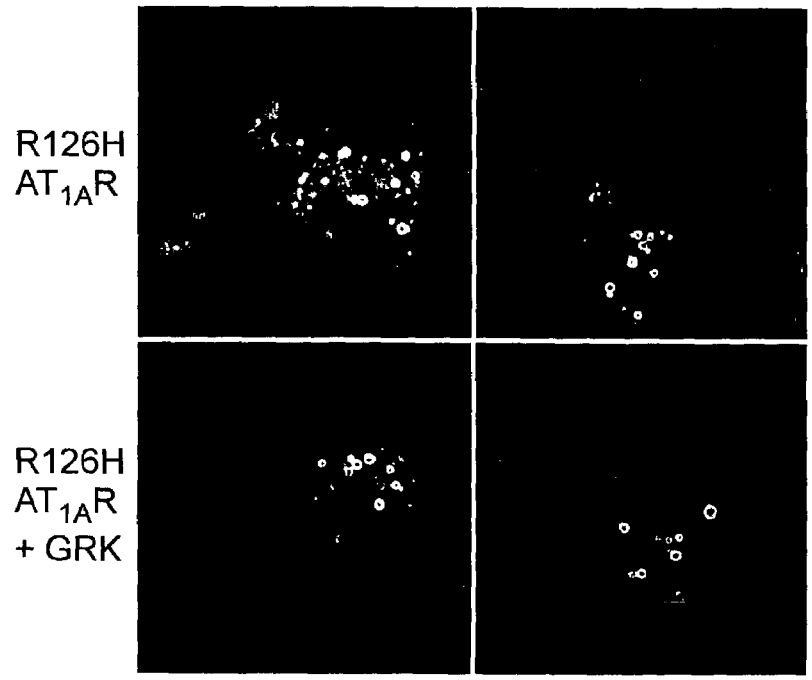
Figure 16C:
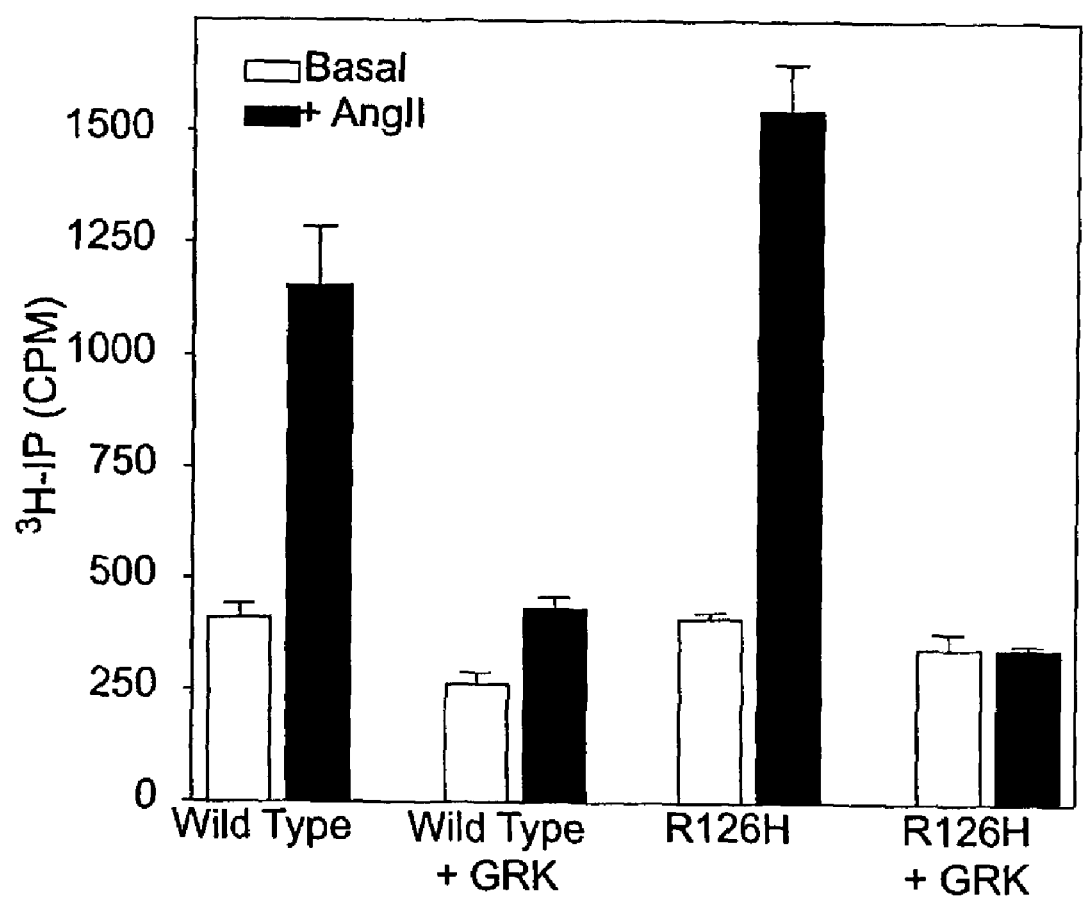

Given the fact that other GPCRs with DRY motif Arginine mutations lost their ability to couple to G proteins and that $AT_{1A}R$ R126H in able to translocate βarrestin-GFP in the absence of agonist (as shown in FIG. 15B), $AT_{1A}R$ R126H was predicted to also exhibit a loss of signaling phenotype. However, HEK cells transfected with the $AT_{1A}R$ R126H and stimulated with AngII were able to accumulate $[^3H]$-IP at levels identical to HEK cells transfected with wild type $AT_{1A}R$ and stimulated with AngII (FIG. 16C). To determine if the signaling of the $AT_{1A}R$ R126H could be abolished by overexpressing GRKs and what effect this has on the localization of βarrestin-GFP, we transfected HEK cells with wild type $AT_{1A}R$ or $AT_{1A}R$ R126H either with or without equal amounts of GRK plasmid cDNA. Cells were either co-transfected with βarrestin-GFP for confocal microscope viewing, or incubated with $[^3H]$-inositol to measure $[^3H]$-IP accumulation. FIG. 16A (left top and bottom panels) shows that in HEK cells transfected with βarrestin-GFP and the wild type $AT_{1A}R$, the localization of βarrestin-GFP is distributed throughout the cytosol with or without the co-transfection of GRKs. Upon the addition of 1 µg AngII to these cells, after 5 minutes the βarrestin-GFP translocates to endocytic vesicles (FIG. 16a, right panels, top and bottom). FIG. 16B illustrates that HEK cells transfected with βarrestin-GFP and $AT_{1A}R$ R126H results in a partial translocation of βarrestin-GFP to endocytic vesicles (top left panel), with a notable amount of βarrestin-GFP remaining in the cytosol. This remaining cytosolic βarrestin-GFP translocates to endocytic vesicles upon the addition of 1 µg AngII, as shown in FIG. 16B (top right panel). HEK cells transfected with βarrestin-GFP, $AT_{1A}R$ R126H, and GRKs, however, result in a complete translocation of βarrestin-GFP to endocytic vesicles without the addition of agonist as shown in FIG. 16B (bottom left panel). The βarrestin-GFP remains completely localized in endocytic vesicles when these cells are exposed to 1 µg AngII (FIG. 16B, bottom right panel). To measure the signaling ability of cells overexpressing GRKs with the wild type $AT_{1A}R$ or R126H, HEK cells were transiently transfected with 1 µg receptor cDNA either with or without equal amounts of GRK cDNA. These cells were then incubated in $[^3H]$-inositol, and the $[^3H]$-IP accumulation was measured in the basal state or upon the addition of 1 µg AngII. FIG. 16C indicates that both the wild type $AT_{1A}R$ and $AT_{1A}R$ R126H accumulate equivalent amounts of $[^3H]$-IP upon stimulation with 1 µg AngII. However, the overexpression of GRKs is able to completely abolish the accumulation of [3H]-IP in $AT_{1A}R$ R126H cells stimulated with agonist, whereas the wild type $AT_{1A}R$ only experiences a decrease in $[^3H]$-IP accumulation when stimulated with agonist.

Example 15

Increased Arrestin Expression Results in Constitutively Desensitized GPCRs

As described above, GRKs expressed at levels above background can result in constitutive endosomal localization of the GPCR. The increased (with respect to wild-type) levels of GRK results in increased phosphorylation of the GPCR. The hyper-phosphorylated GPCR has increased (with respect to wild-type) affinity for arrestin, resulting in increased (with respect to wild-type) constitutive endosomal localization of the GPCR.

Likewise, arrestin will be expressed at levels above background, will have increased GPCR binding, and therefore will result in constitutive desensitization, most preferably constitutive endosomal localization of the GPCR.

Example 16

The Presence of Phosphorylation Sites in the GPCRs Result in Constitutively Desensitized GPCRs As described in FIG. 9, the SSSTSS to AAAAAA mutation in the V2R C-terminal tail (as described in U.S. Ser. No. 09/993,844, and incorporated by reference in its entirety, and Oakley et al., 2001, J. Biol. Chem. 276:19452–19460) inhibits the constitutive endosomal localization of the GPCR. The mutation of highly phosphorylatable amino acids (such as Serine and Threonine) to lesser phosphorylatable amino acids (such as Alanine) of the phosphorylation sites of the C-terminal tail of the GPCR results in decreased GPCR phosphorylation by the GRKs, decreased arrestin binding to the GPCR, and decreased endosomal localization of the GPCR.

Likewise, at phosphorylation sites of C-terminal tails of certain GPCRs, the mutation of lesser phosphorylatable amino acids to highly phosphorylatable amino acids (as described in U.S. Ser. No. 09/993,844 and Oakley et al., 2001, J. Biol. Chem. 276:19452–19460) will result in increased phosphorylation of the GPCR. These phosphorylation sites can be added at the C-terminal tails of the modified GPCRs of the present invention. The resulting modified GPCR would have, in addition to a modified DRY motif, highly phosphorylatable amino acids in its C-terminal tail, will be hyper-phosphorylated, will bind arrestin with increased affinity (with respect to wild-type). This will result in constitutive desensitization, most preferably constitutive endosomal localization of the GPCR.

Example 17

Uses of Arrestin Knockout Mice

By way of example, the arrestin knockout mice of the present invention will be used as a mouse model of arrestin inhibitors. The antagonists identified as arrestin inhibitors will be analyzed in wild-type mice. The arrestin knockout mice of the present invention will be used to determine if the arrestin antagonists function as would an arrestin knockout.

Example 18

Production of Arrestin Knockout Mice

By way of example, βarrestin-2 knockout (βarr2-KO) mice were generated by inactivation of the gene by homologous recombination. A bacteriophage λ library of mouse 129SvJ genomic DNA (Stratagene, La Jolla, Calif.) was screened with the rat βarr2 cDNA (H. Attramadal et al., *J Biol. Chem.* 267, 17882 (1992)). Positive phages were identified and analyzed by restriction digest. A 12-kb βarr2 fragment was digested with Bam HI, subcloned into pBluescript KS(−) and sequenced. The targeting vector was assembled by blunt-end ligation of a pHSV-TK cassette (from pIC19R/MCI-TK, M. R. Capecchi, University of Utah), a 2.8-kb Nco I-Bam HI βarr2 fragment, a pGK-neo cassette (from plasmid pD383, R. Hen, Columbia University) which replaced the 0.8 kb Bam HI-Hind III fragment of βarr2, and a 4.5 kb Hind III βarr2 fragment into pBluescript KS(−). This targeting vector was linearized with Not I and was electroporated into mouse embryonic stem cells. Genomic DNA from transfectants resistant to G418 and gancyclovir were isolated and screened by Southern (DNA) blot analysis using a 0.2 kb 5' external βarr2 probe and a 0.3 kb 3' external βarr2 probe. Chimeric animals were generated by microinjecting these ES cells into C57BL/6 blastocysts. Five chimeric male pups were obtained and mated with C57BL/6 females. Germline transmission was confirmed by Southern blotting. Heterozygous, offspring were intercrossed to obtain homozygous mice. Wild-type and mutant mice used in this study were age-matched, 3 to 5 month old, male siblings. For protein immunoblot analysis, whole cell lysates were prepared by polytron homogenization in lysing buffer (10 mM Tris (pH 7.4), 5 mM EDTA, 1 protease inhibitor tablet/10 mL (Roche Molecular Biochemicals, Indianapolis, Ind., USA), 1% nonidet-40). Polyacrylamide gels were loaded with 25 µg protein/lane and equivalent protein loading was confirmed by Ponceau S staining of the gels. After transfer to polyvinyldifluoride (PVDF) membranes, proteins were blotted with polyclonal antibodies to βarrestin-2 or βarrestin-1 (H. Attramadal et al., *J Biol. Chem.* 267:17882–17890 (1992)). Bands were visualized with secondary antibody conjugated to horseradish peroxidase and an enhanced chemiluminescence detection system (Amersham, Piscataway, N.J.).

Mice lacking βarrestin-2 were identified by Southern DNA blot analysis and the absence of βarrestin-2 was confirmed by protein immunoblotting of extracts from brainstem, periaqueductal gray (PAG) tissue, spleen, lung and skin. The βarr2-KO mice were viable and had no gross phenotypic abnormalities.

βarrestin-1 knockout mice and visual arrestin knockout mice may be generated and identified in an analogous manner, substituting inactivation of βarrestin-1 gene and visual arrestin-gene accordingly.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The following documents, as well as any documents referenced in the foregoing text, should be considered as incorporated by reference in their entirety.

Attramadal, H., Arriza, J. L., Aoki, C., Dawson, T. M., Codina, J., Kwatra, M. M., Snyder, S. H., Caron, M. G. & Lefkowitz, R. J. (1992) J. Biol. Chem. 267, 17882–17890

Barak, L. S., Oakley, R. H., Laporte, S. A. and Caron, M. G. (2001) Proc. Natl. Acad. Sci. USA 98, 93–98

Barak, L. S., Warabi, K., Feng, X., Caron, M. G. & Kwatra, M. M. (1999) J. Biol. Chem. 274, 7565–7569

Barak, L. S., Ferguson, S. S., Zhang, J. & Caron, M. G. (1997) J. Biol. Chem. 272, 27497–27500

Barak, L. S., Ferguson, S. S., Zhang, J., Martenson, C., Meyer, T. & Caron, M. G. (1997) Mol. Pharmacol. 51, 177–184

Barak, L. S., Menard, L., Ferguson, S. S., Colapietro, A. M. & Caron, M. G. (1995) Biochemistry 34, 15407–15414

Ferguson, S. S., Barak, L. S., Zhang, J. & Caron, M. G. (1996) Can. J. Physiol. Pharmacol. 74, 1095–1110

Ferguson, S. S., Menard, L., Barak, L. S., Koch, W. J., Colapietro, A. M. & Caron, M. G. (1995) J. Biol. Chem. 270, 24782–24789

Kim, K.-M., Valenzano, K. J., Robinson, S. R., Yao, W. D., Barak, L. S., Caron, M. G. (2001) J. Biol. Chem. 276: 37409–37414

Laporte, S. A., Oakley, R. H., Holt, J. A., Barak, L. S. & Caron, M. G. (2000) J. Biol. Chem. 275, 23120–23126

Laporte, S. A., Oakley, R. H., Zhang, J., Holt, J. A., Ferguson, S. S., Caron, M. G. & Barak, L. S. (1999) Proc. Natl. Acad. Sci. USA 96, 3712–3717

Menard, L., Ferguson, S. S., Zhang, J., Lin, F. T., Lefkowitz, R. J., Caron, M. G. & Barak, L. S. (1997) Mol. Pharmacol. 51, 800–808

Mhaouty-Kodja, S., Barak, L. S., Scheer, A., Abuin, L., Diviani, D., Caron, M. G. & Cotecchia, S. (1999) Mol. Pharmacol. 55, 339–347

Oakley, R. H., Laporte, S. A., Holt, J. A., Barak, L. S., Caron, M. G. (2001). J. Biol. Chem. 276: 19452–19460

Oakley, R. H., Laporte, S. A., Holt, J. A., Caron, M. G. & Barak, L. S. (2000) J. Biol. Chem. 275, 17201–17210

Oakley, R. H., Laporte, S. A., Holt, J. A., Barak, L. S. & Caron, M. G. (1999) J. Biol. Chem. 274, 32248–32257

Wilbanks, A. M., Laporte, S. A., Barak, L. S. & Caron, M. G. (2002) Manuscript submitted.

Zhang, J., Barak, L. S., Anborgh, P. H., Laporte, S. A., Caron, M. G. & Ferguson, S. S. (1999) J. Biol. Chem. 274, 10999–11006

Zhang, J., Barak, L. S., Winkler, K. E., Caron, M. G. & Ferguson, S. S. (1997) J. Biol. Chem. 272, 27005–27014

---

What is claimed is:

1. A nucleic acid selected from the group consisting of SEQ ID NOs: 7–12.

2. A nucleic acid encoding a polypeptide selected from the group consisting of SEQ ID NOs.: 1–6.

3. A vector comprising a nucleic acid of claim 1.

4. An isolated host cell comprising the expression vector of claim 3.

5. A nucleic acid encoding a modified GPCR or biologically active fragment thereof comprising a DRY motif modified to contain an amino acid other than arginine at position 2, wherein the modified GPCR or biologically active fragment thereof is constitutively desensitized in the absence of an agonist, wherein said nucleic acid is at least 80% identical to a nucleic acid selected from the group consisting of SEQ ID NOs: 7–12.

6. A nucleic acid encoding a modified GPCR or biologically active fragment thereof comprising a DRY motif modified to contain an amino acid other than arginine at position 2, wherein the modified GPCR or biologically active fragment thereof is constitutively desensitized in the absence of an agonist, wherein said nucleic acid is at least 90% identical to a nucleic acid selected from the group consisting of SEQ ID NOs: 7–12.

7. A nucleic acid encoding a modified GPCR or biologically active fragment thereof comprising a DRY motif modified to contain an amino acid other than arginine at position 2, wherein the modified GPCR or biologically active fragment thereof is constitutively desensitized in the absence of an agonist, wherein said nucleic acid is at least 95% identical to a nucleic acid selected from the group consisting of SEQ ID NOs: 7–12.

8. A nucleic acid encoding a modified GPCR or biologically active fragment thereof comprising a DRY motif modified to contain an amino acid other than arginine at position 2, wherein the modified GPCR or biologically active fragment thereof is constitutively desensitized in the absence of an agonist, wherein said nucleic acid is at least 98% identical to a nucleic acid selected from the group consisting of SEQ ID NOs: 7–12.

9. A nucleic acid encoding a modified GPCR or biologically active fragment thereof comprising a DRY motif modified to contain an amino acid other than arginine at position 2, wherein the modified GPCR or biologically active fragment thereof is constitutively desensitized in the absence of an agonist, wherein said nucleic acid is at least 99% identical to a nucleic acid selected from the group consisting of SEQ ID NOs: 7–12.

* * * * *